(12) United States Patent
Schteingart et al.

(10) Patent No.: US 8,217,007 B1
(45) Date of Patent: *Jul. 10, 2012

(54) SYNTHETIC PEPTIDE AMIDES

(75) Inventors: Claudio D. Schteingart, San Diego, CA (US); Frédérique Menzaghi, Rye, NY (US); Guangcheng Jiang, San Diego, CA (US); Roberta Vezza Alexander, San Diego, CA (US); Javier Sueiras-Diaz, La Jolla, CA (US); Robert H. Spencer, New Hope, PA (US); Derek T. Chalmers, Riverside, CT (US); Robert Zhiyong Luo, New City, NY (US)

(73) Assignee: Cara Therapeutics, Inc., Shelton, CT (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/786,686

(22) Filed: May 25, 2010

Related U.S. Application Data

(63) Continuation of application No. 12/176,279, filed on Jul. 18, 2008, now Pat. No. 7,727,963, which is a continuation of application No. 11/938,771, filed on Nov. 12, 2007, now Pat. No. 7,402,564.

(60) Provisional application No. 60/858,109, filed on Nov. 10, 2006, provisional application No. 60/928,550, filed on May 10, 2007.

(51) Int. Cl.
*A61K 38/07* (2006.01)
(52) U.S. Cl. .................................... 514/18.4; 514/21.9
(58) Field of Classification Search ........................ None
See application file for complete search history.

(56) References Cited

U.S. PATENT DOCUMENTS

| | | | |
|---|---|---|---|
| 5,965,701 A | 10/1999 | Junien et al. | |
| 6,191,103 B1 | 2/2001 | Shohet et al. | |
| 6,780,846 B1 | 8/2004 | O'Mahoney et al. | |
| 6,984,719 B1 | 1/2006 | Chemtob et al. | |
| 7,244,573 B2 | 7/2007 | Carman et al. | |
| 7,348,162 B2 | 3/2008 | Saris et al. | |
| 7,402,564 B1 | 7/2008 | Schteingart et al. | |
| 2005/0113294 A1 | 5/2005 | Dolle | |
| 2006/0229252 A1 | 10/2006 | Falla et al. | |

FOREIGN PATENT DOCUMENTS

| | | |
|---|---|---|
| DE | 43 10643 A1 | 4/1993 |
| EP | 0 249 169 B1 | 6/1987 |
| EP | 0 334 244 A2 | 3/1989 |
| EP | 0 342 962 B1 | 5/1989 |
| EP | 0 361 977 A2 | 9/1989 |
| EP | 0 505 680 B1 | 1/1992 |
| EP | 0 517 589 B1 | 12/1996 |
| EP | 0 503 301 B1 | 11/1997 |
| WO | 8808429 A1 | 11/1988 |
| WO | 9421242 A1 | 9/1994 |
| WO | 9500546 A1 | 1/1995 |
| WO | 9522557 A1 | 8/1995 |
| WO | 9602267 A1 | 2/1996 |
| WO | 9707130 A1 | 2/1997 |
| WO | 9709995 A1 | 3/1997 |
| WO | 9808492 A1 | 3/1998 |
| WO | 9808868 A1 | 3/1998 |
| WO | 9921877 A1 | 5/1999 |
| WO | 9932510 A1 | 7/1999 |
| WO | 03011896 A1 | 2/2003 |
| WO | 2006058539 A2 | 6/2006 |
| WO | 2006058539 A3 | 6/2006 |

OTHER PUBLICATIONS

Vippagunta "Crystalline solids," Adv. Drug Delivery Rev., 2001, 48, 3-26.*
Byrn et al. Solid State Chemistry of Drugs, 2 Ed. 1999 "Hydrates and Solvates" pp. 233-247.*
Testa "Prodrug research: futile or fertile?" Biochemical Pharmacology, 2004, 68, 2097-2106.*
Bentley, G.A. et al., Evidence for an action of morphine and the enkephalins on sensory nerve endings in the mouse peritoneum, Br. J. Pharmac., 73:325-332 (1981).
Diop, Laurent et al., Peripheral k-opioid receptors mediate the antinociceptive effect of fedotozine on the duodenal pain reflex in rat, European Journal of Pharmacology 271, pp. 65-71 (1994).
Iyer, S. et al., Characterization and Biological Significance of Immunosuppressive Peptide D2702.75-84 (E→V) Binding Protein, J. Biol. Chem., vol. 273, No. 5, pp. 2692-2697 (1998). Junien and Riviere, Review article: the hypersensitive gut—peripheral kappa agonists as a new pharmacological approach, Alimentary Pharmacology and Therapeutics, 9:117-126 (1995).
Lamb, J.R. et al., Influence of antigen structure on the activation and induction of unresponsiveness in cloned human T lymphocytes, Immunology, 57, pp. 331-335 (1986).
Ostergaard, S. et al., Novel avidin and streptavidin binding sequences found in synthetic peptide libraries, FEBS Letters, 362, pp. 306-308 (1995).
Riviere, Pierre J.M. et al., Fedotozine Reverses Ileus Induced by Surgery or Peritonitis: Action at Peripheral K-Opioid Receptors, Gastroenterology 104:724-731 (1993).

(Continued)

*Primary Examiner* — Christina Bradley
(74) *Attorney, Agent, or Firm* — Algis Anilionis; F. Chau & Associates, LLC

(57) ABSTRACT

The invention relates to synthetic peptide amide ligands of the kappa opioid receptor and particularly to agonists of the kappa opioid receptor that exhibit low $P_{450}$ CYP inhibition and low penetration into the brain. The synthetic peptide amides of the invention conform to the structure of formula I:

Formula I

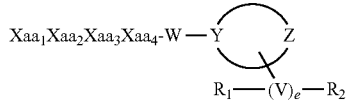

Pharmaceutical compositions containing these compounds are useful in the prophylaxis and treatment of pain and inflammation associated with a variety of diseases and conditions. Such treatable pain includes visceral pain, neuropathic pain and hyperalgesia. Inflammation associated with conditions such as IBD and IBS, ocular and otic inflammation, other disorders and conditions such as pruritis, edema, hyponatremia, hypokalemia, ileus, tussis and glaucoma are treatable or preventable with the pharmaceutical compositions of the invention.

20 Claims, 8 Drawing Sheets

OTHER PUBLICATIONS

Samson, Isabelle et al., Screening a Random Pentapeptide Library, Composed of 14 D-Amino Acids, against the COOH-terminal Sequence of Fructose-1,6-bisphosphate Aldolase from *Trypanosoma brucei**, The Journal of Biological Chemistry, vol. 272, No. 17, Issue Apr. 25, pp. 11378-11383 (1997).

Schröder, E., Synthese des all-D-Val5-Angiotensin II-Asp1-β-amids, J. Liebigs Ann Chem, pp. 241—(1966).

Seo, Jeong Kon et al., A Peptide with Unique Receptor Specificity, Jimmunol, pp. 1895-1901 (1997).

Vanderah, T.W. et al., Mediation of Swim-Stress Antinociception by the Opioid Delta2 Receptor in the Mouse1, J. Pharm. Exper. Therapeutics, vol. 262:1 (1992).

Vogler, Von K. et al., Synthese von All-D-Val5-Angiotensin II-Asp1-β-Amid1), Helv Chim Acta, 48:6:152, pp. 1407-1414 (1965).

Vonvoigtlander, P.F. et al., U-50,488: A Selective and Structurally Novel Non-Mu (Kappa) Opioid Agonist, J. Pharm. Exper. Therapeutics, 224:7-12 (1983).

Wang, X. et al., Applications of topologically segregated bilayer beads in 'one-bead one-compound' combinatorial libraries, J. Peptide Res. 65, pp. 130-138 (2005).

Wisniewski, K. et al., Long Acting, Selective, Peripheral Kappa Agonists, J. Peptide Sci., 6 supp:S189 (2000) (Abstract).

Wisniewski, K. et al., Long Acting, Selective, Peripheral Kappa Agonists, Posters:1 Bioactive, P358 (Poster).

Wisniewski, K. et al., Long Acting, Selective, Peripheral Kappa Agonists, Peptides 2000:Proc. of 36th Eur Peptide Symp. (J. Martinez & J.A. Fehrentz, eds.) Editions EDK, pp. 775-776 (2001) (Mini-publication).

* cited by examiner

SYNTHETIC PEPTIDE AMIDES

RELATED APPLICATIONS

This application is a continuation of U.S. Ser. No. 12/176, 279 filed Jul. 18, 2008, now U.S. Pat. No. 7,727,963 B2 issued Jun. 1, 2010; which is a continuation of U.S. Ser. No. 11/938, 771 filed Nov. 12, 2007, now U.S. Pat. No. 7,402,564 B1 issued Jul. 22, 2008; which claims the benefit of U.S. provisional application Ser. No. 60/858,109, filed Nov. 10, 2006, and of U.S. provisional application Ser. No. 60/928,550, filed May 10, 2007, the specifications of each of these applications are expressly incorporated herein by reference in their entireties.

FIELD OF THE INVENTION

The invention relates to synthetic peptide amides incorporating D-amino acids in the peptide chain and more particularly to such synthetic peptide amides that are kappa opioid receptor agonists, and methods for their use as prophylactic and therapeutic agents.

BACKGROUND

Kappa opioid receptors have been suggested as targets for intervention for treatment or prevention of a wide array of diseases and conditions by administration of kappa opioid receptor agonists. See for example, Jolivalt et al., *Diabetologia*, 49(11):2775-85; Epub Aug. 19, 2006), describing efficacy of asimadoline, a kappa receptor agonist in rodent diabetic neuropathy; and Bileviciute-Ljungar et al., *Eur. J. Pharm.* 494:139-46 (2004) describing the efficacy of kappa agonist U-50,488 in the rat chronic constriction injury (CCI) model of neuropathic pain and the blocking of its effects by the opioid antagonist, naloxone. These observations support the use of kappa opioid receptor agonists for treatment of diabetic, viral and chemotherapy-induced neuropathic pain. The use of kappa receptor agonists for treatment or prevention of visceral pain including gynecological conditions such as dysmenorrheal cramps and endometriosis has also been reviewed. See for instance, Riviere, *Br. J. Pharmacol.* 141: 1331-4 (2004).

Kappa opioid receptor agonists have also been proposed for the treatment of pain, including hyperalgesia. Hyperalgesia is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors (Handwerker et al. (1991) *Proceeding of the VIth World Congress on Pain*, Bond et al., eds., Elsevier Science Publishers BV, pp. 59-70; Schaible et al. (1993) *Pain* 55:5-54). This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state. See for example, Woold et al. (1993) *Anesthesia and Analgesia* 77:362-79; Dubner et al. (1994) In, *Textbook of Pain*, Melzack et al., eds., Churchill-Livingstone, London, pp. 225-242.

Kappa opioid receptors have been suggested as targets for the prevention and treatment of cardiovascular disease. See for example, Wu et al. "Cardioprotection of Preconditioning by Metabolic Inhibition in the Rat Ventricular Myocyte—Involvement of kappa Opioid Receptor" (1999) *Circulation Res* vol. 84: pp. 1388-1395. See also Yu et al. "Anti-Arrhythmic Effect of kappa Opioid Receptor Stimulation in the Perfused Rat Heart: Involvement of a cAMP-Dependent Pathway" (1999) *J Mol Cell Cardiol.* vol. 31(10): pp. 1809-1819.

It has also been found that development or progression of these diseases and conditions involving neurodegeneration or neuronal cell death can be prevented, or at least slowed, by treatment with kappa opioid receptor agonists. This improved outcome is believed to be due to neuroprotection by the kappa opioid receptor agonists. See for instance, Kaushik et al. "Neuroprotection in Glaucoma" (2003) *J. Postgraduate Medicine* vol. 49 (1): pp. 90-95.

The presence of kappa opioid receptors on immune cells (Bidlak et al., (2000) *Clin. Diag. Lab. Immunol.* 7(5):719-723) has been implicated in the inhibitory action of a kappa opioid receptor agonist, which has been shown to suppress HIV-1 expression. See Peterson P K et al., *Biochem Pharmacol.* 2001, 61(19):1145-51.

Walker, *Adv. Exp. Med. Biol.* 521:148-60 (2003) appraised the anti-inflammatory properties of kappa agonists for treatment of osteoarthritis, rheumatoid arthritis, inflammatory bowel disease and eczema. Bileviciute-Ljungar et al., *Rheumatology* 45:295-302 (2006) describe the reduction of pain and degeneration in Freund's adjuvant-induced arthritis by the kappa agonist U-50,488.

Wikstrom et al., *J. Am. Soc. Nephrol.* 16:3742-7 (2005) describes the use of the kappa agonist, TRK-820 for treatment of uremic and opiate-induced pruritus, and Ko et al., *J. Pharmacol. Exp. Ther.* 305:173-9 (2003) describe the efficacy of U-50,488 in morphine-induced pruritus in the monkey.

Application of peripheral opioids including kappa agonists for treatment of gastrointestinal diseases has also been extensively reviewed. See for example, Lembo, *Diges. Dis.* 24:91-8 (2006) for a discussion of use of opioids in treatment of digestive disorders, including irritable bowel syndrome (IBS), ileus, and functional dyspepsia.

Ophthalmic disorders, including ocular inflammation and glaucoma have also been shown to be addressable by kappa opioids. See Potter et al., *J. Pharmacol. Exp. Ther.* 309:548-53 (2004), describing the role of the potent kappa opioid receptor agonist, bremazocine, in reduction of intraocular pressure and blocking of this effect by norbinaltorphimine (norBNI), the prototypical kappa opioid receptor antagonist; and Dortch-Carnes et al., *CNS Drug Rev.* 11(2):195-212 (2005). U.S. Pat. No. 6,191,126 to Gamache discloses the use of kappa opioid agonists to treat ocular pain. Otic pain has also been shown to be treatable by administration of kappa opioid agonists. See U.S. Pat. No. 6,174,878 also to Gamache.

Kappa opioid agonists increase the renal excretion of water and decrease urinary sodium excretion (i.e., produces a selective water diuresis, also referred to as aquaresis). Many, but not all, investigators attribute this effect to a suppression of vasopressin secretion from the pituitary. Studies comparing centrally acting and purportedly peripherally selective kappa opioids have led to the conclusion that kappa opioid receptors within the blood-brain barrier are responsible for mediating this effect. Other investigators have proposed to treat hyponatremia with nociceptin peptides or charged peptide conjugates that act peripherally at the nociceptin receptor, which is related to but distinct from the kappa opioid receptor (D. R. Kapusta, *Life Sci.*, 60:15-21, 1997) (U.S. Pat. No. 5,840,696). U.S. Pat Appl. 20060052284.

SUMMARY OF THE INVENTION

The present invention provides synthetic peptide amides having the formula of formula I below, and stereoisomers, mixtures of stereoisomers, prodrugs, pharmaceutically acceptable salts, hydrates, solvates, acid salt hydrates, N-oxides and isomorphic crystalline forms of the synthetic peptide amides of formula I:

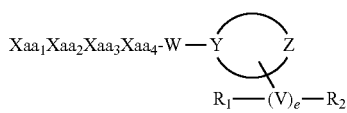

Formula I

In formula I, $Xaa_1$ represents an N-terminal amino acid that can be any of (A)(A')D-Phe, (A)(A')(α-Me)D-Phe, D-Tyr, D-1,2,3,4-tetrahydroisoquinoline-3 carboxylic acid, D-tert-leucine, D-neopentylglycine, D-phenylglycine, D-homophenylalanine, or β(E)D-Ala, wherein each (A) and each (A') are phenyl ring substituents independently chosen from —H, —F, —Cl, —$NO_2$, —$CH_3$, —$CF_3$, —CN, and —$CONH_2$, and wherein each (E) is independently chosen from the following substituents: cyclobutyl, cyclopentyl, cyclohexyl, pyridyl, thienyl and thiazolyl.

$Xaa_2$ is a second amino acid that can be any of (A)(A')D-Phe, 3,4-dichloro-D-Phe, (A)(A')(α-Me)D-Phe, D-1-naphthylalanine, D-2-naphthylalanine, D-Tyr, (E)D-Ala or D-Trp; wherein (A), (A') and (E) are each independently chosen from the substituents listed above for each of (A), (A') and (E).

$Xaa_3$ is a third amino acid that can be any of D-norleucine, D-Phe, (E)D-Ala, D-Leu, (α-Me)D-Leu, D-homoleucine, D-Val, or D-Met, wherein (E) is independently chosen from the substituents listed above for (E).

$Xaa_4$ is a fourth amino acid that can be any of $(B)_2$D-arginine, $(B)_2$D-norarginine, $(B)_2$D-homoarginine, ζ-(B)D-homolysine, D-2,3-diaminopropionic acid, ε-(B)D-Lys, ε-$(B)_2$-D-Lys, D-aminomethylphenylalanine, amidino-D-aminomethyl-phenylalanine, γ-$(B)_2$D-γ-diamino butyric acid, δ-$(B)_2$α-(B')D-Orn, D-2-amino-3(4-piperidyl)propionic acid, D-2-amino-3(2-aminopyrrolidyl)propionic acid, D-α-amino-β-amidinopropionic acid, α-amino-4-piperidineacetic acid, cis-α,4-diaminocyclohexane acetic acid, trans-α,4-diaminocyclo-hexaneacetic acid, cis-α-amino-4-methylamino cyclohexane acetic acid, trans-α-amino-4-methylaminocyclohexane acetic acid, α-amino-1-amidino-4-piperidine acetic acid, cis-α-amino-4-guanidinocyclohexane acetic acid, or trans-α-amino-4-guanidino-cyclohexane acetic acid, wherein each (B) is independently either —H or $C_1$-$C_4$ alkyl, and (B') is either —H or (α-Me).

The linking moiety, W can be any of the following three alternatives: (i) null, provided that when W is null, Y is N and is bonded to the C-terminus of $Xaa_4$ to form an amide; (ii) —NH—$(CH_2)_b$— with b equal to 0, 1, 2, 3, 4, 5, or 6; or (iii) —NH—$(CH_2)_c$—O— with c equal to 2, or 3, provided that Y is C. In each of the foregoing alternatives, (ii) and (iii) the N atom of W is bonded to the C-terminus of $Xaa_4$ to form an amide.

The moiety

in formula I is an optionally substituted 4 to 8-membered heterocyclic ring moiety wherein all ring heteroatoms in the ring moiety are N, and wherein Y and Z are each independently C or N. However, when this heterocyclic ring moiety is a six, seven or eight-membered ring, Y and Z must be separated by at least two ring atoms. Further, when this heterocyclic ring moiety has a single ring heteroatom which is N, then the ring moiety is non-aromatic.

The moiety V in formula I is $C_1$-$C_6$ alkyl. The operator, e is zero or 1, such that when e is zero, then V is null and $R_1$ and $R_2$ are directly bonded to the same or different ring atoms.

In the first of four alternative embodiments, the moiety $R_1$ in formula I can be any of the following groups: —H, —OH, halo, —$CF_3$, —$NH_2$, —COOH, $C_1$-$C_6$ alkyl, amidino, $C_1$-$C_6$ alkyl-substituted amidino, aryl, optionally substituted heterocyclyl, Pro-amide, Pro, Gly, Ala, Val, Leu, Ile, Lys, Arg, Orn, Ser, Thr, CN, $CONH_2$, COR', $SO_2$R', CONR'R", NHCOR', OR', or $SO_2$NR'R"; wherein the optionally substituted heterocyclyl is optionally singly or doubly substituted with substituents independently chosen from $C_1$-$C_6$ alkyl, $C_1$-$C_6$ alkoxy, oxo, —OH, —Cl, —F, —$NH_2$, —$NO_2$, —CN, —COOH, and amidino. The moieties R' and R" are each independently H, $C_1$-$C_8$ alkyl, aryl, or heterocyclyl. Alternatively, R' and R" can be combined to form a 4- to 8-membered ring, which ring is optionally substituted singly or doubly with substituents independently chosen from $C_1$-$C_6$ alkyl, $C_1$-$C_6$ alkoxy, —OH, —Cl, —F, —$NH_2$, —$NO_2$, —CN, —COOH and amidino. The moiety $R_2$ can be any of —H, amidino, singly or doubly $C_1$-$C_6$ alkyl-substituted amidino, —CN, —$CONH_2$, —CONR'R", —NHCOR', —$SO_2$NR'R", or —COOH.

In a second alternative embodiment, the moieties $R_1$ and $R_2$ taken together can form an optionally substituted 4- to 9-membered heterocyclic monocyclic or bicyclic ring moiety which is bonded to a single ring atom of the Y and Z-containing ring moiety.

In a third alternative embodiment, the moieties $R_1$ and $R_2$ taken together with a single ring atom of the Y and Z-containing ring moiety can form an optionally substituted 4- to 8-membered heterocyclic ring moiety to form a spiro structure.

In a fourth alternative embodiment, the moieties $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety.

In formula I, each of the optionally substituted 4-, 5-, 6-, 7-, 8- and 9-membered heterocyclic ring moieties comprising $R_1$ and $R_2$ can be singly or doubly substituted with substituents independently chosen from $C_1$-$C_6$ alkyl, $C_1$-$C_6$ alkoxy, optionally substituted phenyl, oxo, —OH, —Cl, —F, —$NH_2$, —$NO_2$, —CN, —COOH and amidino. Further, when the Y and Z-containing ring moiety of formula I is a six or seven-membered ring that has a single ring heteroatom, and e is zero, then $R_1$ cannot be —OH, and $R_1$ and $R_2$ are not both —H.

When the Y and Z-containing ring moiety in formula I is a six-membered ring in which there are two ring heteroatoms wherein both Y and Z are N, and W is null, then the moiety —$(V)_e R_1 R_2$ is attached to a ring atom other than Z. Moreover, under the foregoing conditions, if e is zero, then $R_1$ and $R_2$ cannot both be —H. Lastly, when $Xaa_3$ is D-Nle, then $Xaa_4$ cannot be $(B)_2$D-Arg; and when $Xaa_3$ is D-Leu or (αMe)D-Leu, then $Xaa_4$ cannot be δ-$(B)_2$α-(B')D-Orn.

The invention also provides a selective kappa opioid receptor agonist (interchangeably referred to herein as a kappa receptor agonist or simply as a kappa agonist) which is a synthetic peptide amide of the invention, as described above.

The invention also provides a pharmaceutical composition, which includes a synthetic peptide amide of the invention and a pharmaceutically acceptable diluent, excipient or carrier.

Also provided is a method of treating or preventing a kappa opioid receptor-associated disease or condition in a mammal. The method includes administering to the mammal a composition that includes an effective amount of a synthetic peptide amide of the invention. The invention also provides uses of the synthetic peptide amides of the invention for the preparation of medicaments and pharmaceutical compositions useful for the treatment of a kappa opioid receptor-associated disease or condition in a mammal.

The invention further provides a method of treating or preventing a kappa opioid receptor-associated disease or condition in a mammal, wherein a synthetic peptide amide of the invention is co-administered with a reduced dose of a mu opioid agonist analgesic compound to produce a therapeutic analgesic effect, the mu opioid agonist analgesic compound having an associated side effect, (especially respiratory depression, sedation, euphoria, antidiuresis, nausea, vomiting, constipation, and physical tolerance, dependence, and addiction). The reduced dose of the mu opioid agonist analgesic compound administered by this method has lower associated side effects than the side effects associated with the dose of the mu opioid agonist analgesic compound necessary to achieve the same therapeutic analgesic effect when administered alone.

The invention also provides a method of treating or preventing peripheral hyperalgesia, wherein the method includes topically applying or locally administering to a mammal in need of the treatment, an effective amount of a composition that includes an anti-hyperalgesically-effective amount of a synthetic peptide amide of the invention in a vehicle formulated for topical application or local administration.

The invention also provides a method of treating or preventing hyponatremia or hypokalemia, and thereby treating or preventing a disease or condition associated with hyponatremia or hypokalemia, such as congestive heart failure, liver cirrhosis, nephrotic syndrome, hypertension, or edema, and preferably where increased vasopressin secretion is associated with said disease or disorder, wherein the method includes administering to a mammal an aquaretically effective amount of a synthetic peptide amide of the invention in a pharmaceutically acceptable diluent, excipient or carrier.

DETAILED DESCRIPTION

Figure 1:
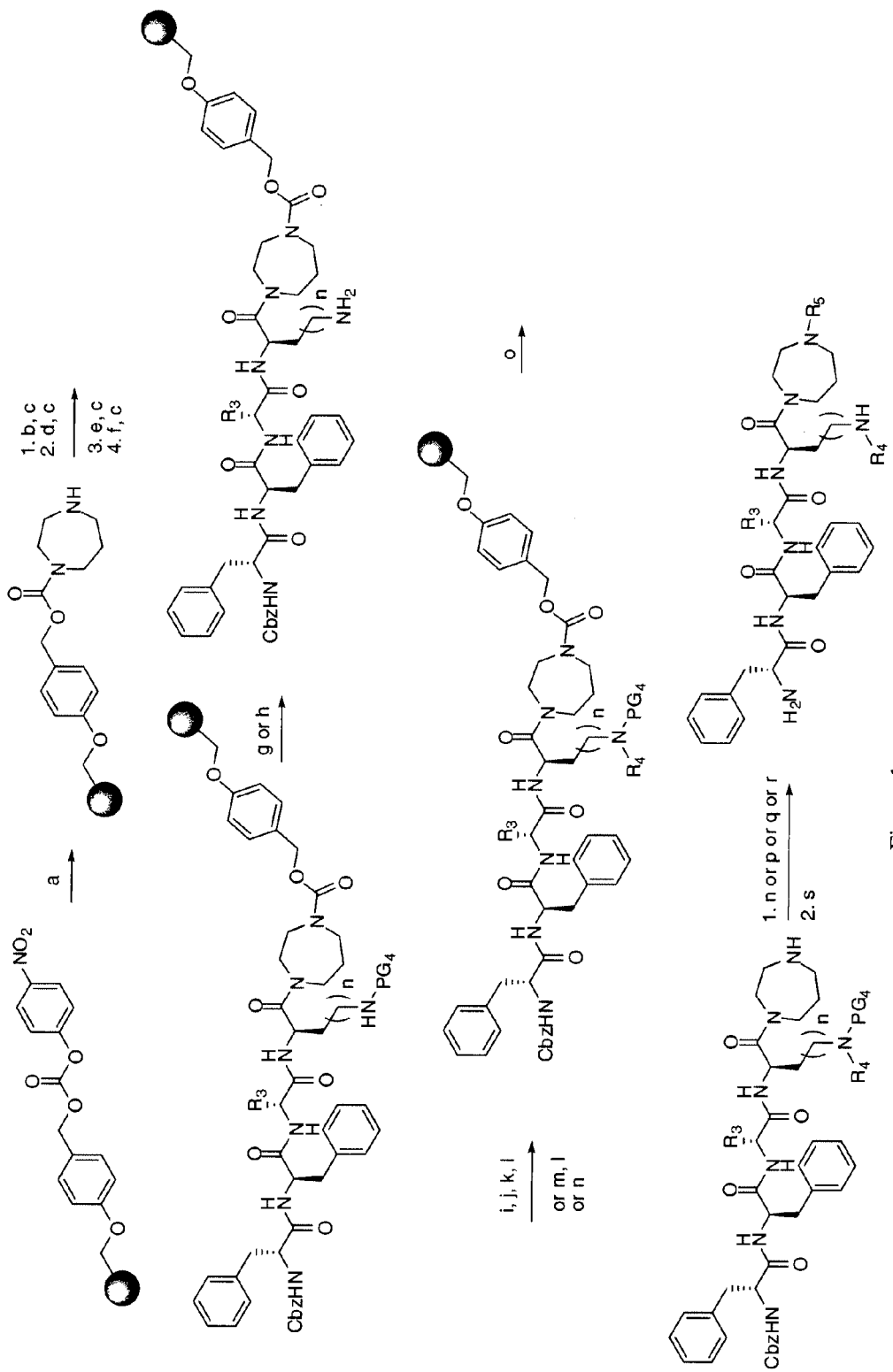
FIG. 1: Shows the general scheme used in the synthesis of compounds (1), (6), (7), (10) and (11). Steps a-s were carried out with the following reactants or conditions: a) homopiperazine, DCM; b) Fmoc-D-Dap(ivDde)-OH or Fmoc-D-Dab(ivDde)-OH or Fmoc-D-Orn(Aloc)-OH or Fmoc-D-Orn(Cbz)-OH or Fmoc-D-Lys(Dde)-OH or Fmoc-D-Arg(Pbf)-OH, DIC, HOBt, DMF; c) 25% piperidine in DMF; d) Fmoc-D-Leu-OH or Fmoc-D-Nle-OH, DIC, HOBt, DMF; e) Fmoc-D-Phe-OH, DIC, HOBt, DMF; f) Cbz-D-Phe-OH, DIC, HOBt, DMF; g) 4% hydrazine in DMF; h) Pd(PPh$_3$)$_4$, CHCl$_3$/AcOH/NMM; i) O-NBS-Cl, collidine, NMP; j) dimethylsulfate, DBU, NMR; k) mercaptoethanol, DBU, NMP; l) Cbz-OSu, DMF; m) acetone, AcOH, NaBH(OAc)$_3$, TMOF; n) 1H-pyrazole-1-carboxamidine, DIEA, DMF; o) 50% TFA/DCM; p) S-Methyl-N-methylisothio-urea hydroiodide, DIEA, DMF; q) 2-methylthio-2-imidazoline hydroiodide, DIEA, DMF; r) iodoethane, DIEA, DMF; s) TMSOTf/TFA/m-cresol.

As used throughout this specification, the term "synthetic peptide amide" means a compound of the invention conforming to formula I, or a stereoisomer, mixture of stereoisomers, prodrug, pharmaceutically acceptable salt, hydrate, solvate, acid salt hydrate, N-oxide or isomorphic crystalline form thereof. Where $Xaa_1$, $Xaa_2$, $Xaa_3$, and $Xaa_4$ specify D amino acids in compounds of the invention, stereoisomers of a compound of the invention conforming to formula I are limited to those compounds having amino acids in the D configuration where so specified in Formula I. Stereoisomers of the invention do include compounds having either D or L configuration at chiral centers other than the alpha carbons of the four amino acids $Xaa_1$, $Xaa_2$, $Xaa_3$, and $Xaa_4$. Mixtures of stereoisomers refer to mixtures of such stereoisomers of the invention. As used herein racemates refers to mixtures of stereoisomers having equal proportions of compounds with D and L configuration at one or more of the chiral centers other than the alpha carbons of $Xaa_1$, $Xaa_2$, $Xaa_3$, and $Xaa_4$ without varying the chirality of the alpha carbons of $Xaa_1$, $Xaa_2$, $Xaa_3$, and $Xaa_4$.

The nomenclature used to define peptides herein is specified by Schroder & Lubke, *The Peptides*, Academic Press, 1965, wherein, in accordance with conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" as in "D-Phe" which represents D-phenylalanine, the D-isomer of phenylalanine. Similarly, the L-isomer is specified by the prefix "L-" as in "L-Phe." Peptides are represented herein according to the usual convention as amino acid sequences from left to right: N-terminus to C-terminus, unless otherwise specified.

As used herein, D-Arg represents D-arginine, D-Har represents D-homoarginine, which has a side chain one methylene group longer than D-Arg, and D-Nar represents D-norarginine, which has a side chain one methylene group shorter than D-Arg. Similarly, D-Leu means D-leucine, D-Nle means D-norleucine, and D-Hle represents D-homoleucine. D-Ala means D-alanine, D-Tyr means D-tyrosine, D-Trp means D-tryptophan, and D-Tic means D-1,2,3,4-tetrahydroisoquinoline-3-carboxylic acid. D-Val means D-valine and D-Met means D-methionine. D-Pro means D-proline, Pro-amide means the D- or L-form of proline amide. D-Pro amide represents D-proline with an amide formed at its carboxy moiety wherein the amide nitrogen may be alkyl substituted, as in —$NR_aR_b$, wherein $R_a$ and $R_b$ are each independently a $C_1$-$C_6$ alkyl group, or one of $R_a$ and $R_b$ is —H. Gly means glycine, D-Ile means D-isoleucine, D-Ser means D-serine, and D-Thr means D-threonine. (E)D-Ala means the D-isomer of alanine which is substituted by the substituent (E) on the β-carbon. Examples of such substituent (E) groups include cyclobutyl, cyclopentyl, cyclohexyl, pyridyl, thienyl and thiazoyl. Thus, cyclopentyl-D-Ala means the D-isomer of alanine which is substituted by cyclopentyl on the β-carbon. Similarly, D-Ala(2-thienyl) and (2-thienyl)D-Ala are interchangeable and both mean the D-isomer of alanine substituted at the β-carbon with thienyl that is attached at the 2-ring position.

As used herein, D-Nal means the D-isomer of alanine substituted by naphthyl on the β-carbon. D-2Nal means naphthyl substituted D-alanine wherein the attachment to naphthalene is at the 2-position on the ring structure and D-1Nal means naphthyl-substituted D-alanine wherein the attachment to naphthalene is at the 1-position on the ring structure. By (A)(A')D-Phe is meant D-phenylalanine substituted on the phenyl ring with one or two substituents independently chosen from halo, nitro, methyl, halomethyl (such as, for example, trifluoromethyl), perhalomethyl, cyano and carboxamide. By D-(4-F)Phe is meant D-phenylalanine which is fluoro-substituted in the 4-position of the phenyl ring. By D-(2-F)Phe is meant D-phenylalanine which is fluoro-substituted in the 2-position of the phenyl ring. By D-(4-Cl)Phe is meant D-phenylalanine which is chloro substituted in the 4-phenyl ring position. By (α-Me)D-Phe is meant D-phenylalanine which is methyl substituted at the alpha carbon. By (α-Me)D-Leu is meant D-leucine which is methyl substituted at the alpha carbon.

The designations $(B)_2$D-Arg, $(B)_2$D-Nar, and $(B)_2$D-Har represent D-arginine, and D-norarginine D-homoarginine, respectively, each having two substituent (B) groups on the side chain. D-Lys means D-lysine and D-Hlys means D-homolysine. ζ-(B)D-Hlys, ε-(B)D-Lys, and ε-$(B)_2$-D-Lys represent D-homolysine and D-lysine each having the side chain amino group substituted with one or two substituent (B) groups, as indicated. D-Orn means D-ornithine and δ-(B)α-(B')D-Orn means D-ornithine substituted with (B') at the alpha carbon and substituted with (B) at the side chain δ-amino group.

D-Dap means D-2,3-diaminopropionic acid. D-Dbu represents the D-isomer of alpha, gamma-diamino butyric acid and $(B)_2$D-Dbu represents alpha, gamma-diamino butyric acid which is substituted with two substituent (B) groups at the gamma amino group. Unless otherwise stated, each of the (B) groups of such doubly substituted residues are independently chosen from H— and $C_1$-$C_4$-alkyl. As used herein, D-Amf means D-($NH_2CH_2$—)Phe, i.e., the D-isomer of phenylalanine substituted with aminomethyl on its phenyl ring and D-4Amf represents the particular D-Amf in which the aminomethyl is attached at the 4-position of the ring. D-Gmf means D-Amf(amidino) which represents D-Phe wherein the phenyl ring is substituted with —$CH_2NHC(NH)NH_2$. Amd represents amidino, —$C(NH)NH_2$, and the designations (Amd)D-Amf and D-Amf(Amd) are also interchangeably used for D-Gmf. The designations Ily and Ior are respectively used to mean isopropyl Lys and isopropyl Orn, wherein the side chain amino group is alkylated with an isopropyl group.

Alkyl means an alkane radical which can be a straight, branched, and cyclic alkyl group such as, but not limited to, methyl, ethyl, propyl, isopropyl, cyclopropyl, butyl, t-butyl, sec-butyl, pentyl, cyclopentyl, hexyl, cyclohexyl, cyclohexylethyl. $C_1$ to $C_8$ alkyl refers to alkyl groups having between one and eight carbon atoms. Similarly, $C_1$-$C_6$ alkyl refers to alkyl groups having between one and six carbon atoms. Likewise, $C_1$-$C_4$ alkyl refers to alkyl groups having between one and four carbon atoms. By lower alkyl is meant $C_1$-$C_6$ alkyl. Me, Et, Pr, Ipr, Bu, and Pn are interchangeably used to represent the common alkyl groups: methyl, ethyl, propyl, isopropyl, butyl, and pentyl, respectively. Although the linkage for an alkyl group is typically at one end of an alkyl chain, the linkage may be elsewhere in the chain, e.g. 3-pentyl which may also be referred to as ethylpropyl, or 1-ethylprop-1-yl. Alkyl-substituted, such as $C_1$ to $C_6$ alkyl-substituted amidino, indicates that the relevant moiety is substituted with one or more alkyl groups.

Where a specified moiety is null, the moiety is absent and if such moiety is indicated to be attached to two other moieties, such two other moieties are connected by one covalent bond. Where a connecting moiety is shown herein as attached to a ring at any position on the ring, and attached to two other moieties, such as $R_1$ and $R_2$, in the case where the connecting moiety is specified to be null, then the $R_1$ and $R_2$ moieties can each be independently attached to any position on the ring.

The terms "heterocycle", "heterocyclic ring" and "heterocyclyl" are used interchangeably herein and refer to a ring or ring moiety having at least one non-carbon ring atom, also called a heteroatom, which may be a nitrogen, a sulfur, or an oxygen atom. Where a ring is specified as having a certain number of members, the number defines the number of ring atoms without reference to any substituents or hydrogen atoms bonded to the ring atoms. Heterocycles, heterocyclic rings and heterocyclyl moieties can include multiple heteroatoms independently selected from nitrogen, sulfur, or oxygen atom in the ring. Rings may be substituted at any available position. For example, but without limitation, 6- and 7-membered rings are often substituted in the 4-ring position and 5-membered rings are commonly substituted in the 3-position, wherein the ring is attached to the peptide amide chain at the 1-ring position.

The term 'saturated' refers to an absence of double or triple bonds and the use of the term in connection with rings describes rings having no double or triple bonds within the ring, but does not preclude double or triple bonds from being present in substituents attached to the ring. The term "non-aromatic" refers in the context of a particular ring to an absence of aromaticity in that ring, but does not preclude the presence of double bonds within the ring, including double bonds which are part of an aromatic ring fused to the ring in question. Nor is a ring atom of a saturated heterocyclic ring moiety precluded from being double-bonded to a non-ring atom, such as for instance a ring sulfur atom being double-bonded to an oxygen atom substituent. As used herein, heterocycles, heterocyclic rings and heterocyclyl moieties also include saturated, partially unsaturated and heteroaromatic rings and fused bicyclic ring structures unless otherwise specified. A heterocycle, heterocyclic ring or heterocyclyl moiety can be fused to a second ring, which can be a saturated, partially unsaturated, or aromatic ring, which ring can be a heterocycle or a carbocycle. Where indicated, two substituents can be optionally taken together to form an additional ring. Rings may be substituted at any available position. A heterocycle, heterocyclic ring and heterocyclyl moiety can, where indicted, be optionally substituted at one or more ring positions with one or more independently selected substituents, such as for instance, $C_1$-$C_6$ alkyl, $C_3$-$C_8$ cycloalkyl, $C_1$-$C_6$ alkoxy, halo $C_1$-$C_6$ alkyl, optionally substituted phenyl, aryl, heterocyclyl, oxo, —OH, —Cl, —F, —NH$_2$, —NO$_2$, —CN, —COOH and amidino. Suitable optional substituents of the phenyl substituent include for instance, but without limitation, one or more groups selected from $C_1$-$C_3$ alkyl, $C_1$-$C_3$ alkoxy, halo $C_1$-$C_3$ alkyl, oxo, —OH, —Cl, —F, —NH$_2$, —NO$_2$, —CN, —COOH and amidino.

D-Phe and substituted D-Phe are examples of a suitable amino acid for residue Xaa$_1$ in Formula I. The phenyl ring can be substituted at any of the 2-, 3- and/or 4-positions. Particular examples of permitted substitutions include, for instance, chlorine or fluorine at the 2- or 4-positions. Also the alpha-carbon atom may be methylated. Other equivalent residues which represent conservative changes to D-Phe can also be used. These include D-Ala(cyclopentyl), D-Ala(thienyl), D-Tyr and D-Tic. The residue at the second position, Xaa$_2$ can also be D-Phe or substituted D-Phe with such substitutions including a substituent on the 4-position carbon of the phenyl ring, or on both the 3- and 4-positions. Alternatively, Xaa$_2$ can be D-Trp, D-Tyr or D-alanine substituted by naphthyl. The third position residue, Xaa$_3$ can be any non-polar amino acid residue, such as for instance, D-Nle, D-Leu, (α-Me)D-Leu, D-Hle, D-Met or D-Val. However, D-Ala(cyclopropyl, cyclobutyl, cyclopentyl or cyclohexyl) or D-Phe can also be used as Xaa$_3$. The fourth position residue Xaa$_4$ can be any positively charged amino acid residue, such as for instance, D-Arg and D-Har, which can be optionally substituted with lower alkyl groups, such as one or two ethyl groups. Alternatively, D-Nar and any other equivalent residues can be used, such as, for instance, D-Lys or D-Orn (either of which can be ω-amino group alkylated, for example by methyl or isopropyl groups, or methylated at the α-carbon group). Moreover, D-Dbu, D-4-Amf (which can be optionally substituted with amidino), and D-Hlys are also suitable amino acids at this position.

Compounds of the invention contain one or more chiral centers, each of which has two possible three-dimensional spatial arrangements (configurations) of the four substituents around the central carbon atom. These are known as stereoisomers, and more specifically as enantiomers (all chiral centers inverted) or diastereoisomers (two or more chiral centers, at least one chiral center remaining the same). In a specific embodiment of the invention, the amino acids which make up the tetrapeptide backbone, Xaa$_1$Xaa$_2$Xaa$_3$Xaa$_4$ are specified to be D-amino acids i.e., the opposite configuration to those generally found in mammals. Reference to stereoisomers of the synthetic peptide amides of the invention concerns chiral centers other than the alpha carbons of the D-amino acids which make up Xaa$_1$-Xaa$_4$. Thus, stereoisomers of synthetic peptide amides that are embodiments of the invention wherein each of Xaa$_1$-Xaa$_4$ are specified to be D-amino acids, do not include L-amino acids or racemic mixtures of the amino acids at these positions. Similarly, reference to racemates herein concerns a center other than the alpha carbons of the D-amino acids which make up Xaa$_1$-Xaa$_4$. Chiral centers in the synthetic peptide amides of the invention for which a stereoisomer may take either the R or S configuration include chiral centers in the moiety attached to the carboxy-terminus of Xaa$_4$, and also chiral centers in any amino acid side chain substituents of Xaa$_1$-Xaa$_4$.

The synthetic peptide amides of the invention described herein (also interchangeably referred to as synthetic peptide amide compounds, compounds of the invention, compound (number), or simply "the compounds") can be used or prepared in alternate forms. For example, many amino-containing compounds can be used or prepared as an acid salt. Often such salts improve isolation and handling properties of the compound. For example, depending on the reagents, reaction conditions and the like, compounds such as the synthetic peptide amides described herein can be used or prepared, for example, as the hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic synthetic peptide amides of the present invention may exist as zwitterions. All forms of these synthetic peptide amide compounds, including free acid, free base and zwitterions, are contemplated to be within the scope of the present invention. It is well known in the art that compounds containing both amino and carboxyl groups often exist in equilibrium with their zwitterionic forms. Thus, for any compound described herein that contains, for example, both amino and carboxyl groups, it will also be understood to include the corresponding zwitterion.

In certain embodiments the synthetic peptide amides of the invention conform to Formula I:

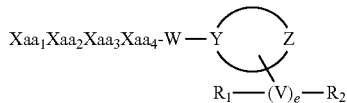

In such embodiments $Xaa_1$-$Xaa_2$-$Xaa_3$-$Xaa_4$ is a tetrapeptide moiety wherein $Xaa_1$ is the amino acid at the amino terminal, which can be (A)(A')D-Phe, (A)(A')(α-Me)D-Phe, D-Tyr, D-Tic, D-tert-leucine, D-neopentylglycine, D-phenylglycine, D-homophenylalanine, or β-(E)D-Ala, wherein each (A) and each (A') are phenyl ring substituents independently selected from —H, —F, —Cl, —$NO_2$, —$CH_3$, —$CF_3$, —CN, and —$CONH_2$, and (E) is selected from any of cyclobutyl, cyclopentyl, cyclohexyl, thienyl, pyridyl, or thiazolyl. The second amino acid in the tetrapeptide chain, $Xaa_2$, can be any of (A)(A')D-Phe, 3,4-dichloro-D-Phe, (A)(A')(α-Me)D-Phe, D-1Nal, D-2Nal, D-Tyr, (E)D-Ala or D-Trp. The third amino acid in the tetrapeptide chain, $Xaa_3$ can be D-Nle, D-Phe, (E)D-Ala, D-Leu, (α-Me)D-Leu, D-Hle, D-Val, or D-Met. The fourth amino acid in the tetrapeptide chain, $Xaa_4$ can be any of the following: $(B)_2$D-Arg, $(B)_2$D-Nar, $(B)_2$D-Har, ζ-(B)D-Hlys, D-Dap, ε-(B)D-Lys, ε-(B)-2-D-Lys, D-Amf, amidino-D-Amf, γ-$(B)_2$D-Dbu, δ-$(B)_2$α-(B')D-Orn, D-2-amino-3(4-piperidyl)propionic acid, D-2-amino-3(2-amino-pyrrolidyl)-propionic acid, D-α-amino-β-amidino-propionic acid, α-amino-4-piperidine acetic acid, cis-α,4-diaminocyclohexane acetic acid, trans-α,4-diaminocyclohexaneacetic acid, cis-α-amino-4-methylamino-cyclohexane acetic acid, trans-α-amino-4-methylamino cyclohexane acetic acid, α-amino-1-amidino-4-piperidine acetic acid, cis-α-amino-4-guanidinocyclohexane acetic acid, or trans-α-amino-4-guanidinocyclohexane acetic acid, wherein each (B) can be separately chosen from —H and a $C_1$-$C_4$ alkyl, and (B') can be —H or an (α-Me) group.

In certain embodiments of the invention, the optional linker group W is absent (i.e., null), provided that in such case, Y is N. In other embodiments, W is —N—$(CH_2)_b$ with b equal to zero, 1, 2, 3, 4, 5, or 6. In still other embodiments, W is —N—$(CH_2)_c$—O— with c equal to 2, or 3, provided that in such embodiments, Y is C.

In particular embodiments of the invention, the moiety

in formula I is an optionally substituted 4- to 8-membered heterocyclic ring moiety, wherein all ring heteroatoms in the ring moiety are N, and wherein Y and Z are each independently C or N, and are not adjacent ring atoms. In such embodiments, when this heterocyclic ring moiety is a six, seven or eight-membered ring, the ring atoms Y and Z are separated by at least two other ring atoms. In such embodiments, when this heterocyclic ring moiety has a single ring heteroatom which is N, the ring moiety is non-aromatic. In certain particular embodiments of the invention, a connecting moiety, V is directly bonded to the Y- and Z-containing ring. V is a $C_1$-$C_6$ alkyl which can be substituted with groups $R_1$ and $R_2$. The substituent $R_1$ can be any of —H, —OH, halo, —$CF_3$, —$NH_2$, —COOH, $C_1$-$C_6$ alkyl, amidino, $C_1$-$C_6$ alkyl-substituted amidino, aryl, optionally substituted heterocyclyl, Pro-amide, Pro, Gly, Ala, Val, Leu, Ile, Lys, Arg, Orn, Ser, Thr, —CN, —$CONH_2$, —COR', —$SO_2R'$, —CONR'R", —NHCOR', OR', or —$SO_2NR'R"$. The optionally substituted heterocyclyl can be singly or doubly substituted with substituents independently chosen from $C_1$-$C_6$ alkyl, $C_1$-$C_6$ alkoxy, oxo, —OH, —Cl, —F, —$NH_2$, —$NO_2$, —CN, —COOH, and amidino. The moieties R' and R" are each independently H, $C_1$-$C_8$ alkyl, aryl, or heterocyclyl. Alternatively, R' and R" can be combined to form a 4- to 8-membered ring, which ring is optionally substituted singly or doubly with substituents independently chosen from $C_1$-$C_6$ alkyl, $C_1$-$C_6$ alkoxy, —OH, —Cl, —F, —$NH_2$, —$NO_2$, —CN, —COOH, and amidino. The substituent $R_2$ can be any of —H, amidino, singly or doubly $C_1$-$C_6$ alkyl-substituted amidino, —CN, —$CONH_2$, —CONR'R", —NHCOR', —$SO_2NR'R"$, or —COOH.

In other particular embodiments, V is absent and the substituent groups $R_1$ and $R_2$ are directly bonded to the same or different ring atoms of the Y- and Z-containing heterocyclic ring.

In one alternative aspect of certain embodiments, the moieties $R_1$ and $R_2$ taken together can form an optionally substituted 4- to 9-membered heterocyclic monocyclic or bicyclic ring moiety which is bonded to a single ring atom of the Y and Z-containing ring moiety. In one particular embodiment, the moieties $R_1$ and $R_2$ form an optionally substituted 4- to 9-membered heterocyclic monocyclic or bicyclic ring moiety which is directly bonded to a single ring atom of the Y and Z-containing ring moiety.

In a second alternative aspect of certain embodiments, the moieties $R_1$ and $R_2$ taken together with a single ring atom of the Y and Z-containing ring moiety can form an optionally substituted 4- to 8-membered heterocyclic ring moiety to form a spiro structure.

In a third alternative aspect of certain embodiments, the moieties $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety.

In particular embodiments, each of the optionally substituted 4-, 5-, 6-, 7-, 8- and 9-membered heterocyclic ring moieties comprising $R_1$ and $R_2$ can be singly or doubly substituted with substituents independently chosen from $C_1$-$C_6$ alkyl, $C_1$-$C_6$ alkoxy, optionally substituted phenyl, oxo, —OH, —F, —$NH_2$, —$NO_2$, —CN, —COOH, and amidino. In certain particular embodiments, when the Y- and Z-containing ring moiety is a six or seven-membered ring that includes a single ring heteroatom, and when one of Y and Z is C and the other of Y and Z is N, and e is zero, then $R_1$ cannot be —OH, and $R_1$ and $R_2$ are not both —H. Further, when the Y and Z-containing ring moiety is a six-membered ring that includes two ring heteroatoms, wherein both Y and Z are N and W is null, then the moiety —$(V)_eR_1R_2$ is attached to a ring atom other than Z. Moreover, if e is zero, then $R_1$ and $R_2$ cannot both be —H. Lastly, when $Xaa_3$ is D-Nle, then $Xaa_4$ cannot be $(B)_2$D-Arg; and when $Xaa_3$ is D-Leu or (αMe)D-Leu, then $Xaa_4$ cannot be δ-$(B)_2$α-(B')D-Orn.

In certain embodiments, the present invention also provides a synthetic peptide amide having the formula:

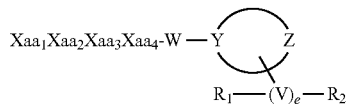

or a stereoisomer, racemate, prodrug, pharmaceutically acceptable salt, hydrate, solvate, acid salt hydrate, N-oxide or isomorphic crystalline form thereof; wherein $Xaa_1$ is selected from the group consisting of (A)(A')D-Phe, (α-Me)D-Phe, D-Tyr, D-Tic, D-phenylglycine, D-homophenylalanine, and β-(E)D-Ala, wherein (A) and (A') are each phenyl ring substituents independently selected from the group consisting of —H, —F, —Cl, —NO$_2$, —CH$_3$, —CF$_3$, —CN, and —CONH$_2$, and wherein (E) is selected from the group consisting of cyclobutyl, cyclopentyl, cyclohexyl, pyridyl, thienyl and thiazolyl; $Xaa_2$ is selected from the group consisting of (A)(A')D-Phe, (α-Me)D-Phe, D-1Nal, D-2Nal, D-Tyr, (E)D-Ala and D-Trp; $Xaa_3$ is selected from the group consisting of D-Nle, D-Phe, (E)D-Ala, D-Leu, (α-Me)D-Leu, D-Hle, D-Val, and D-Met; $Xaa_4$ is selected from the group consisting of (B)$_2$D-Arg, (B)$_2$D-nArg, (B)$_2$D-Har, D-Dap, ε-(B)D-Lys, ε-(B)$_2$-D-Lys, D-Amf, amidino-D-Amf, γ-(B)$_2$ D-Dbu, δ-(B)$_2$α-(B')D-Orn, D-2-amino-3(4-piperidyl)propionic acid, D-2-amino-3(2-aminopyrrolidyl)propionic acid, D-α-amino-β-amidinopropionic acid, (R)-α-amino-4-piperidineacetic acid, cis-α,4-diaminocyclohexane acetic acid, trans-α,4-diaminocyclohexaneacetic acid, cis-α-amino-4-methylaminocyclohexane acetic acid, trans-α-amino-4-methylaminocyclohexane acetic acid, α-amino-1-amidino-4-piperidineacetic acid, cis-α-amino-4-guanidinocyclohexane acetic acid, and trans-α-amino-4-guanidinocyclohexane acetic acid, wherein each (B) is independently selected from the group consisting of H and $C_1$-$C_4$ alkyl, and (B') is H or (α-Me). The group W is selected from the group consisting of: Null, provided that when W is null, Y is N;
—N—(CH$_2$)$_b$ with b equal to zero, 1, 2, 3, 4, 5, or 6; and
—N—(CH$_2$)$_c$—O— with c equal to 2, or 3, provided that Y is C;
and the moiety

is an optionally substituted 4-8 membered saturated mono- or dinitrogen heterocyclic ring moiety, wherein no ring atom other than Y and Z is a heteroatom, Y is C or N, Z is C or N, and at least one of Y and Z is N, and provided that in the case of a 4 or 5 membered heterocyclic ring, either Y or Z is C, and in the case of a dinitrogen heterocycle, Y and Z are separated by two or more ring carbon atoms;
V is $C_1$-$C_6$ alkyl, and e is zero or 1, wherein when e is zero, then V is null and $R_1$ and $R_2$ are directly bonded to the same or different ring atoms;
$R_1$ is H, OH, —NH$_2$, —COOH, $C_1$-$C_6$ alkyl, amidino, $C_1$-$C_6$ alkyl-substituted amidino, dihydroimidazole, Pro-amide, Pro, Gly, Ala, Val, Leu, Ile, Lys, Arg, Orn, Ser, Thr, —CN, —CONH$_2$, —CONR'R", —NHCOR', —OR', or —SO$_2$NR'R", wherein R' and R" are each independently H, or $C_1$-$C_8$ alkyl, or R' and R" are combined to form a 4- to 8-membered ring which ring is optionally substituted singly or doubly with substituents independently selected from the group consisting of $C_1$-$C_6$ alkyl, $C_1$-$C_6$ alkoxy, —OH, —Cl, —F, —NH$_2$, —NO$_2$, —CN, and —COOH, amidino; and $R_2$ is H, amidino, singly or doubly $C_1$-$C_6$ alkyl-substituted amidino, —CN, —CONH$_2$, —CONR'R", —NHCOR', —SO$_2$NR'R", or —COOH; provided that when the Y and Z-containing ring moiety is a six or seven membered ring and when one of Y and Z is C and e is zero, then $R_1$ is not OH, and $R_1$ and $R_2$ are not both H; provided that when the Y and Z-containing ring moiety is a six membered ring, both Y and Z are N and W is null, then —(V)$_e$R$_1$R$_2$ is attached to a ring atom other than Z; and if e is zero, then $R_1$ and $R_2$ are not both —H; and lastly, provided that when $Xaa_3$ is D-Nle, then $Xaa_4$ cannot be (B)$_2$D-Arg, and when $Xaa_3$ is D-Leu or (αMe)D-Leu, then $Xaa_4$ cannot be δ-(B)$_2$α-(B')D-Orn.

In one embodiment, the present invention provides a synthetic peptide amide of formula I, wherein $Xaa_1Xaa_2$ is D-Phe-D-Phe, $Xaa_3$ is D-Leu or D-Nle and $Xaa_4$ is chosen from (B)$_2$D-Arg, D-Lys, (B)$_2$D-Har, D-Dap, ε-(B)D-Lys, ε-(B)$_2$-D-Lys, D-Amf, amidino-D-Amf, γ-(B)$_2$D-Dbu and δ-(B)$_2$α-(B')D-Orn. In a particular aspect of the above embodiment, $Xaa_4$ is chosen from D-Lys, (B)$_2$D-Har, ε-(B)D-Lys, and ε-(B)$_2$-D-Lys.

In another embodiment, the invention provides a synthetic peptide amide of formula I, wherein W is null, Y is N and Z is C. In a particular aspect of the above embodiment, the Y and Z-containing ring moiety is a six-membered saturated ring comprising a single ring heteroatom.

In another embodiment, the invention provides a synthetic peptide amide of formula I, wherein Y and Z are both N and are the only ring heteroatoms in the Y and Z-containing ring moiety.

In another embodiment, when the Y- and Z-containing ring moiety is a saturated six-membered ring that includes two ring heteroatoms and W is null, then Z is a carbon atom.

In yet another embodiment, the invention provides a synthetic peptide amide of formula I, wherein $R_1$ and $R_2$ taken together with zero, one or two ring atoms of the Y and Z-containing ring moiety comprise a monocyclic or bicyclic 4-9 membered heterocyclic ring moiety. In a particular aspect of the above embodiment, $R_1$ and $R_2$ taken together with one ring atom of the Y and Z-containing ring moiety comprise a 4- to 8-membered heterocyclic ring moiety which with the Y and Z-containing ring moiety forms a spiro structure and W is null.

In still another embodiment, the invention provides a synthetic peptide amide of formula I, wherein e is zero and $R_1$ and $R_2$ are bonded directly to the same ring carbon atom.

In a further embodiment, the invention provides a synthetic peptide amide of formula I, wherein $R_1$ is H, OH, —NH$_2$, —COOH, —CH$_2$COOH, $C_1$-$C_3$ alkyl, amidino, $C_1$-$C_3$ alkyl-substituted amidino, dihydroimidazole, D-Pro, D-Pro amide, or —CONH$_2$ and wherein $R_2$ is H, —COOH, or $C_1$-$C_3$ alkyl.

In another embodiment, the invention provides a synthetic peptide amide of formula I, wherein the moiety:

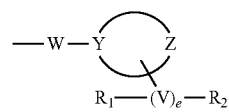

is selected from the group consisting of:

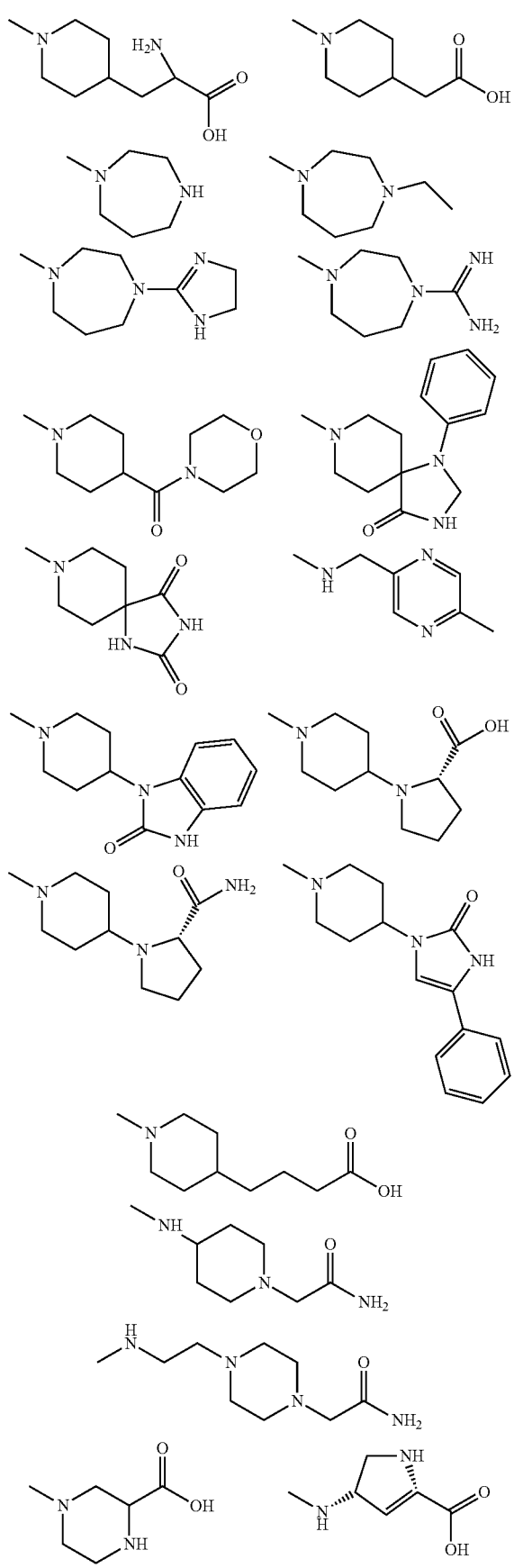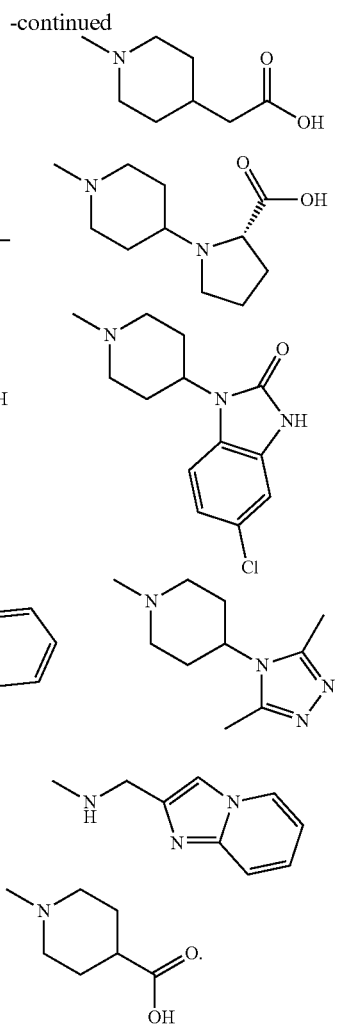

and

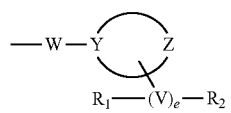

In still yet another embodiment, the invention provides a synthetic peptide amide of formula I wherein the moiety:

$$-W-Y\stackrel{Z}{\underset{R_1-(V)_e-R_2}{\bigcirc}}$$

is neither a proline moiety, nor a substituted proline moiety, nor is it a proline moiety wherein $R_1$ or $R_2$ contains an amide moiety.

In still yet another embodiment, the invention provides a synthetic peptide amide of formula I, wherein it is provided that when W is null, the Y and Z-containing ring moiety is a saturated 5-membered ring with only a single ring heteroatom, e is zero and either $R_1$ or $R_2$ is attached to a ring carbon adjacent to Y, then $R_1$ is selected from the group consisting of —H, —OH, halo, —$CF_3$, —$NH_2$, $C_1$-$C_6$ alkyl, amidino, $C_1$-$C_6$ alkyl-substituted amidino, aryl, Pro, Gly, Ala, Val, Leu, Ile, Lys, Arg, Orn, Ser, Thr, CN, —$SO_2R'$, —NHCOR', —OR' and —$SO_2NR'R''$ and $R_2$ is selected from the group consisting of —H, amidino, singly or doubly $C_1$-$C_6$ alkyl-substituted amidino, —CN, —NHCOR', and —$SO_2NR'R''$.

In still yet another embodiment, the invention provides a synthetic peptide amide of formula I having an $EC_{50}$ of less than about 500 nM for a kappa opioid receptor. In a particular aspect, the synthetic peptide amide can have an $EC_{50}$ of less than about 100 nM for a kappa opioid receptor. In a more particular aspect, the synthetic peptide amide can have an $EC_{50}$ of less than about 20 nM for a kappa opioid receptor. In most particular aspect, the synthetic peptide amide can have an $EC_{50}$ of less than about 1 nM for a kappa opioid receptor. The compounds of the foregoing embodiment can have an $EC_{50}$ that is at least 10 times greater for a mu and a delta opioid receptor than for a kappa opioid receptor, preferably at least 100 times greater, and most preferably at least 1000 times greater (e.g., an $EC_{50}$ of less than about 1 nM for a kappa opioid receptor, and $EC_{50}$ values of greater than about 1000 nM for a mu opioid receptor and a delta opioid receptor).

In still yet another embodiment, the invention provides a synthetic peptide amide of formula I which at an effective concentration exhibits no more than about 50% inhibition of any of $P_{450}$ CYP1A2, CYP2C9, CYP2C19 or CYP 2D6 by the synthetic peptide amide at a concentration of 10 uM after 60 minutes incubation with human liver microsomes.

In still a further embodiment, the invention provides a synthetic peptide amide of formula I, which at a dose of about 3 mg/kg in rat reaches a peak plasma concentration of the synthetic peptide amide that is at least about five fold higher than the peak concentration in brain. In one particular aspect of the above embodiment, the synthetic peptide amide has an $ED_{50}$ for a sedative effect in a locomotion-reduction assay in a mouse at least about ten times the $ED_{50}$ of the synthetic peptide amide for an analgesic effect in a writhing assay in a mouse.

In still a further embodiment, the invention provides a synthetic peptide amide of formula I having at least about 50% of maximum efficacy at about 3 hours post administration of a dose of about 3 mg/kg of the synthetic peptide amide in a rat.

In one embodiment, the invention provides a pharmaceutical composition that includes a synthetic peptide amide of formula I and a pharmaceutically acceptable excipient or carrier.

In another embodiment, the invention provides a method of treating or preventing a kappa opioid receptor-associated disease or condition in a mammal; the method includes administering to the mammal a composition comprising an effective amount of a synthetic peptide amide according to formula I sufficient to treat or prevent the kappa opioid receptor-associated disease or condition.

A variety of assays may be employed to test whether the synthetic peptide amides of the invention exhibit high affinity and selectivity for the kappa opioid receptor, long duration of in vivo bioactivity, and lack of CNS side effects. Receptor assays are well known in the art and kappa opioid receptors from several species have been cloned, as have mu and delta opioid receptors. Kappa opioid receptors as well as mu and delta opioid receptors are classical, seven transmembrane-spanning, G protein-coupled receptors. Although these cloned receptors readily allow a particular candidate compound, e.g., a peptide or peptide derivative, to be screened, natural sources of mammalian opioid receptors are also useful for screening, as is well known in the art (Dooley C T et al. Selective ligands for the mu, delta, and kappa opioid receptors identified from a single mixture based tetrapeptide positional scanning combinatorial library. *J. Biol. Chem.* 273: 18848-56, 1998). Thus, screening against both kappa and mu opioid receptors, whether of recombinant or natural origin, may be carried out in order to determine the selectivity of the synthetic peptide amides of the invention for the kappa over the mu opioid receptor.

In a particular embodiment, the synthetic peptide amides of the invention are selective kappa opioid receptor agonists. The potency of the synthetic peptide amides of the invention as agonists for a particular receptor can be measured as a concentration at which half maximal effect is achieved expressed as an $EC_{50}$ value. Potency of the synthetic peptide amides of the invention as kappa opioid agonists, expressed as the percent of maximal observable effect, can be determined by a variety of methods well known in the art. See for example, Endoh T et al., 1999, Potent Antinociceptive Effects of TRK-820, a Novel κ-Opioid Receptor Agonist, *Life Sci.* 65 (16) 1685-94; and Kumar V et al., Synthesis and Evaluation of Novel peripherally Restricted κ-Opioid Receptor Agonists, 2005 *Bioorg Med Chem Letts* 15: 1091-1095.

Examples of such assay techniques for determination of $EC_{50}$ values are provided below. Many standard assay methods for characterization of opioid ligands are well known to those of skill in the art. See, for example, Waldhoer et al., (2004) Ann. Rev. Biochem. 73:953-990, and Satoh & Minami (1995) Pharmac. Ther. 68(3):343-364 and references cited therein.

In certain particular embodiments, the synthetic peptide amides of the invention are kappa opioid receptor agonists with an $EC_{50}$ of less than about 500 nM. In other embodiments, the synthetic peptide amides have an $EC_{50}$ of less than about 100 nM as kappa opioid receptor agonists. In still other embodiments, the synthetic peptide amides have an $EC_{50}$ of less than about 10 nM as kappa opioid receptor agonists. In particular embodiments the synthetic peptide amides of the invention have an $EC_{50}$ of less than about 1.0 nM, less than about 0.1 nM, or less than about 0.1 nM, or even less than about 0.01 nM as kappa opioid receptor agonists.

In particular embodiments, the synthetic peptide amides of the invention are highly selective for kappa over mu opioid receptors. In certain embodiments the synthetic peptide amides of the invention have $EC_{50}$ values for the mu opioid receptor that are at least about a hundred times higher than the corresponding $EC_{50}$ values for the kappa opioid receptor. In particular embodiments, the synthetic peptide amides of the invention have $EC_{50}$ values for the mu opioid receptor that are at least about a thousand times higher than the corresponding $EC_{50}$ values for the kappa opioid receptor. Alternatively, the selectivity of the synthetic peptide amides of the invention can be expressed as a higher $EC_{50}$ for a mu opioid receptor than for a kappa opioid receptor. Thus, in particular embodiments, the synthetic peptide amides of the invention have $EC_{50}$ values of greater than about 10 uM for the mu opioid receptor and $EC_{50}$ values of less than about 10 nM, and in other embodiments less than about 1.0 nM, or even less than about 0.01 nM for the kappa opioid receptor. In another embodiment, the particular synthetic peptide amide can have an $EC_{50}$ of less than about 1 nM for a kappa opioid receptor and an $EC_{50}$ of greater than about 1000 nM for a mu opioid receptor, or for a delta opioid receptor.

Another property of the synthetic peptide amides of the invention is their characteristic property of low inhibition of the cytochrome $P_{450}$ isozymes. The cytochrome $P_{450}$ isozymes constitute a large superfamily of haem-thiolate proteins responsible for metabolic oxidative inactivation of many therapeutics and other bioactive compounds. Usually, they act as terminal oxidases in multicomponent electron transfer chains, also referred to as cytochrome $P_{450}$-containing monooxygenase systems.

Over fifty different cytochrome $P_{450}$ isozymes have been identified and have been classified into families grouped by genetic relatedness as assessed by nucleic acid sequence homology. Most abundant among the cytochrome $P_{450}$ isozymes in human cells are the 1A2 and 3A4 isozymes, although isozymes 2B6, 2C9, 2C19, 2D6, and 2E1 also contribute significantly to oxidative inactivation of administered therapeutics. While inhibition of the cytochrome $P_{450}$ isozymes may be useful in prolonging the time post in vivo administration during which an effective concentration of the synthetic peptide amides of the invention is maintained, it also prolongs the persistence of any co-administered therapeutic compound that is subject to oxidation by cytochrome $P_{450}$. This increase in persistence may cause the co-administered therapeutic to persist beyond the period that is optimal for therapy, or may cause the in vivo concentration to exceed the desired levels or safely tolerated levels. Such increases in persistence and/or increases in concentration are difficult to accurately quantify and are preferably avoided. Therapeutics that show little or no inhibition of the activity of the cytochrome $P_{450}$ isozymes do not have this potential problem and can be more safely co-administered with other therapeutics without risk of affecting the rate of inactivation of the co-administered therapeutic compound by the cytochrome $P_{450}$ isozymes.

Particular embodiments of the synthetic peptide amides of the invention show low inhibition of the cytochrome $P_{450}$ isozymes at therapeutic concentrations of the synthetic peptide amides, while others show essentially no inhibition of the cytochrome $P_{450}$ isozymes at therapeutic concentrations. In some embodiments, the synthetic peptide amides at a concentration of 10 uM show less than about 50% inhibition of cytochrome $P_{450}$ isozymes CYP1A2, CYP2C9, CYP2C19 or CYP2D6. In particular embodiments, the synthetic peptide amides at a concentration of 10 uM show less than about 20% inhibition of any of these cytochrome $P_{450}$ isozymes. In very particular embodiments, the synthetic peptide amides at a concentration of 10 uM show less than about 10% inhibition of any of these cytochrome $P_{450}$ isozymes.

In another embodiment, the synthetic peptide amides of the invention at an effective concentration exhibit no more than about 50% inhibition of any of $P_{450}$ CYP1A2, CYP2C9, CYP2C19 or CYP 2D6 by the synthetic peptide amide at a concentration of 10 uM after 60 minutes incubation with human liver microsomes.

The synthetic peptide amides of the invention when administered to a mammal or a human patient at a therapeutically effective concentration exhibit low or essentially no penetration across the blood-brain barrier. Kappa opioid receptors (hereinafter interchangeably referred to as kappa receptors) are distributed in peripheral tissues including the skin and somatic tissues, as well as the viscera in humans and other mammals. Kappa receptors are also found in the brain. Activation of the kappa receptors in peripheral tissues causes suppression of pain and inflammatory responses, while activation of the kappa receptors in the brain causes sedative effects and may also lead to severe dysphoria and hallucinations. In certain embodiments, the synthetic peptide amide of the invention when administered at therapeutically effective concentrations exhibit essentially no penetration across the blood-brain barrier and therefore minimize or even completely obviate the sedative, hallucinogenic effects of many other kappa agonists that show some penetration across the blood-brain barrier.

One useful measure of the extent to which the synthetic peptide amides of the invention cross the blood-brain barrier is the ratio of the peak plasma concentration to the concentration in brain tissue. In particular embodiments, the synthetic peptide amides of the invention when administered at dose of about 3 mg/kg, exhibit at least about a five fold lower concentration of the synthetic peptide amide in brain than in plasma at the time when peak plasma concentration is reached.

Another useful measure of the extent to which the synthetic peptide amides of the invention cross the blood-brain barrier is the ratio of the dose required to achieve a sedative effect and the dose required to achieve an analgesic effect. The analgesic and sedative effects of kappa receptor stimulation by kappa receptor agonists can be measured by standard assays well known to those of skill in the art.

In particular embodiments, the synthetic peptide amides of the invention have an $ED_{50}$ for a sedative effect that is at least about ten times the $ED_{50}$ for an analgesic effect. In particular embodiments, the synthetic peptide amides of the invention have an $ED_{50}$ for a sedative effect that is at least about thirty times the $ED_{50}$ for an analgesic effect. In still other embodiments, the synthetic peptide amides of the invention have an $ED_{50}$ for a sedative effect that is at least about fifty times the $ED_{50}$ for an analgesic effect.

In another embodiment, the synthetic peptide amides of the invention have an $ED_{50}$ for a sedative effect in a locomotion-reduction assay in a mouse at least about ten times the $ED_{50}$ of the synthetic peptide amide for an analgesic effect in a writhing assay in a mouse.

Another useful predictor of the extent to which the synthetic peptide amides of the invention would be expected to cross the blood-brain barrier is provided by the membrane permeability values of the synthetic peptide amides into a human cell or other mammalian cell when delivered at a therapeutically relevant concentration. In certain embodiments, the synthetic peptide amides of the invention at therapeutically relevant concentrations exhibit low or essentially no ability to penetrate a monolayer of suitably cultured human or other mammalian cells. This permeability parameter can be expressed as an apparent permeability, $P_{app}$, representing the permeability of the particular cell monolayer to a compound of interest. Any suitably culturable mammalian cell monolayer can be used to determine its permeability for a particular compound of interest, although certain cell lines are frequently used for this purpose. For instance, the Caco-2 cell line is a human colon adenocarcinoma that can be used as a monolayer culture test system for determination of membrane permeability towards compounds of the invention. In certain embodiments, the synthetic peptide amides of the invention have a $P_{app}$ of less than about $10^{-6}$ cm/sec. In certain other embodiments, the synthetic peptide amides of the invention have a $P_{app}$ of less than about $10^{-7}$ cm/sec.

In one embodiment, the synthetic peptide amides of the invention at a dose of about 3 mg/kg in rat reaches a peak plasma concentration of the synthetic peptide amide and exhibits at least about a five fold lower concentration in brain than such peak plasma concentration.

In another embodiment, the synthetic peptide amides of the invention have at least about 50% of maximum efficacy at about 3 hours post administration of a dose of about 3 mg/kg of the synthetic peptide amide in a rat.

In one embodiment the synthetic peptide amide of the invention exhibits a long lasting duration of action in a mammal, such as a human. In one aspect, the synthetic peptide amide has a duration of action that is at least about 50% of maximum efficacy at 3 hrs post administration of 0.1 mg/kg of the synthetic peptide amide. In another aspect the synthetic peptide amide has a duration of action that is at least about 75% of maximum efficacy at 3 hrs post administration of 0.1 mg/kg of the synthetic peptide amide. In a particular aspect the synthetic peptide amide has a duration of action is at least about 90% of maximum efficacy at 3 hrs post administration of 0.1 mg/kg of the synthetic peptide amide. In a specific aspect, the synthetic peptide amide has a duration of action is at least about 95% of maximum efficacy at 3 hrs post administration of 0.1 mg/kg of the synthetic peptide amide.

In another embodiment, the invention provides a pharmaceutical composition that includes a synthetic peptide amide according to any of the above embodiments and a pharmaceutically acceptable excipient or carrier. The invention provides methods, compositions, or dosage forms that employ and/or contain synthetic peptide amides of the invention that are selective for the kappa opioid receptor. In particular embodiments, the synthetic peptide amides of the invention exhibit a strong affinity for the kappa opioid receptor and have a high potency as kappa opioid receptor agonists.

A pro-drug of a compound such as the synthetic peptide amides of the invention include pharmaceutically acceptable derivatives which upon administration can convert through metabolism or other process to a biologically active form of the compound. Pro-drugs are particularly desirable where the pro-drug has more favorable properties than does the active compound with respect to bioavailability, stability or suitability for a particular formulation.

As used herein, a kappa opioid receptor-associated disease, condition or disorder is any disease, condition or disorder that is preventable or treatable by activation of a kappa opioid receptor. In one aspect, the synthetic peptide amides of the invention are kappa opioid receptor agonists that activate the kappa opioid receptor. In some embodiments, a particular dose and route of administration of the synthetic peptide amide of the invention can be chosen by a clinician to completely prevent or cure the disease, condition or disorder. In other embodiments a particular dose and route of administration of the synthetic peptide amide of the invention chosen by the clinician ameliorates or reduce one or more symptoms of the disease, condition or disorder.

As used herein, "effective amount" or "sufficient amount" of the synthetic peptide amide of the invention refers to an amount of the compound as described herein that may be therapeutically effective to inhibit, prevent or treat a symptom of a particular disease, disorder, condition, or side effect. As used herein, a "reduced dose" of a mu opioid agonist analgesic compound refers to a dose which when used in combination with a kappa opioid agonist, such as a synthetic peptide amide of the invention, is lower than would be ordinarily provided to a particular patient, for the purpose of reducing one or more side effects of the compound. The dose reduction can be chosen such that the decrease in the analgesic or other therapeutic effect of the compound is an acceptable compromise in view of the reduced side effect(s), where said decrease in said analgesic or other therapeutic effects of the mu opioid agonist analgesic are at least partially, and most preferably wholly, offset by the analgesic or other therapeutic effect of a synthetic peptide amide of the invention. Co-administration of a mu opioid agonist analgesic compound with a synthetic peptide amide of the invention which acts as a kappa opioid agonist also permits incorporation of a reduced dose of the synthetic peptide amide and/or the mu opioid agonist analgesic compound to achieve the same therapeutic effect as a higher dose of the synthetic peptide amide or the mu opioid agonist analgesic compound If administered alone.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit to-risk ratio that is reasonable for the medical condition being treated.

As used herein, "dosage unit" refers to a physically discrete unit suited as unitary dosages for a particular individual or condition to be treated. Each unit may contain a predetermined quantity of active synthetic peptide amide compound(s) calculated to produce the desired therapeutic effect(s), optionally in association with a pharmaceutical carrier. The specification for the dosage unit forms may be dictated by (a) the unique characteristics of the active compound or compounds, and the particular therapeutic effect to be achieved, and (b) the limitations inherent in the art of compounding such active compound or compounds. The dosage unit is often expressed as weight of compound per unit body weight, for instance, in milligrams of compound per kilogram of body weight of the subject or patient (mg/kg). Alternatively, the dosage can be expressed as the amount of the compound per unit body weight per unit time, (mg/kg/day) in a particular dosage regimen. In further alternatives, the dosage can be expressed as the amount of compound per unit body surface area ($mg/m^2$) or per unit body surface area per unit time ($mg/m^2/day$). For topical formulations, the dosage can be expressed in a manner that is conventional for that formulation, e.g., a one-half inch ribbon of ointment applied to the eye, where the concentration of compound in the formulation is expressed as a percentage of the formulation.

As used herein, "pharmaceutically acceptable salts" refers to derivatives of compounds wherein the parent compound is modified by making acid or base salts thereof. Examples of pharmaceutically acceptable salts include, but are not limited to, mineral or organic acid salts of basic residues such as amines, alkali or organic salts of acidic residues, such as carboxylic acids, and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a synthetic peptide amide can be formed from any such peptide amide having either acidic, basic or both functional groups. For example, a peptide amide having a carboxylic acid group, may in the presence of a pharmaceutically suitable base, form a carboxylate anion paired with a cation such as a sodium or potassium cation. Similarly, a peptide amide having an amine functional group may, in the presence of a pharmaceutically suitable acid such as HCl, form a salt.

One example of a pharmaceutically acceptable solvate of a synthetic peptide amide is a combination of a peptide amide with solvent molecules which yields a complex of such solvent molecules in association with the peptide amide. Particularly suitable hydrates of compounds are such hydrates which either have comparable activity or hydrates which are converted back to the active compound following administration. A pharmaceutically acceptable N-oxide of a synthetic peptide amide which contains an amine is such a compound wherein the nitrogen atom of the amine is bonded to an oxygen atom.

A pharmaceutically acceptable crystalline, isomorphic crystalline or amorphous form of a synthetic peptide amide of the invention can be any crystalline or non-crystalline form of a pharmaceutically acceptable acidic, basic, zwitterionic, salt, hydrate or any other suitably stable, physiologically compatible form of the synthetic peptide amide according to the invention.

The synthetic peptide amides of the invention can be incorporated into pharmaceutical compositions. The compositions can include an effective amount of the synthetic peptide amide in a pharmaceutically acceptable diluent, excipient or carrier. Conventional excipients, carriers and/or diluents for use in pharmaceutical compositions are generally inert and make up the bulk of the preparation.

In a particular embodiment, the synthetic peptide amide is a kappa opioid receptor agonist. In another embodiment, the synthetic peptide amide is a selective kappa opioid receptor agonist. The target site can be a kappa receptor in the patient or subject in need of such treatment or preventative. Certain synthetic peptide amide kappa opioid receptor agonists of the invention are peripherally acting and show little or no CNS effects at therapeutically effective doses.

The pharmaceutical excipient or carrier can be any compatible, non-toxic substance suitable as a vehicle for delivery the synthetic peptide amide of the invention. Suitable excipients or carriers include, but are not limited to, sterile water (preferably pyrogen-free), saline, phosphate-buffered saline (PBS), water/ethanol, water/glycerol, water/sorbitol, water/polyethylene glycol, propylene glycol, cetylstearyl alcohol, carboxymethylcellulose, corn starch, lactose, glucose, microcrystalline cellulose, magnesium stearate, polyvinylpyrrolidone (PVP), citric acid, tartaric acid, oils, fatty substances, waxes or suitable mixtures of any of the foregoing.

The pharmaceutical composition according to the invention can be formulated as a liquid, semisolid or solid dosage form. For example the pharmaceutical composition can be in the form of a solution for injection, drops, syrup, spray, suspension, tablet, patch, capsule, dressing, suppository, ointment, cream, lotion, gel, emulsion, aerosol or in a particulate form, such as pellets or granules, optionally pressed into tablets or lozenges, packaged in capsules or suspended in a liquid. The tablets can contain binders, lubricants, diluents, coloring agents, flavoring agents, wetting agents and may be enteric-coated to survive the acid environment of the stomach and dissolve in the more alkaline conditions of the intestinal lumen. Alternatively, the tablets can be sugar-coated or film coated with a water-soluble film. Pharmaceutically acceptable adjuvants, buffering agents, dispersing agents, and the like, may also be incorporated into the pharmaceutical compositions.

Binders include for instance, starch, mucilage, gelatin and sucrose. Lubricants include talc, lycopodium, magnesium and calcium stearate/stearic acid. Diluents include lactose, sucrose, mannitol, salt, starch and kaolin. Wetting agents include propylene glycol and sorbitan monostearate.

As used herein, local application or administration refers to administration of a pharmaceutical composition according to the invention to the site, such as an inflamed joint, that exhibits the painful and/or inflamed condition. Such local application includes intra joint, such as intra-articular application, via injection, application via catheter or delivery as part of a biocompatible device. Thus, local application refers to application to a discrete internal area of the body, such as, for example, a joint, soft tissue area (such as muscle, tendon, ligaments, intraocular or other fleshy internal areas), or other internal area of the body. In particular, as used herein, local application refers to applications that provide substantially no systemic delivery and/or systemic administration of the active agents in the present compositions. Also, as used herein, local application is intended to refer to applications to discrete areas of the body, that is, other than the various large body cavities (such as, for example, the peritoneal and/or pleural cavities).

As used herein, topical application refers to application to the surface of the body, such as to the skin, eyes, mucosa and lips, which can be in or on any part of the body, including but not limited to the epidermis, any other dermis, or any other body tissue. Topical administration or application means the direct contact of the pharmaceutical composition according to the invention with tissue, such as skin or membrane, particularly the cornea, or oral, vaginal or anorectal mucosa. Thus, for purposes herein, topical application refers to application to the tissue of an accessible body surface, such as, for example, the skin (the outer integument or covering) and the mucosa (the mucus-producing, secreting and/or containing surfaces). In particular, topical application refers to applications that provide little or substantially no systemic delivery of the active compounds in the present compositions. Exemplary mucosal surfaces include the mucosal surfaces of the eyes, mouth (such as the lips, tongue, gums, cheeks, sublingual and roof of the mouth), larynx, esophagus, bronchus, trachea, nasal passages, vagina and rectum/anus.

For oral administration, an active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach. Methods for enhancing peptide stability and absorption after oral administration are well known in the art (e.g., Mahato R I. Emerging trends in oral delivery of peptide and protein drugs. *Critical Reviews in Therapeutic Drug Carrier Systems.* 20:153-214, 2003).

Dosage forms such as lozenges, chewable tablets and chewing gum permit more rapid therapeutic action compared to per-oral dosage forms of the synthetic peptide amide compounds of the invention having significant buccal absorption. Chewing gum formulations are solid, single dose preparations with a base consisting mainly of gum, that are intended to be chewed but not swallowed, and contain one or more compounds of the invention which are released by chewing and are intended to be used for local treatment of pain and inflammation of the mouth or systemic delivery after absorption through the buccal mucosa. See for example, U.S. Pat. No. 6,322,828 to Athanikar and Gubler entitled: Process for manufacturing a pharmaceutical chewing gum.

For nasal administration, the peripherally selective kappa opioid receptor agonists can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, Drug Delivery to the Respiratory Tract, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159.

The pharmaceutical compositions of the invention can be prepared in a formulation suitable for systemic delivery, such as for instance by intravenous, subcutaneous, intramuscular, intraperitoneal, intranasal, transdermal, intravaginal, intrarectal, intrapulmonary or oral delivery. Alternatively, the pharmaceutical compositions of the invention can be suitably formulated for local delivery, such as, for instance, for topical, or iontophoretic delivery, or for transdermal delivery by a patch coated, diffused or impregnated with the formulation, and local application to the joints, such as by intra-articular injection.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous, and thereby formulated for delivery by injection, infusion, or using implantable pumps. For intravenous, subcutaneous, and intramuscular administration, useful formulations of the invention include microcapsule preparations with controlled release properties (R. Pwar et al. Protein and peptide parenteral controlled delivery. *Expert Opin Biol Ther.* 4(8):1203-12, 2004) or encapsulation in liposomes, with an exemplary form being polyethylene coated liposomes, which are known in the art to have an extended circulation time in the vasculature (e.g. Koppal, T. "Drug delivery technologies are right on target", *Drug Discov. Dev.* 6, 49-50, 2003).

For ophthalmic administration, the present invention provides a method of treating glaucoma or ophthalmic pain and inflammation, comprising administering to an eye of a patient in need thereof a therapeutically effective amount of a synthetic peptide amide of the invention. The synthetic peptide amide can be administered topically with an eye-compatible pharmaceutical carrier or non-systemically using a contact lens or intraocular implant that can optionally contain polymers that provide sustained release of the synthetic peptide amide. Such eye-compatible pharmaceutical carriers can include adjuvants, antimicrobial preservatives, surfactants, and viscolyzers etc. It is known in the art that high concentrations of many compounds are irritant to the eye and low concentrations are less irritant; thus the formulation is often designed to include the lowest effective concentrations of active compound, preservative, surfactant, and/or viscolyzer, said viscolyzer preferably having a high surface tension to reduce irritation of the eye while increasing the retention of ophthalmic solutions at the eye surface. Such controlled release of the synthetic peptide amides of the invention can last 6 months to a year for implants, or for shorter periods (3-14 days) for contact lenses. Such implants can be osmotic pumps, biodegradable matrices, or intraocular sustained release devices. Such topical compositions can include a buffered saline solution with or without liposomes.

Aqueous polymeric solutions, aqueous suspensions, ointments, and gels can be used for topical formulations of the synthetic peptide amides of the invention for ocular applications. The aqueous formulations may also contain liposomes for creating a reservoir of the synthetic peptide amide. Certain of these topical formulations are gels which enhance pre-corneal retention without the inconvenience and impairment of vision associated with ointments. The eye-compatible pharmaceutical carrier can also include a biodegradable synthetic polymer. Biodegradable microsphere compositions approved for human use include the polylactides: poly(lactic acid), poly(glycolic acid), and poly(lactic-coglycolic) acid. Additional biodegradable formulations include, but are not limited to: poly(anhydride-co-imide), poly(lactic-glycolic acid), polyethyl-2-cyanoacrylate, polycaprolactone, polyhydroxybutyrate valerate, polyorthoester, and polyethylene-oxide/polybutylene teraphthalate. Intraocular implantation or injection of sustained release compositions that include a synthetic peptide amide of the invention can provide long-term control (ranging from months to years) of intraocular pressure, and thereby avoiding or reducing the need for topical preparations. Useful methods for formulating and dispensing ophthalmic medications are disclosed in U.S. Pat. No. 7,122,579 to Schwartz et al, and in U.S. Pat. No. 7,105,512 to Morizono et al. Methods for formulating ophthalmic medications in contact lenses are disclosed by Gulsen and Chauhan, Ophthalmic drug delivery through contact lenses. *Investigative Ophthalmology and Visual Science,* (2004) 45:2342-2347.

Preparations for transdermal delivery are incorporated into a device suitable for said delivery, said device utilizing, e.g., iontophoresis (Kalia Y N et al. Iontophoretic Drug Delivery. *Adv Drug Deliv Rev.* 56:619-58, 2004) or a dermis penetrating surface (Prausnitz MR. Microneedles for Transdermal Drug Delivery. *Adv Drug Deliv Rev.* 56:581-7, 2004), such as are known in the art to be useful for improving the transdermal delivery of drugs. An electrotransport device and methods of operation thereof are disclosed in U.S. Pat. No. 6,718,201. Methods for the use of iontophoresis to promote transdermal delivery of peptides are disclosed in U.S. Pat. No. 6,313,092 and U.S. Pat. No. 6,743,432.

As used herein the terms "electrotransport", "iontophoresis", and "iontophoretic" refer to the delivery through a body surface (e.g., skin or mucosa) of one or more pharmaceutically active compounds by means of an applied electromotive force to an agent containing reservoir. The compound may be delivered by electromigration, electroporation, electroosmosis or any combination thereof. Electroosmosis has also been referred to as electrohydrokinesis, electro convection, and electrically induced osmosis. In general, electroosmosis of a compound into a tissue results from the migration of solvent in which the compound is contained, as a result of the application of electromotive force to the therapeutic species reservoir, such as for instance, solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, applied to the compounds of the instant invention, the terms "electrotransport", "iontophoresis" and "iontophoretic" refer to (1) the delivery of charged agents by electromigration, (2) the delivery of uncharged agents by the process of electroosmosis, (3) the delivery of charged or uncharged agents by electroporation, (4) the delivery of charged agents by the combined processes of electromigration and electroosmosis, and/or (5) the delivery of a mixture of charged and uncharged agents by the combined processes of electromigration and electroosmosis. Electrotransport devices generally employ two electrodes, both of which are positioned in close electrical contact with some portion of the skin of the body. One electrode, called the active or donor electrode, is the electrode from which the therapeutic agent is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device.

Depending upon the electrical charge of the compound to be delivered transdermally, either the anode or cathode may be the active or donor electrode. Thus, if the compound to be transported is positively charged, e.g., the compound exemplified in Example 1 herein, then the positive electrode (the anode) will be the active electrode and the negative electrode (the cathode) will serve as the counter electrode, completing the circuit. However, if the compound to be delivered is negatively charged, then the cathodic electrode will be the active electrode and the anodic electrode will be the counter electrode. Electrotransport devices additionally require a reservoir or source of the therapeutic agent that is to be delivered into the body. Such drug reservoirs are connected to the anode or the cathode of the electrotransport device to provide a fixed or renewable source of one or more desired species or agents. Each electrode assembly is comprised of an electrically conductive electrode in ion-transmitting relation with an ionically conductive liquid reservoir which in use is placed in contact with the patient's skin. Gel reservoirs such as those described in Webster (U.S. Pat. No. 4,383,529) are one form of reservoir since hydrated gels are easier to handle and manufacture than liquid-filled containers. Water is one liquid solvent that can be used in such reservoirs, in part because the salts of the peptide compounds of the invention are water soluble and in part because water is non-irritating to the skin, thereby enabling prolonged contact between the hydrogel reservoir and the skin. For electrotransport, the synthetic peptides of the invention can be formulated with flux enhancers such as ionic surfactants or cosolvents other than water (See for example, U.S. Pat. No. 4,722,726 and European Patent Application 278,473, respectively). Alternatively the outer layer (i.e., the stratum corneum) of the skin can be mechanically disrupted prior to electrotransport delivery therethrough, for example as described in U.S. Pat. No. 5,250,023.

Peripherally synthetic peptide amides that are well suited for electrotransport can be selected by measuring their electrotransport flux through the body surface (e.g., the skin or mucosa), e.g., as compared to a standardized test peptide with known electrotransport flux characteristics, e.g. thyrotropin releasing hormone (R. Burnette et al. *J. Pharm. Sci.* (1986) 75:738) or vasopressin (Nair et al. *Pharmacol Res.* 48:175-82, 2003). Transdermal electrotransport flux can be determined using a number of in vivo or in vitro methods well known in the art. In vitro methods include clamping a piece of skin of an appropriate mammal (e.g., human cadaver skin) between the donor and receptor compartments of an electrotransport flux cell, with the stratum corneum side of the skin piece facing the donor compartment. A liquid solution or gel containing the drug to be delivered is placed in contact with the stratum corneum, and electric current is applied to electrodes, one electrode in each compartment. The transdermal flux is calculated by sampling the amount of drug in the receptor compartment. Two successful models used to optimize transdermal electrotransport drug delivery are the isolated pig skin flap model (Heit M C et al. Transdermal iontophoretic peptide delivery: in vitro and in vivo studies with luteinizing hormone releasing hormone. *J. Pharm. Sci.* 82:240-243, 1993), and the use of isolated hairless skin from hairless rodents or guinea pigs, for example. See Hadzija B W et al. Effect of freezing on iontophoretic transport through hairless rat skin. *J. Pharm. Pharmacal.* 44, 387-390, 1992. Compounds of the invention for transdermal iontophoretic delivery can have one, or typically, two charged nitrogens, to facilitate their delivery.

Other useful transdermal delivery devices employ high velocity delivery under pressure to achieve skin penetration without the use of a needle. Transdermal delivery can be improved, as is known in the art, by the use of chemical enhancers, sometimes referred to in the art as "permeation enhancers", i.e., compounds that are administered along with the drug (or in some cases used to pretreat the skin, prior to drug administration) in order to increase the permeability of the stratum corneum, and thereby provide for enhanced penetration of the drug through the skin. Chemical penetration enhancers are compounds that are innocuous and serve merely to facilitate diffusion of the drug through the stratum corneum, whether by passive diffusion or an energy driven process such as electrotransport. See, for example, Meidan V M et al. Enhanced iontophoretic delivery of buspirone hydrochloride across human skin using chemical enhancers. *Int. J. Pharm.* 264:73-83, 2003.

Pharmaceutical dosage forms for rectal administration include rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories include bases or vehicles and agents that raise the melting point of the suppositories. Examples of bases include cocoa butter (theobroma oil), glycerin-gelatin, carbowax, (polyoxyethylene glycol) and appropriate mixtures of mono-, di- and triglycerides of fatty acids. Combinations of the various bases can also be used. Agents that raise the melting point of suppositories include spermaceti and wax. Rectal suppositories may be prepared either by the compression method or by molding. Rectal suppositories typically weigh about 2 gm to about 3 gm. Tablets and capsules for rectal administration are manufactured using the same pharmaceutically acceptable substance(s) and by the same methods as for formulations for oral administration.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride for injection, Ringers solution for injection, isotonic dextrose for injection, sterile water for injection, dextrose and lactated Ringers solution for injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfite. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween 80). A sequestering or chelating agent of metal ions such as EDTA can also be incorporated. Pharmaceutical carriers also include ethyl alcohol, polyethylene glycol and propylene glycol for water miscible vehicles and the pH can be adjusted to a physiologically compatible pH by addition of sodium hydroxide, hydrochloric acid, citric acid or lactic acid.

The active ingredient may be administered all at once, or may be divided into a number of smaller doses to be administered at intervals of time, or as a controlled release formulation. The term "controlled release formulation" encompasses formulations that allow the continuous delivery of a synthetic peptide amide of the invention to a subject over a period of time, for example, several days to weeks. Such formulations may be administered subcutaneously or intramuscularly and allow for the continual steady state release of a predetermined amount of compound in the subject over time. The controlled release formulation of synthetic peptide amide may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administration of the formulations. Thus, the concentration ranges set forth herein are exemplary only and are not intended to limit the scope or practice of the claimed invention.

The unit dose parenteral preparations include packaging in an ampoule or prepackaged in a syringe with, or without a needle for delivery. All preparations for parenteral administration are typically sterile, as is practiced in the art. Illustratively, intravenous infusion of a sterile aqueous buffered solution containing an active compound is an effective mode of administration. In another embodiment a sterile aqueous or oily solution or suspension containing the active material can be injected as necessary to produce the desired pharmacological effect.

The pharmaceutical compositions of the invention can be delivered or administered intravenously, transdermally, transmucosally, intranasally, subcutaneously, intramuscularly, orally or topically (such as for example to the eye). The compositions can be administered for prophylactic treatment of individuals suffering from, or at risk of a disease or a disorder. For therapeutic applications, a pharmaceutical composition is typically administered to a subject suffering from a disease or disorder, in an amount sufficient to inhibit, prevent, or ameliorate the disease or disorder. An amount adequate to accomplish this is defined as a "therapeutically effective dose."

The pharmaceutical compositions of the invention can be administered to a mammal for prophylactic or therapeutic purposes in any of the above-described formulations and delivery modes. The mammal can be any mammal, such as a domesticated or feral mammal, or even a wild mammal. The mammal can be any primate, ungulate, canine or feline. For instance, and without limitation, the mammal may be a pet or companion animal, such as a dog or a cat; a high-value mammal such as a thoroughbred horse or a show animal; a farm animal, such as a cow, a goat, a sheep or pig; or a primate such as an ape, gorilla, orangutan, lemur, monkey or chimpanzee. A suitable mammal for prophylaxis or treatment using the pharmaceutical compositions of the invention is a human.

The pharmaceutical compositions of the invention can be administered to a mammal having a disease or condition treatable by activation of the kappa opioid receptor. Alternatively, the pharmaceutical compositions can be administered as prophylactics to a mammal having a risk of contracting or developing a disease or condition preventable by activation of the kappa opioid receptor. Diseases or conditions that can be treated or prevented by administration of the pharmaceutical compositions of the invention include, without limitation, any condition that can be ameliorated by activation of the kappa opioid receptor, including such conditions as pain, inflammation, pruritis, hyponatremia, hypokalemia, congestive heart failure, liver cirrhosis, nephrotic syndrome, hypertension, edema, ileus, tussis and glaucoma.

In a particular embodiment, the pharmaceutical compositions of the invention can be co-administered with or can include one or more other therapeutic compounds or adjuvants, such as but not limited to other opioids, cannabinoids, antidepressants, anticonvulsants, neuroleptics, antihistamines, acetaminophen, corticosteroids, ion channel blocking agents, non-steroidal anti-inflammatory drugs (NSAIDs), and diuretics, many of which are synergistic in effect with the synthetic peptide amides of the invention.

Suitable opioids, include, without limitation, alfentanil, alphaprodine, anileridine, bremazocine, buprenorphine, butorphanol, codeine, conorphone, dextromoramide, dextropropoxyphene, dezocine, diamorphine, dihydrocodeine, dihydromorphine, diphenoxylate, dipipanone, doxpicomine, ethoheptazine, ethylketazocine, ethylmorphine, etorphine, fentanyl, hydrocodone, hydromorphone, ketobemidone, levomethadyl, levorphanol, lofentanil, loperamide, meperidine
(pethidine), meptazinol, methadone, morphine, morphine-6-glucuronide, nalbuphine, nalorphine, nicomorphine, oxycodone, oxymorphone, pentazocine, phenazocine, phenoperidine, piritramide, propiram, propoxyphene, remifentanil, sufentanil, tilidate, tonazocine, and tramadol.

One embodiment of the invention is co-formulation and/or co-administration of an opioid with substantial agonist activity at the mu opioid receptor, such as morphine, fentanyl, hydromorphone, or oxycodone, together with a synthetic peptide amide of the invention, for the purpose of a mu opioid dose-sparing effect, where the dose of the mu opioid is reduced to minimize common mu opioid side effects, particularly in opioid-naïve patients. Such side effects include constipation, nausea, vomiting, sedation, respiratory depression, pruritis (itching), mental confusion, disorientation and cognitive impairment, urinary retention, biliary spasm, delirium, myoclonic jerks, and seizures. The selection of the reduced mu opioid dose requires expert clinical judgment, and depends on the unique characteristics of the various mu opioids, as well as patient characteristics such as pain intensity, patient age, coexisting disease, current drug regimen and potential drug interactions, prior treatment outcomes, and patient preference (McCaffery, M. and Pasero, C., *Pain Clinical Manual*, Second Edition, Mosby, 1999).

Cannabinoids suitable for administration with or incorporation into the pharmaceutical compositions of the invention, include any natural cannabinoid, such as for instance, tetrahydrocannabinol (THC), or a THC derivative, or a synthetic cannabinoid, such as, for instance, levonantradol, marinol, nabilone, rimonabant or savitex.

Suitable antidepressants that can be co-administered with or incorporated into the pharmaceutical compositions of the invention, include for example, tricyclic antidepressants such as imipramine, desipramine, trimipramine, protriptyline, nortriptyline, amitriptyline, doxepin, and clomipramine; atypical antidepressants such as amoxapine, maprotiline, trazodone, bupropion, and venlafaxine; serotonin-specific reuptake inhibitors such as fluoxetine, sertraline, paroxetine, citalopram and fluvoxamine; norepinephrine-specific reuptake inhibitors such as reboxetine; or dual-action antidepressants such as nefazodone and mirtazapine.

Suitable neuroleptics that can be co-administered with or incorporated into the pharmaceutical compositions of the invention, include any neuroleptic, for example, a compound with D2 dopamine receptor antagonist activity such as domperidone, metaclopramide, levosulpiride, sulpiride, thiethylperazine, ziprasidone, zotepine, clozapine, chlorpromazine, acetophenazine, carphenazine, chlorprothixene, fluphenazine, loxapine, mesoridazine, molindone, perphenazine, pimozide, piperacetazine, perchlorperazine, thioridazine, thiothixene, trifluoperazine, triflupromazine, pipamperone, amperozide, quietiapine, melperone, remoxipride, haloperidol, rispiridone, olanzepine, sertindole, ziprasidone, amisulpride, prochlorperazine, and thiothixene.

Anticonvulsants such as phenobarbital, phenyloin, primidone, carbamazepine, ethosuximide, lamotrigine, valproic acid, vigabatrin, felbamate, gabapentin, levetiracetam, oxcarbazepine, remacemide, tiagabine, and topiramate can also usefully be incorporated into the pharmaceutical compositions of the invention.

Muscle relaxants such as methocarbamol, orphenadrine, carisoprodol, meprobamate, chlorphenesin carbamate, diazepam, chlordiazepoxide and chlorzoxazone; anti-migraine agents such as sumitriptan, analeptics such as caffeine, methylphenidate, amphetamine and modafinil; antihistamines such as chlorpheniramine, cyproheptadine, promethazine and pyrilamine, as well as corticosteroids such as methylprednisolone, betamethasone, hydrocortisone, prednisolone, cortisone, dexamethasone, prednisone, alclometasone, clobetasol, clocortolone, desonide, desoximetasone, diflorasone, fluocinolone, fluocinonide, flurandrenolide, fluticasone, floromethalone, halcinonide, halobetasol, loteprednol, mometasone, prednicarbate, and triamcinolone can also be incorporated into the pharmaceutical compositions of the invention.

Ion channel blocking agents such as, for instance, the sodium ion channel blocker, carbamazepine, as commonly used in the treatment of tinnitus, arrhythmia, ischemic stroke and epilepsy can be co-administered with or incorporated into the pharmaceutical compositions of the invention. Alternatively, or in addition, calcium ion channel blockers, such as ziconotide, can also be used, as can antagonists of the ion channel associated with the NMDA receptor, such as ketamine. There is evidence that at least some of these ion channel blockers can potentiate the analgesic effects of the kappa agonist and thereby reduce the dose required for affective pain relief. See for instance, Wang et al., 2000, *Pain* 84: 271-81.

Suitable NSAIDs, or other non-opioid compounds with anti-inflammatory and/or analgesic activity, that can be co-administered with or incorporated into the pharmaceutical compositions of the invention include, but are not limited to one or more of the following: aminoarylcarboxylic acid derivatives such as etofenamate, meclofenamic acid, mefanamic acid, niflumic acid; arylacetic acid derivatives such as acemetacin, amfenac, cinmetacin, clopirac, diclofenac, fenclofenac, fenclorac, fenclozic acid, fentiazac, glucametacin, isoxepac, lonazolac, metiazinic acid, naproxin, oxametacine, proglumetacin, sulindac, tiaramide and tolmetin; arylbutyric acid derivatives such as butibufen and fenbufen; arylcarboxylic acids such as clidanac, ketorolac and tinoridine. arylpropionic acid derivatives such as bucloxic acid, carprofen, fenoprofen, flunoxaprofen, ibuprofen, ibuproxam, oxaprozin, phenylalkanoic acid derivatives such as flurbiprofen, piketoprofen, pirprofen, pranoprofen, protizinic acid and tiaprofenic acid; pyranocarboxylic acids such as etodolac; pyrazoles such as mepirizole; pyrazolones such as clofezone, feprazone, mofebutazone, oxyphinbutazone, phenylbutazone, phenyl pyrazolidininones, suxibuzone and thiazolinobutazone; salicylic acid derivatives such as aspirin, bromosaligenin, diflusinal, fendosal, glycol salicylate, mesalamine, 1-naphthyl salicylate, magnesium salicylate, olsalazine and salicylamide, salsalate, and sulfasalazine; thiazinecarboxamides such as droxicam, isoxicam and piroxicam others such as ε-acetamidocaproic acid, acetaminophen, s-adenosylmethionine, 3-amino-4-hydroxybutyric acid, amixetrine, bendazac, bucolome, carbazones, cromolyn, difenpiramide, ditazol, hydroxychloroquine, indomethacin, ketoprofen and its active metabolite 6-methoxy-2-naphthylacetic acid; guaiazulene, heterocylic aminoalkyl esters of mycophenolic acid and derivatives, nabumetone, nimesulide, orgotein, oxaceprol, oxazole derivatives, paranyline, pifoxime, 2-substituted-4,6-di-tertiary-butyl-s-hydroxy-1,3-pyrimidines, proquazone and tenidap, and cox-2 (cyclooxygenase II) inhibitors, such as celecoxib or rofecoxib.

Suitable diuretics that can be co-administered with or incorporated into the pharmaceutical preparations of the invention, include, for example, inhibitors of carbonic anhydrase, such as acetazolamide, dichlorphenamide, and methazolamide; osmotic diuretics, such as glycerin, isosorbide, mannitol, and urea; inhibitors of $Na^+$—$K^+$-$2Cl^-$ symport (loop diuretics or high-ceiling diuretics), such as furosemide, bumetanide, ethacrynic acid, torsemide, axosemide, piretanide, and tripamide; inhibitors of $Na^+$-$Cl^-$ symport (thiazide and thiazidelike diuretics), such as bendroflumethiazide, chlorothiazide, hydrochlorothiazide, hydroflumethazide, methyclothiazide, polythiazide, trichlormethiazide, chlorthalidone, indapamide, metolazone, and quinethazone; and, in addition, inhibitors of renal epithelial $Na^+$ channels, such as amiloride and triamterene, antagonists of mineralocorticoid receptors (aldosterone antagonists), such as spironolactone, canrenone, potassium canrenoate, and eplerenone, which, together, are also classified as $K^+$-sparing diuretics. One embodiment is co-formulation and/or co-administration of a loop or thiazide diuretic together with a synthetic peptide amide of the invention for the purpose of a loop or thiazide diuretic dose-sparing effect, wherein the dose of the loop or thiazide diuretic is reduced to minimize undesired water retention, and prevent or reduce hyponatremia, particularly in the context of congestive heart failure, as well as other medical conditions where decreasing body fluid retention and normalizing sodium balance could be beneficial to a patient in need thereof. See R M Reynolds et al. Disorders of sodium balance Brit. Med. J. 2006; 332:702-705.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

A further embodiment is co-formulation and/or co-administration of a potassium-sparing diuretic, e.g., a mineralocorticoid receptor antagonist, such as spironolactone or eplerenone, together with a synthetic peptide amide of the invention, for the purpose of enabling a reduced dose of said potassium-sparing diuretic, wherein the dose of said diuretic is reduced to minimize hyperkalemia or metabolic acidosis, e.g., in patients with hepatic cirrhosis.

In particular embodiments, the synthetic peptide amides of the invention exhibit a long lasting duration of action when administered in therapeutically relevant doses in vivo. For instance, in some embodiments, the synthetic peptide amides of the invention when administered to a mammal at a dose of 3 mg/kg of the synthetic peptide amide maintain at least about 50% of maximum efficacy in a kappa opioid receptor-dependent assay at 3 hours post administration. In certain other embodiments, the synthetic peptide amides of the invention when administered to a mammal at a dose of 0.1 mg/kg of the synthetic peptide amide maintain at least about 50% of maximum efficacy in a kappa opioid receptor-dependent assay at 3 hours post administration. The maximum efficacy is operationally defined as the highest level of efficacy determined for the particular kappa opioid receptor-dependent assay for all agonists tested.

In certain embodiments, the synthetic peptide amides of the invention when administered to a mammal at a dose of 0.1 mg/kg maintain at least about 75% of maximum efficacy at 3 hours post administration. In still other embodiments, the synthetic peptide amides of the invention when administered to a mammal at a dose of 0.1 mg/kg maintain at least about 90% of maximum efficacy at 3 hours post administration. In certain other embodiments, the synthetic peptide amides of the invention when administered to a mammal at a dose of 0.1 mg/kg maintain at least about 95% of maximum efficacy at three hours post administration.

The invention further provides a method of treating or preventing a kappa opioid receptor-associated disease or condition in a mammal, wherein the method includes administering to the mammal a composition containing an effective amount of a synthetic peptide amide of the invention. The mammal can be any mammal, such as a domesticated or feral mammal, or even a wild mammal. Alternatively, the mammal can be a primate, an ungulate, a canine or a feline. For instance, and without limitation, the mammal may be a pet or companion animal, such as a high-value mammal such as a thoroughbred or show animal; a farm animal, such as a cow, a goat, a sheep or pig; or a primate such as an ape or monkey. In one particular aspect, the mammal is a human.

The effective amount can be determined according to routine methods by one of ordinary skill in the art. For instance, an effective amount can be determined as a dosage unit sufficient to prevent or to treat a kappa receptor-associated disease or condition in the mammal. Alternatively, the effective amount may be determined as an amount sufficient to approximate the $EC_{50}$ concentration or an amount sufficient to approximate two or three times or up to about five or even about ten times the $EC_{50}$ concentration in a therapeutically relevant body fluid of the mammal, for instance, where the body fluid is in direct apposition to a target tissue, such as the synovial fluid of an inflamed joint in a patient suffering from rheumatoid arthritis.

In one embodiment the synthetic peptide amide of the invention is a pharmaceutical composition that includes an effective amount of the synthetic peptide amide of the invention and a pharmaceutically acceptable excipient or carrier. In one aspect, the pharmaceutical composition includes a synthetic peptide amide of the invention in an amount effective to treat or prevent a kappa opioid receptor-associated condition in a mammal, such as a human. In another aspect the kappa opioid receptor-associated condition is pain, inflammation, pruritis, edema, ileus, tussis or glaucoma.

In one embodiment the pharmaceutical composition of the invention further includes one or more of the following compounds: an opioid, a cannabinoid, an antidepressant, an anticonvulsant, a neuroleptic, a corticosteroid, an ion channel blocking agent or a non-steroidal anti-inflammatory drug (NSAID).

Pharmaceutical compositions that include a synthetic peptide amide of the invention and a pharmaceutically acceptable vehicle or carrier can be used to treat or prevent one or more of a variety of kappa opioid receptor-associated diseases, disorders or conditions.

The kappa opioid receptor-associated disease, disorders or condition preventable or treatable with the synthetic peptide amides of the invention can be any kappa opioid receptor-associated condition, including but not limited to acute or chronic pain, inflammation, pruritis, hyponatremia, edema, ileus, tussis and glaucoma. For instance, the kappa opioid receptor-associated pain can be neuropathic pain, somatic pain, visceral pain or cutaneous pain. Some diseases, disorders, or conditions are associated with more than one form of pain, e.g., postoperative pain can have any or all of neuropathic, somatic, visceral, and cutaneous pain components, depending upon the type and extent of surgical procedure employed.

The kappa opioid receptor-associated inflammation can be any inflammatory disease or condition including, but not limited to sinusitis, rheumatoid arthritis tenosynovitis, bursitis, tendonitis, lateral epicondylitis, adhesive capsulitis, osteomyelitis, osteoarthritic inflammation, inflammatory bowel disease (IBD), irritable bowel syndrome (IBS), ocular inflammation, otitic inflammation or autoimmune inflammation.

The kappa opioid receptor-associated pruritis can be any pruritic disease or condition such as, for instance, ocular pruritis, e.g., associated with conjunctivitis, otitic pruritis, pruritis associated with end-stage renal disease, where many patients are receiving kidney dialysis, and other forms of cholestasis, including primary biliary cirrhosis, intrahepatic cholestasis of pregnancy, chronic cholestatic liver disease, uremia, malignant cholestasis, jaundice, as well as dermatological conditions such as eczema (dermatitis), including atopic or contact dermatitis, psoriasis, polycythemia vera, lichen planus, lichen simplex chronicus, pediculosis (lice), thyrotoxicosis, tinea pedis, urticaria, scabies, vaginitis, anal pruritis associated with hemorrhoids and, as well as insect bite pruritis and drug-induced pruritis, such as mu opioid-induced pruritis.

The kappa opioid receptor-associated edema can be any edematous disease or condition such as, for instance, edema due to congestive heart disease or to a syndrome of inappropriate antidiuretic hormone (ADH) secretion.

The kappa opioid receptor-associated ileus can be any ileus disease or condition including, but not limited post-operative ileus or opioid-induced bowel dysfunction.

The kappa opioid receptor-associated neuropathic pain can be any neuropathic pain, such as, for instance, trigeminal neuralgia, diabetic pain, viral pain such as herpes zoster-associated pain, chemotherapy-induced pain, nerve-encroaching metastatic cancer pain, neuropathic pain associated with traumatic injury and surgical procedures, as well as variants of headache pain that are thought to have a neuropathic component, e.g., migraine.

Kappa opioid-associated pain also includes ocular pain, e.g., following photo-refractive keratectomy (PRK), ocular laceration, orbital floor fracture, chemical burns, corneal abrasion or irritation, or associated with conjunctivitis, corneal ulcers, scleritis, episcleritis, sclerokeratitis, herpes zoster ophthalmicus, interstitial keratitis, acute iritis, keratoconjunctivitis sicca, orbital cellulites, orbital pseudotumor, pemphigus, trachoma, or uveitis.

Kappa opioid-associated pain also includes throat pain, particularly associated with inflammatory conditions, such as allergic rhinitis, acute bronchitis, the common cold, contact ulcers, herpes simplex viral lesions, infectious mononucleosis, influenza, laryngeal cancer, acute laryngitis, acute necrotizing ulcerative gingivitis, peritonsillar abscess, pharyngeal burns, pharyngitis, reflux laryngopharyngitis, acute sinusitis, and tonsillitis.

In addition, kappa opioid receptor-associated pain can be arthritic pain, kidney-stone, urinary tract stone, gallstone, and bile duct stone pain, uterine cramping, dysmenorrhea, endometriosis, mastitis, dyspepsia, post-surgical pain (such as, for instance, from appendectomy, open colorectal surgery, hernia repair, prostatectomy, colonic resection, gastrectomy, splenectomy, colectomy, colostomy, pelvic laparoscopy, tubal ligation, hysterectomy, vasectomy or cholecystecomy), post medical procedure pain (such as, for instance, after colonoscopy, cystoscopy, hysteroscopy or cervical or endometrial biopsy), otitic pain, breakthrough cancer pain, and pain associated with a GI disorder such as IBD or IBS or other inflammatory conditions, particularly of the viscera (e.g., gastroesophageal reflux disease, pancreatitis, acute polynephritis, ulcerative colitis, acute pyelonephritis, cholecystitis, cirrhosis, hepatic abscess, hepatitis, duodenal or gastric ulcer, esophagitis, gastritis, gastroenteritis, colitis, diverticulitis, intestinal obstruction, ovarian cyst, pelvic inflammatory disease, perforated ulcer, peritonitis, prostatitis, interstitial cystitis), or exposure to toxic agents, such as insect toxins, or drugs such as salicylates or NSAIDs.

The present invention provides a method of treating or preventing a kappa opioid receptor-associated disease or condition in a mammal, such as a human, wherein the method includes administering to the mammal a composition comprising an effective amount of a synthetic peptide amide of the invention. In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritis (such as atopic dermatitis, kidney-dialysis-associated pruritis, ocular pruritis, otitic pruritis, insect bite pruritis, or opioid-induced pruritis), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

Kappa opioid receptor-associated pain includes hyperalgesia, which is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors (Handwerker et al. (1991) *Proceeding of the VIth World Congress on Pain*, Bond et al., eds., Elsevier Science Publishers BV, pp. 59-70; Schaible et al. (1993) Pain 55:5-54). This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state. See for example, Woold et al. (1993) *Anesthesia and Analgesia* 77:362-79; Dubner et al. (1994) In, *Textbook of Pain*, Melzack et al., eds., Churchill-Livingstone, London, pp. 225-242.

In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritis (such as atopic dermatitis, kidney-dialysis-associated pruritis, ocular pruritis, otitic pruritis, insect bite pruritis, or opioid-induced pruritis), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

In another embodiment the kappa opioid receptor-associated condition is a kappa opioid receptor-associated condition preventable or treatable by sodium and potassium-sparing diuresis, also known as aquaresis. An example of such kappa opioid receptor-associated conditions preventable or treatable by administering a synthetic peptide amide of the invention includes edema. The edema may be due to any of a variety of diseases or conditions, such as congestive heart disease or syndrome of inappropriate ADH secretion.

In another embodiment the kappa opioid receptor-associated condition is hyponatremia or other edematous disease. The kappa opioid receptor-associated hyponatremia or edema can be any hyponatremic or edematous disease or condition such as, for instance, hyponatremia and edema associated with congestive heart failure or to a syndrome of inappropriate antidiuretic hormone (ADH) secretion, or hyponatremia that is associated with intensive diuretic therapy with thiazides and/or loop diuretics. The synthetic peptide amides of the invention exhibit a significant sodium-sparing and potassium-sparing aquaretic effect, which is beneficial in the treatment of edema-forming pathological conditions associated with hyponatremia and/or hypokalemia.

Accordingly, the synthetic peptide amides of the invention also have utility in methods of treating or preventing hyponatremia-related conditions, examples of which are provided below. Hyponatremia-related conditions can be categorized according to volume status as hypervolemic, euvolemic, or hypovolemic.

Hypervolemic hyponatremia is usually caused by an increase in total body water level as may be observed in cases of congestive heart failure, nephrotic syndrome and hepatic cirrhosis.

Euvolemic hyponatremia is often found in the syndrome of inappropriate antidiuretic hormone (ADH) secretion and may also be associated with pneumonia, small-cell lung cancer, polydipsia, cases of head injury, and organic causes (e.g., use of certain drugs, such as haloperidol) or a psychogenic cause.

Hypovolemic hyponatremia is due to a relative decrease in total body sodium level and may be associated with diuretic use, cases of interstitial nephritis or excessive sweating.

These forms of hyponatremia can be further classified according to the concentration of sodium in the urine (i.e., whether the concentration is greater than or less than thirty millimoles per liter. See: R M Reynolds et al. Disorders of sodium balance, Brit. Med. J. 2006; 332:702-705.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

In addition to these conditions, numerous other conditions are associated with hyponatremia including, without limitation: neoplastic causes of excess ADH secretion, including carcinomas of lung, duodenum, pancreas, ovary, bladder, and ureter, thymoma, mesothelioma, bronchial adenoma, carcinoid, gangliocytoma and Ewing's sarcoma; infections such as: pneumonia (bacterial or viral), abscesses (lung or brain), cavitation (aspergillosis), tuberculosis (lung or brain), meningitis (bacterial or viral), encephalitis and AIDS; vascular causes such as: cerebrovascular occlusions or hemorrhage and cavernous sinus thrombosis; neurologic causes such as: Guillan-Barre syndrome, multiple sclerosis, delirium tremens, amyotrophic lateral sclerosis, hydrocephalus, psychosis, peripheral neuropathy, head trauma (closed and penetrating), CNS tumors or infections and CNS insults affecting hypothalamic osmoreceptors; congenital malformations including: agenesis of corpus callosum, cleftlip/palate and other midline defects; metabolic causes such as: acute intermittent porphyria, asthma, pneurothorax and positive-pressure respiration; drugs such as: thiazide diuretics, acetaminophen, barbiturates, cholinergic agents, estrogen, oral hypoglycemic agents, vasopressin or desmopressin, high-dose oxytocin, chlorpropamide, vincristine, carbamezepine, nicotine, phenothiazines, cyclophosphamide, tricyclic antidepressants, monoamine oxidase inhibitors and serotonin reuptake inhibitors; administration of excess hypotonic fluids, e.g., during hospitalization, surgery, or during or after athletic events (i.e., exercise-associated hyponatremia), as well as use of low-sodium nutritional supplements in elderly individuals. See for example, Harrison's Principles of Internal Medicine, 16th Ed. (2005), p. 2102.

Other conditions associated with hyponatremia include renal failure, nephrotic syndrome (membranous nephropathy and minimal change disease), cachexia, malnutrition, rhabdomyolysis, surgical procedures, elective cardiac catheterization, blood loss, as well as hypercalcemia, hypokalemia, and hyperglycemia with consequent glycosuria leading to osmotic diuresis.

The invention also provides a method of treating or preventing a neuro-degenerative disease or condition in a mammal, such as a human, wherein the method includes administering to the mammal a composition that includes an effective amount of a synthetic peptide amide as described above. The neurodegenerative disease or condition can be any neurodegenerative disease or condition, such as for instance, ischemia, anoxia, stroke, brain injury, spinal cord injury or reperfusion injury. Alternatively, the neurodegenerative disease or condition can be a neurodegenerative disease of the eye. Particular neurodegenerative diseases of the eye treatable or preventable by the method of the invention include glaucoma, macular degeneration, retinal ischemic disease and diabetic neuropathy.

In certain embodiments the invention provides methods of prevention or treatment of certain neuronal diseases and conditions, such as diseases and conditions having a neurodegenerative component. Synthetic peptide amides of the invention can be administered in an amount effective to protect neuronal cells against the effects of pathology or injury that would lead to neurodegeneration and/or neuronal cell death of the untreated cells. For example, several diseases or conditions of the eye that have a neurodegenerative component can be prevented or treated by administration of an effective amount of the synthetic peptide amides of the invention. Such diseases and conditions of the eye include glaucoma, macular degeneration, retinal ischemic disease and diabetic neuropathy. Progression of these diseases and conditions is believed to involve neurodegeneration or neuronal cell death, for example by programmed cell death (apoptosis) in which the neuronal cells are committed to a pathway that without intervention would lead to cell death. It has been found that development or progression of these diseases and conditions can be prevented, or at least slowed, by treatment with kappa opioid receptor agonists. This improved outcome is believed to be due to neuroprotection by the kappa opioid receptor agonists. See for instance, Kaushik et al. "Neuroprotection in Glaucoma" (2003) *J. Postgraduate Medicine vol.* 49 (1): pp. 90-95.

In the case of glaucoma it is believed that prophylaxis and treatment by administration of kappa opioid receptor agonists is mediated by at least two distinct activities induced by activation of the kappa opioid receptor: neuroprotection and reduction of intraocular pressure (IOP). While not wishing to be bound by theory, it is believed that neuroprotection is due, at least in part, to induction of atrial natriuretic peptide (ANP) in the eye, leading to protection against oxidative damage and other insults.

Abnormally high intraocular pressure is also believed to be a factor leading to the development of glaucoma. Elevated intraocular pressure can also be prevented or treated by administration of kappa opioid receptor agonists by three separate activities triggered by activation of the receptor: reduction in secretion of aqueous humor, increased outflow of aqueous humor and aquaresis (sodium- and potassium-sparing diuresis, resulting in loss of water).

The invention also provides a method of treating or preventing a kappa-receptor-associated disease or condition of the eye of a mammal, such as high intraocular pressure (IOP). The method includes administering to the mammal a composition that includes an effective amount of a synthetic peptide amide as described above. In one aspect of the invention, the synthetic peptide amide is administered topically. In another aspect, the synthetic peptide amide is administered as an implant.

In other embodiments the invention provides methods of prevention or treatment of certain cardiovascular diseases and conditions having a cellular degenerative component. Synthetic peptide amides of the invention can be administered in an amount effective to protect myocardial cells against the effects of pathology or injury that would lead to degeneration and/or cell death of the untreated cells. For example, several cardiovascular diseases or conditions can be prevented or treated by administration of an effective amount of the synthetic peptide amides of the invention. Such cardiovascular diseases and conditions include, without limitation, coronary heart disease, ischemia, cardiac infarct, reperfusion injury and arrhythmia. See for example, Wu et al. "Cardioprotection of Preconditioning by Metabolic Inhibition in the Rat Ventricular Myocyte—Involvement of kappa Opioid Receptor" (1999) *Circulation Res* vol. 84: pp. 1388-1395. See also Yu et al. "Anti-Arrhythmic Effect of kappa Opioid Receptor Stimulation in the Perfused Rat Heart: Involvement of a cAMP-Dependent Pathway" (1999) *J Mol Cell Cardiol*. vol. 31(10): pp. 1809-1819.

Diseases and conditions of other tissues and organs that can be prevented or treated by administration of an effective amount of the synthetic peptide amides of the invention include, but are not limited to ischemia, anoxia, stroke, brain or spinal cord injury and reperfusion injury.

Another form of kappa opioid receptor-associated pain treatable or preventable with the synthetic peptide amides of the invention is hyperalgesia. In one embodiment, the method includes administering an effective amount of a synthetic peptide amide of the invention to a mammal suffering from or at risk of developing hyperalgesia to prevent, ameliorate or completely alleviate the hyperalgesia.

The synthetic peptide amides of the invention can be administered by methods disclosed herein for the treatment or prevention of any hyperalgesic condition, such as, but without limitation, a hyperalgesic condition associated with allergic dermatitis, contact dermatitis, skin ulcers, inflammation, rashes, fungal irritation and hyperalgesic conditions associated with infectious agents, burns, abrasions, bruises, contusions, frostbite, rashes, acne, insect bites/stings, skin ulcers, mucositis, gingivitis, bronchitis, laryngitis, sore throat, shingles, fungal irritation, fever blisters, boils, Plantar's warts, surgical procedures or vaginal lesions. For instance, the synthetic peptide amides of the invention can be administered topically to a mucosal surface, such as the mouth, esophagus or larynx, or to the bronchial or nasal passages. Alternatively, the synthetic peptide amides of the invention can be administered topically to the vagina or rectum/anus.

Moreover, the synthetic peptide amides of the invention can be administered by methods disclosed herein for the treatment or prevention of any hyperalgesic condition associated with burns, abrasions, bruises, abrasions (such as corneal abrasions), contusions, frostbite, rashes, acne, insect bites/stings, skin ulcers (for instance, diabetic ulcers or a decubitus ulcers), mucositis, inflammation, gingivitis, bronchitis, laryngitis, sore throat, shingles, fungal irritation (such as athlete's foot or jock itch), fever blisters, boils, Plantar's warts or vaginal lesions (such as vaginal lesions associated with mycosis or sexually transmitted diseases). Methods contemplated for administration of the synthetic peptide amides of the invention for the treatment or prevention of hyperalgesia include those wherein the compound is topically applied to a surface in the eyes, mouth, larynx, esophagus, bronchial, nasal passages, vagina or rectum/anus.

Hyperalgesic conditions associated with post-surgery recovery can also be addressed by administration of the synthetic peptide amides of the invention. The hyperalgesic conditions associated with post-surgery recovery can be any hyperalgesic conditions associated with post-surgery recovery, such as for instance, radial keratectomy, tooth extraction, lumpectomy, episiotomy, laparoscopy and arthroscopy.

Hyperalgesic conditions associated with inflammation are also addressable by administration of the synthetic peptide amides of the invention. Periodontal inflammation, orthodontic inflammation, inflammatory conjunctivitis, hemorrhoids and venereal inflammations can be treated or prevented by topical or local administration of the synthetic peptide amides of the invention.

The invention also provides a method of inducing diuresis in a mammal in need thereof. The method includes administering to the mammal a composition comprising an effective amount of a synthetic peptide amide of the invention as described above.

The invention further provides a method of inducing prolactin secretion in a mammal. The method includes administering to the mammal a composition comprising an effective amount of a synthetic peptide amide of the invention as described above. The method of inducing prolactin secretion is suitable for treating a mammal, such as a human suffering from insufficient lactation, inadequate lactation, sub-optimal lactation, reduced sperm motility, an age-related disorder, type I diabetes, insomnia or inadequate REM sleep. In a particular aspect, the method includes co-administering the synthetic peptide amide with a reduced dose of a mu opioid agonist analgesic compound to produce a therapeutic analgesic effect, the compound having an associated side effect, wherein the reduced dose of the compound has a lower associated side effect than the side effect associated with the dose of the mu opioid agonist analgesic compound necessary to achieve the therapeutic analgesic effect when administered alone.

The present invention also provides a method of binding a kappa opioid receptor in a mammal, the method includes the step of administering to the mammal a composition containing an effective amount of a synthetic peptide amide of the present invention. The effective amount can be determined according to routine methods by one of ordinary skill in the art. For instance, the effective amount can be determined as a dosage unit sufficient to bind kappa opioid receptors in a mammal and cause an antinociceptive effect, an anti-inflammatory effect, an aquaretic effect, or an elevation of serum prolactin levels or any other kappa opioid receptor-responsive effect. Alternatively, the effective amount may be determined as an amount sufficient to approximate the $EC_{50}$ in a body fluid of the mammal, or an amount sufficient to approximate two or three, or up to about five or even about ten times the $EC_{50}$ in a therapeutically relevant body fluid of the mammal.

Synthesis of the Peptide Amides of the Invention

As used herein, the chemical designation "tetrapeptide-[ω (4-amino-piperidine-4-carboxylic acid)]" is used to indicate the aminoacyl moiety of the synthetic peptide amides of the invention derived from 4-aminopiperidine-4-carboxylic acid, wherein the nitrogen atom of the piperidine ring is bound to the C-terminal carbonyl-carbon of the tetrapeptide fragment, unless otherwise indicated.

Figure 2:
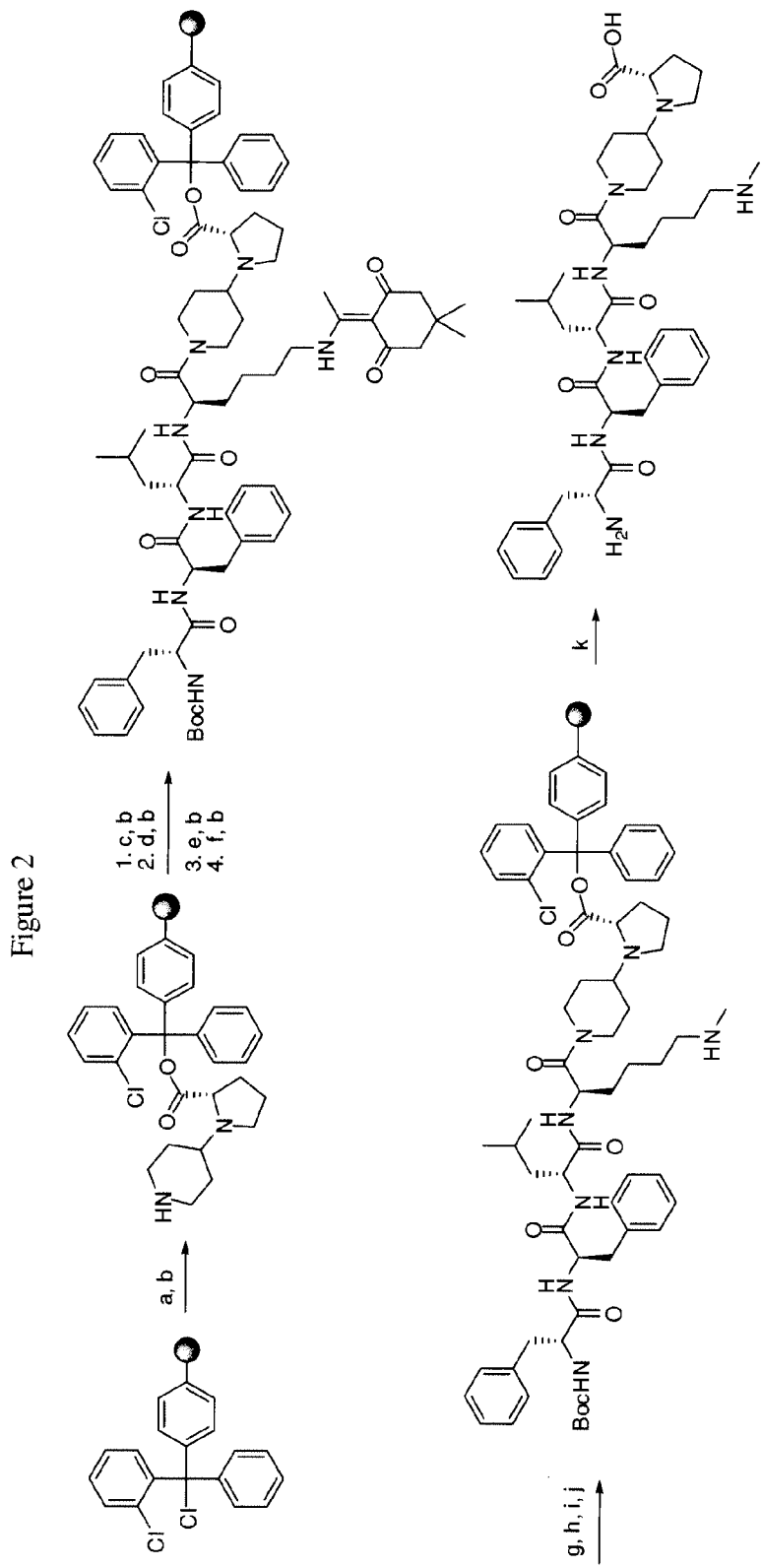
FIG. 2: General scheme used in the synthesis of compounds (2)-(5), (8), (9) and (12)-(14). Steps a-k were carried out with the following reactants or conditions: a) N-(1-Fmoc-piperidin-4-yl)-L-proline, DIEA, DCM; b) 25% piperidine/DMF; c) Fmoc-D-Lys(Dde)-OH, DIC, HOBt, DMF; d) Fmoc-D-Leu-OH, DIC, HOBt, DMF; e) Fmoc-D-Phe-OH, DIC, HOBt, DMF; f) Boc-D-Phe-OH, DIC, HOBt, DMF; g) 4% hydrazine in DMF; h) o-NBS-Cl, collidine, NMP; i) dimethylsulfate, DBU, NMP; j) mercaptoethanol, DBU, NMP; k) TFA/TIS/H$_2$O.
Figure 3:
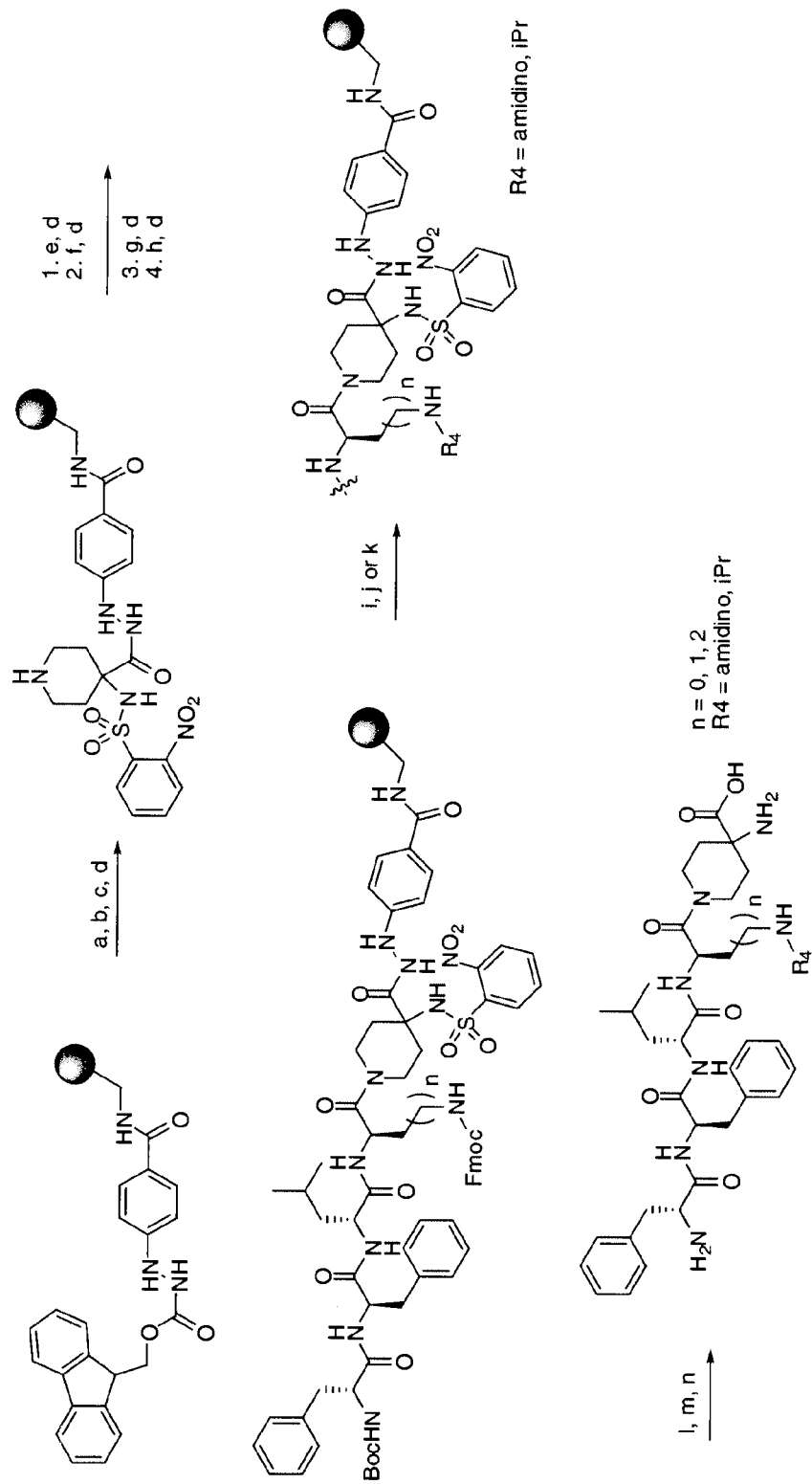
FIG. 3: General scheme used in the synthesis of compounds (15)-(24). Steps a-n were carried out with the following reactants or conditions: a) 35% piperidine, DMF; b) 1-Boc-4-N-Fmoc-amino-piperidine-4-carboxylic acid, PyBOP, DIEA, DMF; c) (i) 35% piperidine, DMF; (ii) O-NBS-Cl, collidine, NMP; d) 30% TFA in DCM; e) Boc-D-Dap(Fmoc)-OH or Boc-D-Dab(Fmoc)-OH or Boc-D-Orn(Fmoc)-OH, PyBOP, DIEA, DMF; f) Boc-D-Leu-OH, PyBOP, DIEA, DMF; g) Boc-D-Phe-OH, PyBOP, DIEA, DMF; h) Boc-D-Phe-OH, PyBOP, DIEA, DMF; i) 2% DBU/DMF; j) 1H-pyrazole-1-carboxamidine, DIEA, DMF; k) (i) acetone, TMOF, (ii) NaBH(OAc)$_3$, DMF; l) mercaptoethanol, DBU, NMP; m) Cu(OAc)$_2$, pyridine, DBU, DMF/H$_2$O; n) 95% TFA/H$_2$O.
Figure 4:
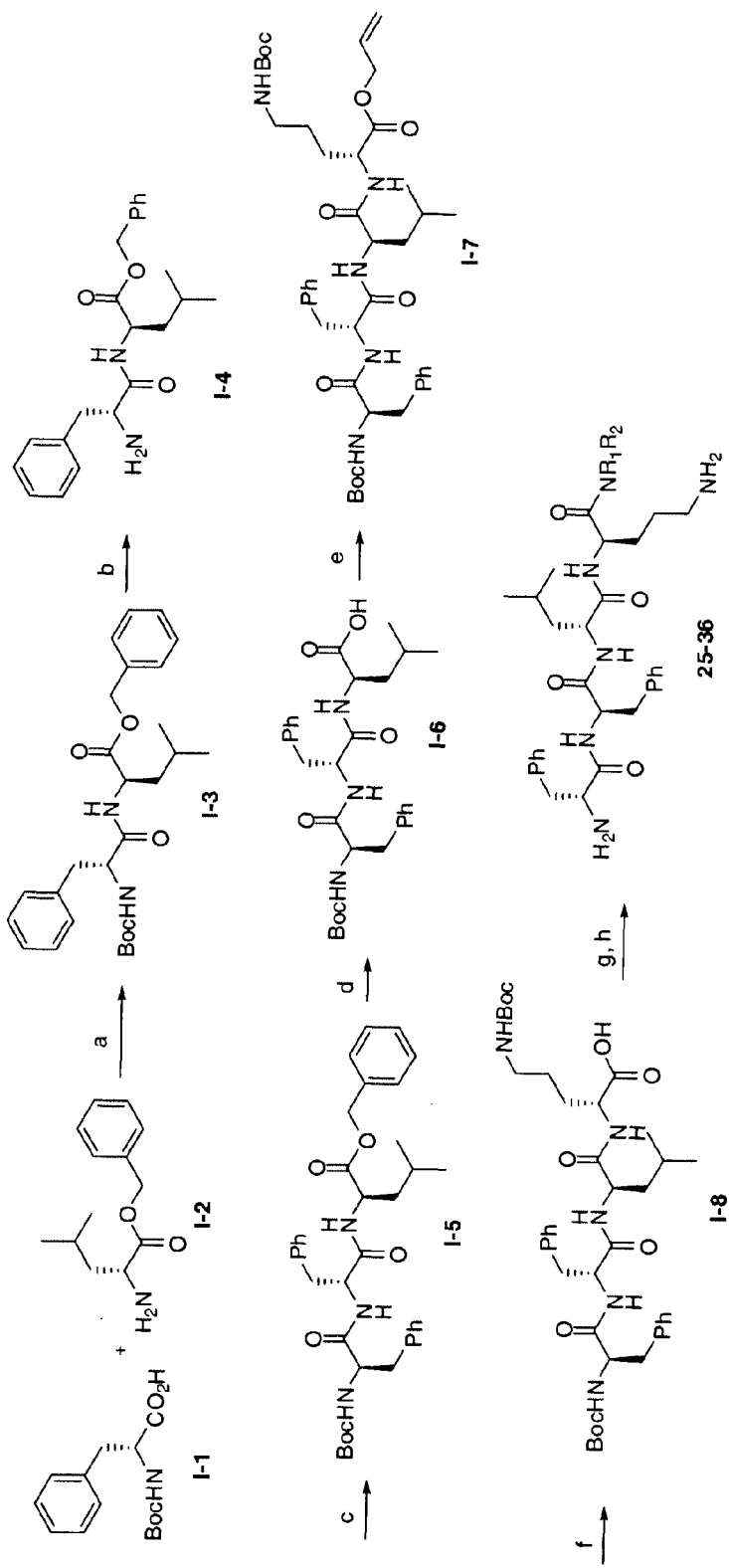
FIG. 4: General scheme used in the synthesis of compounds (25)-(37). Steps a-h were carried out with the following reactants or conditions: a) EDCI, HOBt, DIEA, THF; b) TFA, DCM; c) Boc-D-Phe-OH, EDCI, HOBt, DIEA; d) H$_2$, Pd/C; e) D-Lys(Boc)-OAll, TBTU, DIEA, DMF; f) Pd(PPh$_3$)$_4$, pyrrolidine; g) HNRaRb, HBTU; h) HCl, dioxane.

FIG. 1 shows the general synthetic scheme used in the preparation of compounds (1) (6), (7), (10) and (11); FIG. 2 shows the general synthetic scheme used in the preparation of compounds (2) to (5), (8), (9) and (12)-(14); FIG. 3 shows the general synthetic scheme used in the preparation of synthetic peptide amides (15)-(24); and FIG. 4 shows the scheme used in the preparation of the synthetic peptide amides (25)-(37):

Compound (1): D-Phe-D-Phe-D-Leu-(ε-Me)D-Lys[4-Amidinohomopiperazine amide]:

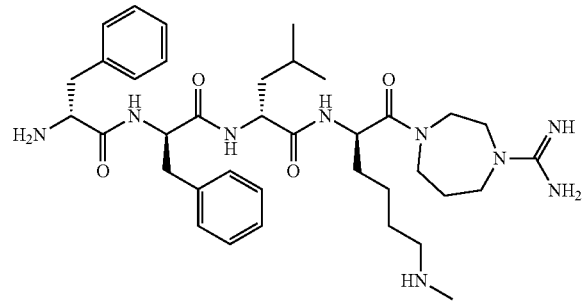

Compound (2): D-Phe-D-Phe-D-Leu-D-Lys-[ω(4-aminopiperidine-4-carboxylic acid)]-OH:

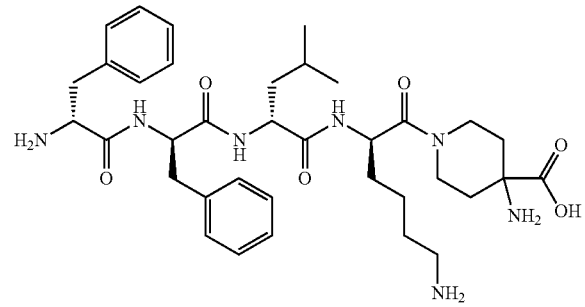

Compound (3): D-Phe-D-Phe-D-Leu-(ε-Me)D-Lys-[ω(4-aminopiperidine-4-carboxylic acid)]-OH:

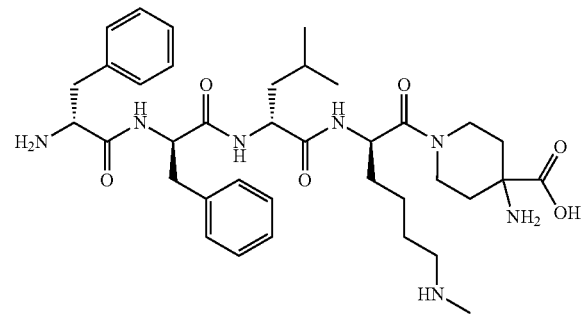

Compound (4): D-Phe-D-Phe-D-Leu-D-Lys-[N-(4-piperidinyl)-L-proline]-OH:

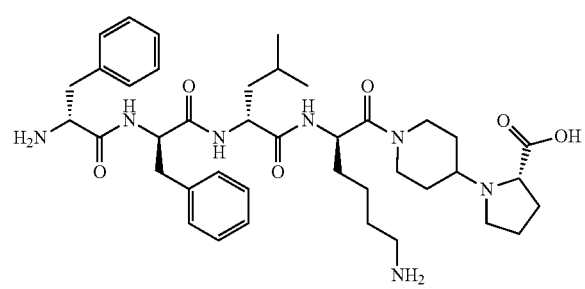

Compound (5): D-Phe-D-Phe-D-Leu-D-Har-[N-(4-piperidinyl)-L-proline]-OH:

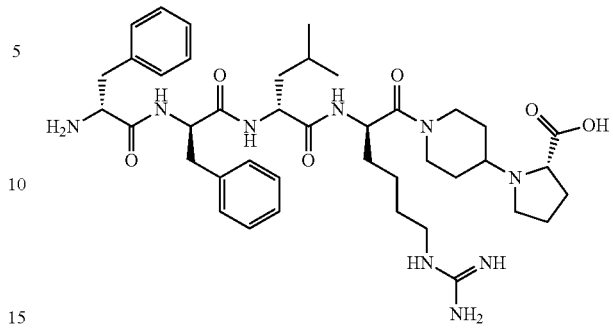

Compound (6): D-Phe-D-Phe-D-Leu-(ε-Me)D-Lys-[N-(4-piperidinyl)-L-proline]-OH:

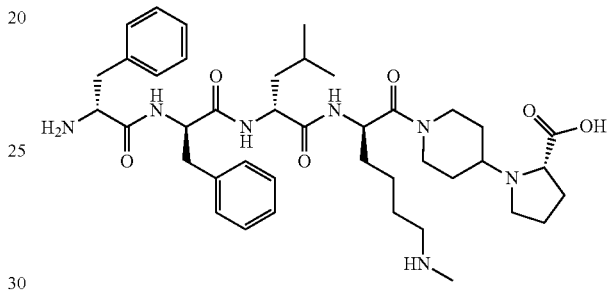

Compound (7): D-Phe-D-Phe-D-Leu-D-Arg-[homopiperazine amide]:

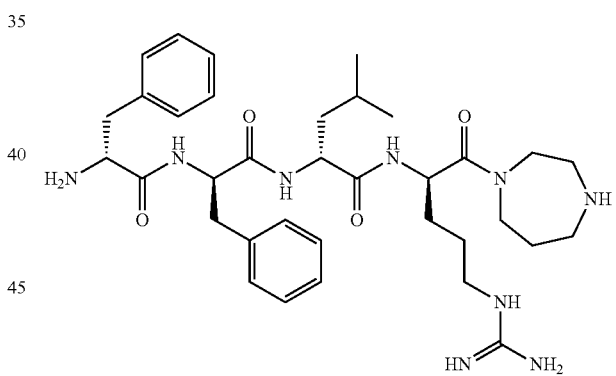

Compound (8): D-Phe-D-Phe-D-Leu-D-Har-[ω(4-aminopiperidine-4-carboxylic acid)]-OH:

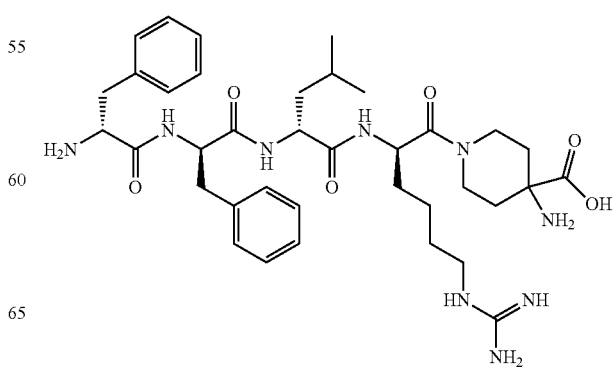

Compound (9): D-Phe-D-Phe-D-Leu-(ε-iPr)D-Lys-[ω(4-aminopiperidine-4-carboxylic acid)]-OH:

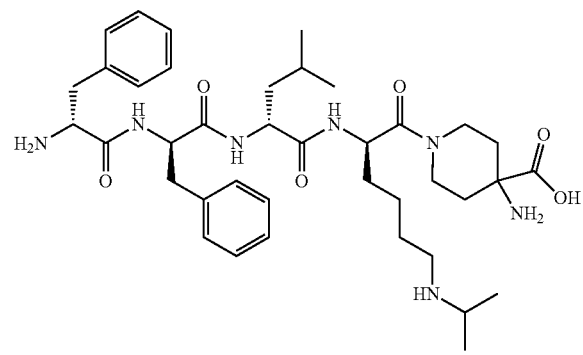

Compound (10): D-Phe-D-Phe-D-Leu-(β-amidino)D-Dap-[ω(4-aminopiperidine-4-carboxylic acid)]-OH:

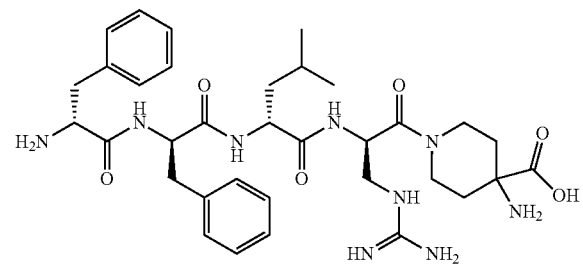

Compound (11): D-Phe-D-Phe-D-Leu-D-Nar-[ω(4-aminopiperidine-4-carboxylic acid)]-OH:

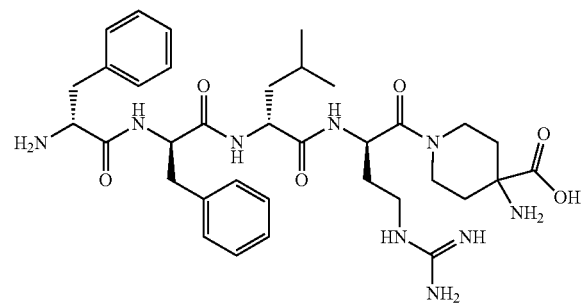

Compound (12): D-Phe-D-Phe-D-Leu-D-Dbu-[N-(4-piperidinyl)-L-proline]-OH:

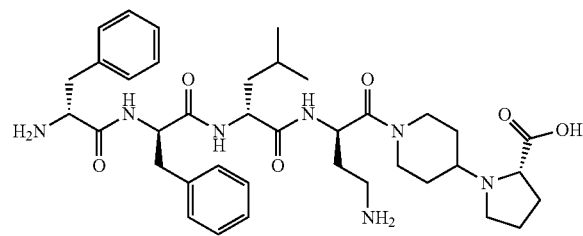

Compound (13): D-Phe-D-Phe-D-Leu-D-Nar-[N-(4-piperidinyl)-L-proline]-OH:

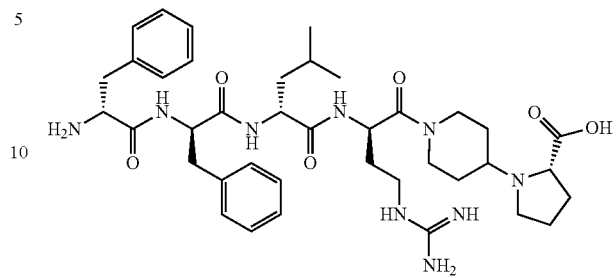

Compound (14): D-Phe-D-Phe-D-Leu-D-Dap(amidino)-[N-(4-piperidinyl)-L-proline]-OH:

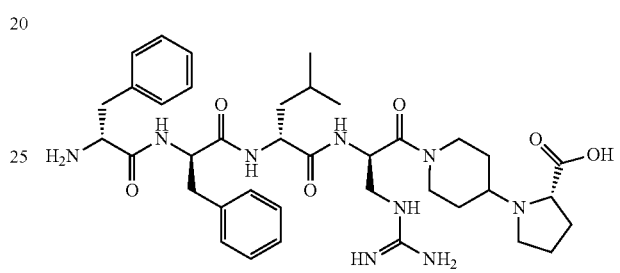

Compound (15): D-Phe-D-Phe-D-Leu-D-Lys-[4-Amidino-homopiperazine amide]:

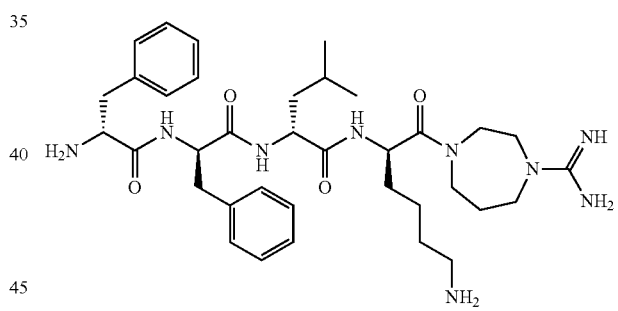

Compound (16): D-Phe-D-Phe-D-Leu-D-Har-[4-Amidino-homopiperazine amide]:

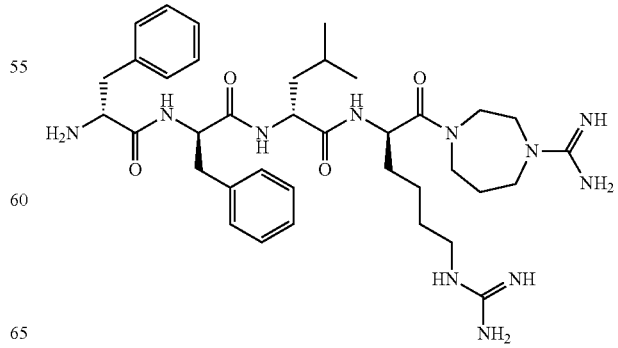

Compound (17): D-Phe-D-Phe-D-Leu-(ε-iPr)D-Lys-[4-Amidinohomopiperazine amide]:

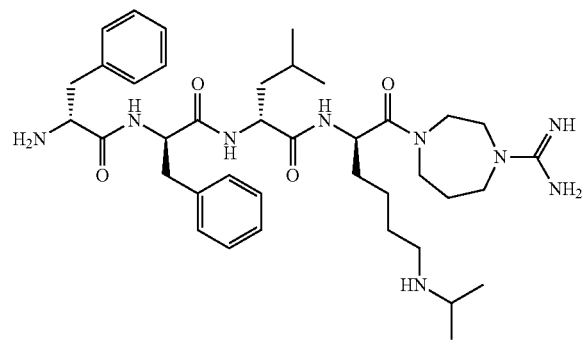

Compound (18): D-Phe-D-Phe-D-Leu-(β-amidino)D-Dap-[4-Amidinohomopiperazine amide]:

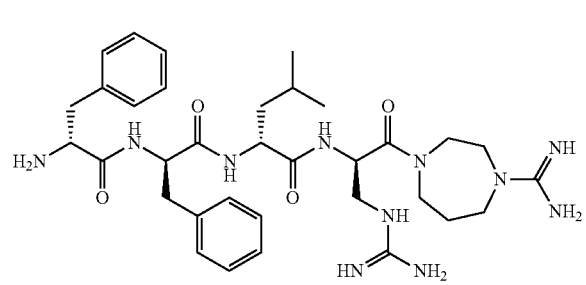

Compound (19): D-Phe-D-Phe-D-Nle-(β-amidino)D-Dap-[4-Amidinohomopiperazine amide]:

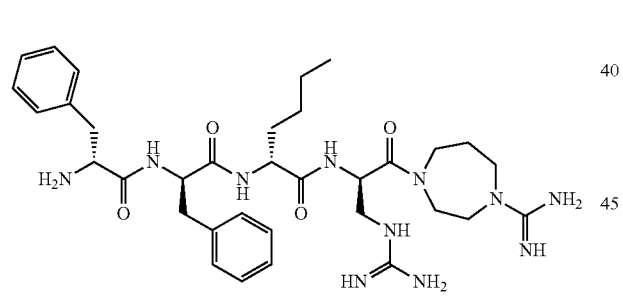

Compound (20): D-Phe-D-Phe-D-Leu-(β-amidino)D-Dap-[homopiperazine amide]:

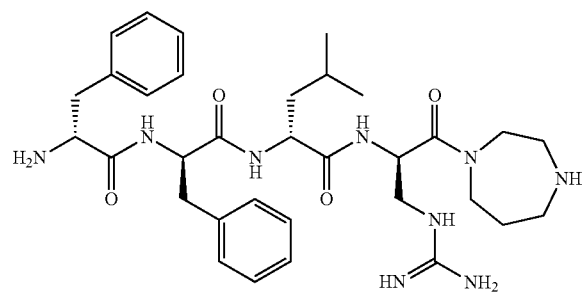

Compound (21): D-Phe-D-Phe-D-Nle-(β-amidino)D-Dap-[homopiperazine amide]:

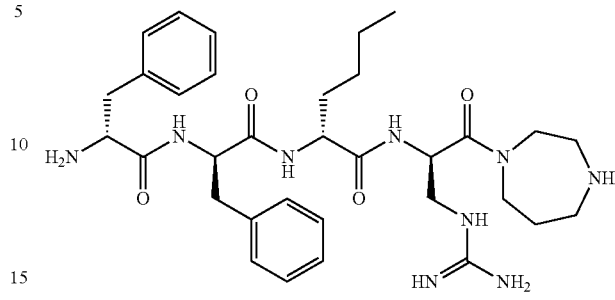

Compound (22): D-Phe-D-Phe-D-Leu-D-Dbu-[4-Amidino-homopiperazine amide]:

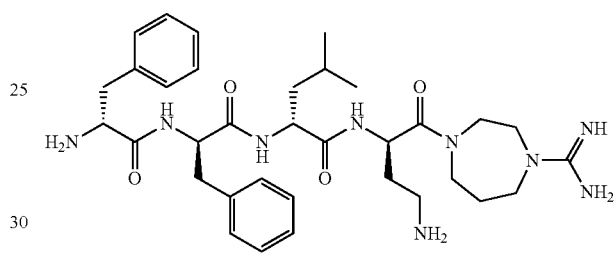

Compound (23): D-Phe-D-Phe-D-Leu-D-Nar-[4-Amidino-homopiperazine amide]:

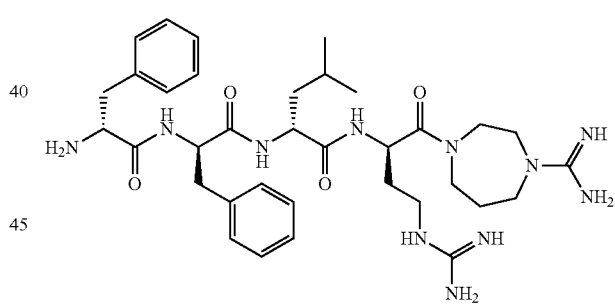

Compound (24): D-Phe-D-Phe-D-Leu-D-Arg-[4-Amidino-homopiperazine amide]:

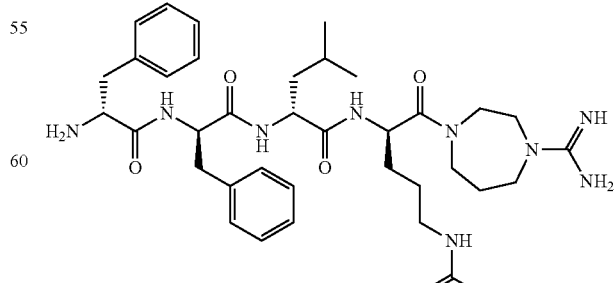

Compound (25): D-Phe-D-Phe-D-Leu-D-Lys-[2,8-diazaspiro[4,5]decan-1-one amide]:

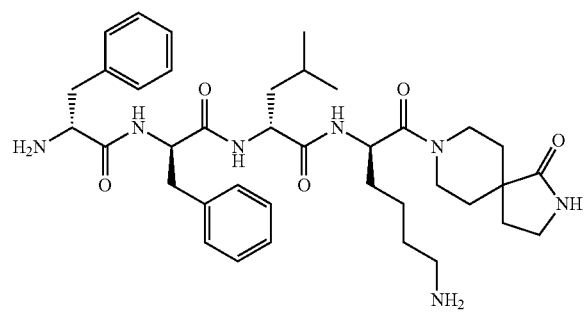

Compound (26): D-Phe-D-Phe-D-Leu-D-Lys-[2-methyl-2,8-diazaspiro[4,5]decan-1-one amide]:

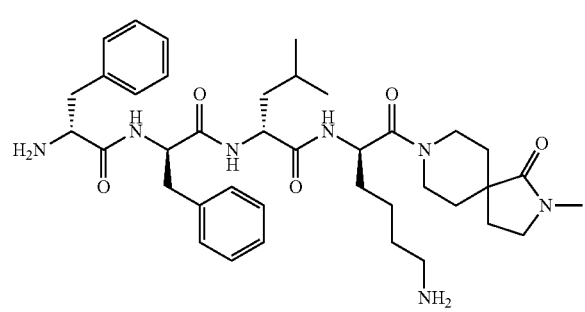

Compound (27): D-Phe-D-Phe-D-Leu-D-Lys-[1,3,8-triazaspiro[4,5]decane-2,4-dione amide]:

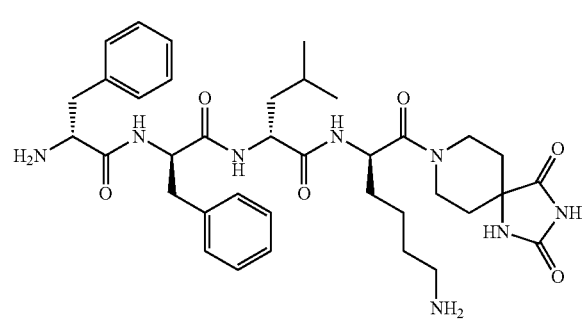

Compound (28): D-Phe-D-Phe-D-Leu-D-Lys-[5-chloro-1-(piperidin-4-yl)-1H-benzo[d]imidazol-2(3)H-one amide]:

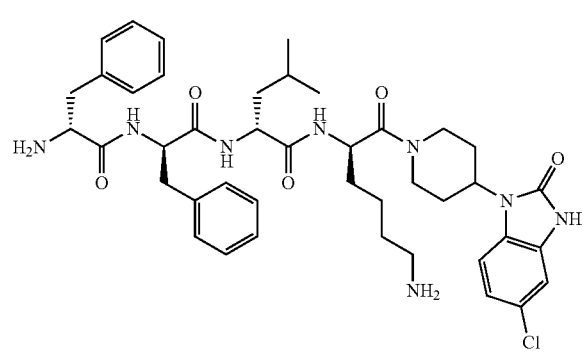

Compound (29): D-Phe-D-Phe-D-Leu-D-Lys-[morpholino(piperidin-4-yl)methanone amide]:

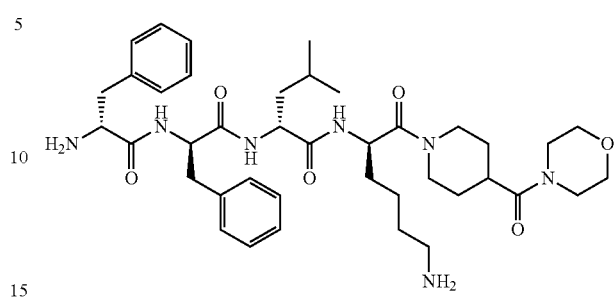

Compound (30): D-Phe-D-Phe-D-Leu-D-Lys-[4-phenyl-1-(piperidin-yl-1H-imidazol-2(3H)-one amide]:

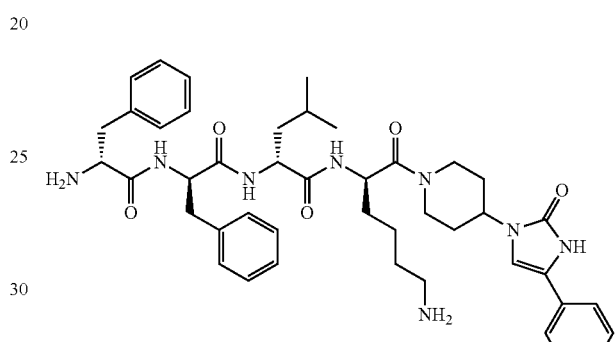

Compound (31): D-Phe-D-Phe-D-Leu-D-Lys-[4-(3,5-dimethyl-4H-1,2,4-triazol-4-yl)piperidine amide]:

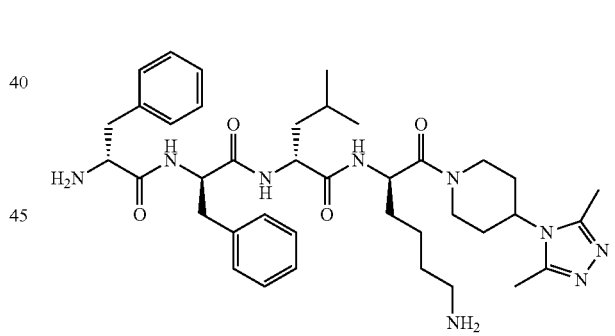

Compound (32): D-Phe-D-Phe-D-Leu-D-Lys-[1-(piperidin-4-yl)indolin-2-one amide]:

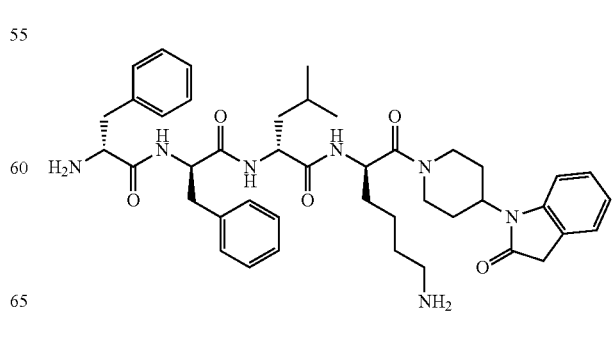

Compound (33): D-Phe-D-Phe-D-Leu-D-Lys-[1-phenyl-1,3,8-triazaspiro[4.5]decan-4-one amide]:

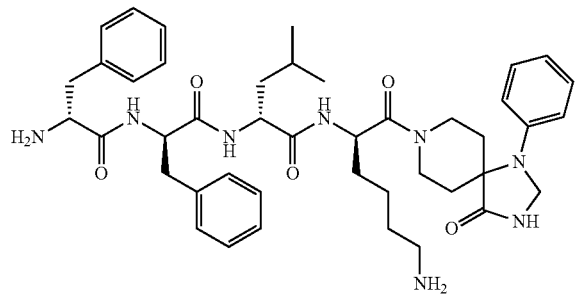

Compound (34): D-Phe-D-Phe-D-Leu-D-Lys-[imidazo[1,2-a]pyridine-2-ylmethyl amide]:

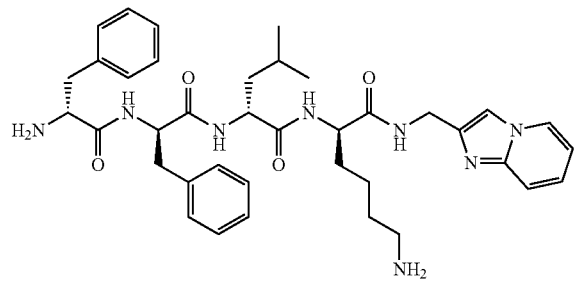

Compound (35) D-Phe-D-Phe-D-Leu-D-Lys-[(5-methylpyrazin-2-yl)methyl amide]:

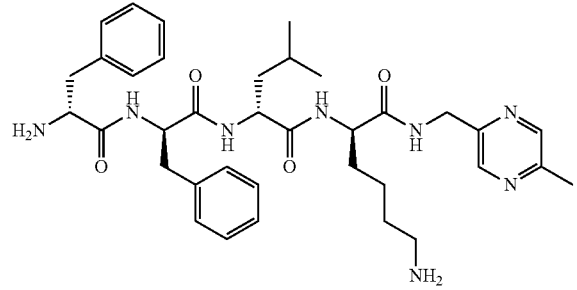

Compound (36): D-Phe-D-Phe-D-Leu-D-Lys[1-(piperidin-4-yl)-1H-benzo[d]imidazol-2(3H)-one amide]:

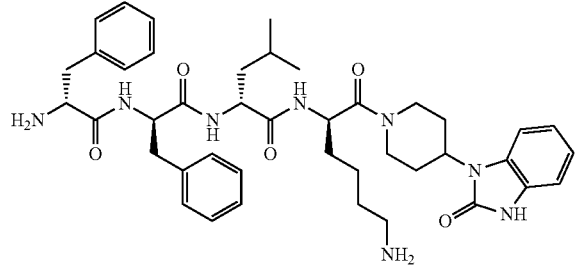

Compound (37): D-Phe-D-Phe-D-Leu-D-Lys-[4,5,6,7-tetrahydro-1H-pyrazolo[4,3-c]pyridine amide]:

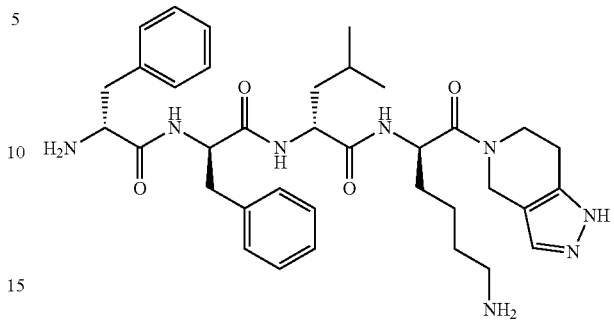

EXAMPLES

General Experimental Synthetic Methods

Amino acid derivatives and resins were purchased from commercial providers (Novabiochem, Bachem, Peptide International and PepTech Corporation). Other chemicals and solvents were purchased from Sigma-Aldrich, Fisher Scientific and VWR.

The compounds herein were synthesized by standard methods in solid phase peptide chemistry utilizing both Fmoc and Boc methodology. Unless otherwise specified, all reactions were performed at room temperature.

The following standard references provide guidance on general experimental setup, and the availability of required starting material and reagents: Kates, S. A., Albericio, F., Eds., *Solid Phase Synthesis, A Practical Guide*, Marcel Dekker, New York, Basel, (2000); Bodanszky, M., Bodanszky, A., Eds., *The Practice of Peptide Synthesis*, Second Edition, Springer-Verlag, (1994); Atherton, E., Sheppard, R. C., Eds., *Solid Phase Peptide Synthesis, A Practical Approach*, IRL Press at Oxford University Press, (1989); Stewart, J. M., Young, J. D., *Solid Phase Synthesis*, Pierce Chemical Company, (1984); Bisello, et al., *J. Biol. Chem.* 273, 22498-22505 (1998); and Merrifield, R. B., *J. Am. Chem. Soc.* 85, 2149-2154 (1963).

Additional abbreviations used herein:
ACN: acetonitrile
Aloc: allyloxycarbonyl
Boc: tert-butoxycarbonyl
BOP: benzotriazole-1-yl-oxy-tris(dimethylamino)-phosphonium hexafluorophosphate
Cbz: benzyloxycarbonyl.
Cbz-OSu: Nα-(Benzyloxycarbonyloxy) succinimide
DBU: 1,8-diazabicyclo[5.4.0]undec-7-ene
DCM: Dichloromethane
Dde: 1-(4,4-dimethyl-2,6-dioxocyclohex-1-ylidene)ethyl
DIC: N,N'-diisopropylcarbodiimide
DIEA: N,N-diisopropylethylamine
DMF: N,N-dimethylformamide
Fmoc: 9-fluorenylmethoxycarbonyl
HATU: 2-(1H-9-azabenzotriazole-1-yl)-1,1,3,3-tetramethylaminium hexafluorophosphate
HBTU: 2-(1H-benzotriazole-1-yl)-1,1,3,3-tetramethylaminium hexafluorophosphate
HOBt: 1-hydroxybenzotriazole
HPLC: high performance liquid chromatography
i: iso
ivDde: 1-(4,4-dimethyl-2,6-dioxocyclohex-1-ylidene)-3-methylbutyl NMM: 4-methyl morpholino
NMP: N-methylpyrrolidinone
All: allyl
o-NBS-Cl: o-nitrobenzenesulfonyl chloride
Pbf: 2,2,4,6,7-pentamethyldihydro-benzofuran-5-sulfonyl
PyBOP: benzotriazole-1-yloxy-tris-pyrrolidino-phosphonium hexafluorophosphate
RP: reversed phase
TBTU: 2-(1H-benzotriazole-1-yl)-1,1,3,3-tetramethyluronium tetrafluoroborate
TEAP: triethylammonium phosphate
TFA: trifluoroacetic acid
TIS: triisopropylsilane
TMOF: trimethyl orthoformate
TMSOTf: trimethylsilyl trifluoromethanesulfonate
Trt: trityl Peptides synthesized by Fmoc methodology were cleaved with a mixture of TFA/TIS/$H_2O$ (v/v/v=95:2.5:2.5). The cleavage step in the Boc methodology was accomplished either with a mixture of HF/anisole (v/v=9:1) or with a mixture of TMSOTf/TFA/m-cresol (v/v/v=2:7:1).

Coupling reactions in peptide chain elongation were carried out either manually on a peptide synthesizer and mediated by coupling reagents with a 2 to 4-fold excess amino acid derivatives. The coupling reagents used in the synthesis of the various compounds of the invention were chosen from the following combinations: DIC/HOBt, HATU/DIEA, HBTU/DIEA, TBTU/DIEA, PyBOP/DiEA, and BOP/DiEA.

Deprotection of the side chain of amino acid in position No. 4 (designated $Xaa_4$ in the final synthetic peptide amide product) of resin bound peptides was achieved as follows: Peptides were assembled starting from $Xaa_4$ and progressively adding $Xaa_3$, then $Xaa_2$ and finally, $Xaa_1$. The side chain protecting groups of the diamino acid introduced at $Xaa_4$ were selectively removed as follows: (i) N-Dde or N-ivDde groups were removed by 2-4% hydrazine in DMF. See Chabra, S. R., et al., *Tetrahedron Lett.* 39:1603-1606 (1998) and Rohwedder, B., et al., *Tetrahedron Lett.*, 39: 1175 (1998); (ii) N-Aloc: removed by 3 eq. $(Ph_3P)_4Pd$ in $CHCl_3$/AcOH/NMM (v/v/v=37:2:1). See Kates, S. A., et al. in "*Peptides Chemistry, Structure and Biology, Proc. 13th American Peptide Symposium*", Hodges, R. S, and Smith, J. A. (Eds), ESCOM, Leiden, 113-115 (1994).

When peptides were assembled with Boc protection methodology, the side chain protecting group of the diamino acids introduced at $Xaa_4$ was N-Fmoc, which was removed by 20-30% piperidine in DMF.

Isopropylation of the terminal nitrogen on the side chain of amino acid at $Xaa_4$ of resin bound peptides was achieved as follows: After deprotection, the resin bound peptide with the free ω-amino function at $Xaa_4$ was reacted with a mixture of acetone and $NaBH(OAc)_3$ in TMOF producing the resin bound Nω-isopropyl peptide.

Monomethylation of the terminal nitrogen on the side chain of amino acid at $Xaa_4$ of resin bound peptides: To synthesize resin bound Nω-methyl peptides, the free ω-amino function was first derivatized with o-nitrobenzenesulfonyl chloride (o-NBS-Cl; B iron, E.; Chatterjee, J.; Kessler, H. Optimized selective N-methylation of peptides on solid support. *J. Pep. Sci.* 12:213-219 (2006). The resulting sulfonamide was then methylated with a mixture of dimethylsulphate and 1,8-diaza-bicyclo[5.4.0]undec-7-ene in NMP. The o-NBS protecting group was subsequently removed by a mixture of mercaptoethanol and 1,8-diazabicyclo[5.4.0]undec-7-ene in NMP.

Guanylation of the terminal nitrogen on the side chain of amino acid at $Xaa_4$ of resin bound peptides: After deprotection, the resin bound peptide with the free ω-amino function in position No. 4 was reacted with a mixture of 1H-pyrazole-1-carboxamidine hydrochloride (Bernatowicz, M. S., et al., *J. Org. Chem.* 57, 2497-2502 (1992) and DIEA in DMF producing the resin bound Nω-guanidino peptide.

Peptides were purified by preparative HPLC in triethylammonium phosphate (TEAP) or trifluoroacetic acid (TFA) buffers. When required, the compounds were finally converted to trifluoroacetate or acetate salts using conventional HPLC methodology. Fractions with purity exceeding 97% were pooled and lyophilized. Purity of the synthesized peptides was determined by analytical RP-HPLC.

Analytical RP-HPLC was performed on a Waters 600 multisolvent delivery system with a Waters 486 tunable absorbance UV detector and a Waters 746 data module. HPLC analyses of peptides were carried out using a Vydac $C_{18}$ column (0.46×25 cm, 5 µm particle size, 300 Å pore size) at a flow rate of 2.0 ml/min. Solvents A and B were 0.1% TFA in $H_2O$ and 0.1% TFA in 80% ACN/20% $H_2O$, respectively. Retention times ($t_R$) are given in min. Preparative RP-HPLC was accomplished using a Vydac $C_{18}$ preparative cartridge (5×30 cm, 15-20 µm particle size, 300 Å pore size) at a flow rate of 100 ml/min, on a Waters Prep LC 2000 preparative chromatograph system with a Waters 486 tunable absorbance UV detector and a Servogor 120 strip chart recorder. Buffers A and B were 0.1% TFA in $H_2O$ and 0.1% TFA in 60% ACN/40% $H_2O$, respectively. HPLC analysis of the final compound was performed on a Hewlett Packard 1090 Liquid Chromatograph using a Phenomenex Synergi MAX-RP $C_{12}$ column (2.0×150 mm, 41-1 µM particle size, 80 Å pore size) at a flow rate of 0.3 ml/min at 40° C. Buffers A and B were 0.01% TFA in $H_2O$ and 0.01% TFA in 70% ACN/30% $H_2O$, respectively. The identity of the synthetic peptide amides was confirmed by electrospray mass spectrometry. Mass spectra were recorded on a Finnigan LCQ mass spectrometer with an ESI source.

Example 1

Synthesis of Compound (1)

D-Phe-D-Phe-D-Leu-(ε-Me)D-Lys-[4-Amidino-homopiperazine amide]

See the scheme shown in FIG. 1. The amino acid derivatives used were Bcz-D-Phe-OH, Fmoc-D-Phe-OH, Fmoc-D-Leu-OH, and Fmoc-D-Lys(Dde)-OH. The fully protected resin bound peptide was synthesized manually starting from p-nitrophenylcarbonate Wang resin (5.0 g, 4.4 mmol; Novabiochem). The attachment of homopiperazine to the resin was achieved by mixing it with a solution of homopiperazine (8.7 g, 87 mmol; Acros Organics) in DCM (100 mL) overnight at room temperature. The resin was washed with DMF and DCM and dried in vacuo. The resulting homopiperazine carbamate Wang resin (5.1 g; homopiperazine-[carbamate Wang resin]) was split into several portions and a portion of 1.5 g (1.3 mmol) was used to continue the peptide synthesis. DIC/HOBt mediated single couplings were performed with a 3-fold excess of amino acid derivatives. The Fmoc group was removed with 25% piperidine in DMF. Upon completion of peptide chain elongation, the resin was treated with 4% hydrazine in DMF for 3×3 min for Dde removal. The resin was washed with DMF and DCM and dried in vacuo. The resulting peptide resin (2.4 g; Bcz-D-Phe-D-Phe-DLeu-DLys-homopiperazine-[carbamate Wang resin]) was split again and a portion of 0.6 g (0.3 mmol) was used for subsequent derivatization (N-methylation).

Methylation of the ω-amino function of D-Lys at Xaa$_4$ was carried out in three steps: (i) [o-NBS Protection]: The resin-bound peptide (0.3 mmol) was first treated with a solution o-NBS-Cl (0.4 g, 2 mmol) and collidine (0.7 ml, 5 mmol) in NMP (7 ml) at room temperature for 30 min. The resin was then washed with NMP. (ii) [N-Methylation]: The resin-bound o-NBS protected peptide was then reacted with a solution of 1,8-diazabicyclo[5.4.0]undec-7-ene (0.5 ml, 3 mmol) and dimethylsulfate (1.0 ml, 10 mmol; Aldrich) in NMP (7 ml) at room temperature for 5 min. The resin was then washed with NMP and the washing process was repeated once. (iii) [o-NBS Deprotection]: The peptide resin was treated with a solution of mercaptoethanol (0.7 ml, 10 mmol) and 1,8-diazabicyclo[5.4.0]undec-7-ene (0.8 μl, 5 mmol) in NMP (7 ml) at room temperature for 5 min. The resin was then washed with NMP and the washing process was repeated once.

To protect the resulting N-methyl secondary amine of D-Lys at Xaa$_4$, the resin-bound methylated peptide was reacted with a solution of Bcz-OSu (6 mmol) in DMF (7 ml). The resin was washed with DMF and DCM and dried in vacuo. The peptide was then cleaved from the resin by treatment with a solution of TFA/DCM (15 ml, v/v=1:1) at room temperature for 2 hours. The resin was then filtered and washed with TFA. The filtrate was evaporated in vacuo and the crude peptide (0.3 mmol; Bcz-D-Phe-D-Phe-D-Leu-D-Lys(Me,Bcz)-[homopiperazine amide]) was precipitated from diethyl ether.

For guanylation of the homopiperazine at the C-terminus, the above peptide (0.3 mmol) was treated with a solution of 1H-Pyrazole-1-carboxamidine hydrochloride (0.4 g, 3.0 mmol) and DIEA (0.5 ml, 6 mmol) in DMF (3 ml) overnight at room temperature. Acetic acid and H$_2$O were added to quench the reaction and the solution was frozen and dried on a lyophilizer to give the desired protected peptide, Bcz-D-Phe-D-Phe-D-Leu-D-Lys(Me,Z)-[4-Amidinohomopiperazine amide] (0.6 g).

For final deprotection/hydrolysis, the above peptide (0.6 g) was treated with a mixture of TMSOTf/TFA/m-cresol (10 ml, v/v/v=2:7:1) at room temperature for 2 hours. The mixture was evaporated and the crude peptide (0.6 g) was precipitated from diethyl ether.

For purification, the above-derived crude peptide (0.6 g) was dissolved in 0.1% TFA in H$_2$O (50 ml) and the solution was loaded onto an HPLC column and purified using TFA buffer system (buffers A=0.1% TFA in H$_2$O and B=0.1% TFA in 60% ACN/40% H$_2$O). The compound was eluted with a linear gradient of buffer B, 25% B to 75% B over 30 min, $t_R$=37% B. The fractions with purity exceeding 97% were pooled, frozen, and dried on a lyophilizer to give the purified peptide as white amorphous powder (153 mg). HPLC analysis: $t_R$=14.41 min, purity 99.8%, gradient 5% B to 25% B over 20 min; MS (M+H$^+$): expected molecular ion mass 692.5, observed 692.5.

Example 2

Synthesis of Compound (2)

D-Phe-D-Phe-D-Leu-D-Lys-[ω(4-aminopiperidine-4-carboxylic acid)]:

See the scheme of FIG. 2 and B iron et al., Optimized selective N-methylation of peptides on solid support. *J. Peptide Science* 12: 213-219 (2006). The amino acid derivatives used were Boc-D-Phe-OH, Fmoc-D-Phe-OH, Fmoc-D-Leu-OH, Fmoc-D-Lys(Dde)-OH, and N-Boc-amino-(4-N-Fmoc-piperidinyl) carboxylic acid. HPLC and MS analyses were performed as described in the synthesis of compound (1) described above.

The fully protected resin-bound peptide was synthesized manually starting from 2-Chlorotrityl chloride resin (1.8 g, 0.9 mmol; Peptide International). Attachment of N-Boc-amino-(4-N-Fmoc-piperidinyl) carboxylic acid followed by peptide chain elongation and deprotection of Dde in D-Lys (Dde) at Xaa$_4$ was carried out according to the procedure described in the synthesis of compound (1). See above. The resulting peptide resin (0.9 mmol; Boc-D-Phe-D-Phe-D-Leu-D-Lys-(N-Boc-amino-4-piperidinylcarboxylic acid)-[2-Cl-Trt resin]) was split and a portion of 0.3 mmol was used for subsequent cleavage. The peptide resin (0.3 mmol) was then treated with a mixture of TFA/TIS/H$_2$O (15 ml, v/v/v=95:2.5:2.5) at room temperature for 90 min. The resin was then filtered and washed with TFA. The filtrate was evaporated in vacuo and the crude peptide (0.3 mmol; D-Phe-D-Phe-D-Leu-D-Lys-[w(4-aminopiperidine-4-carboxylic acid)]-OH) was precipitated from diethyl ether.

For purification, the crude peptide (0.3 mmol) was dissolved in 2% acetic acid in H$_2$O (50 ml) and the solution was loaded onto an HPLC column and purified using TEAP buffer system with a pH 5.2 (buffers A=TEAP 5.2 and B=20% TEAP 5.2 in 80% ACN). The compound was eluted with a linear gradient of buffer B, 7% B to 37% B over 60 min. Fractions with purity exceeding 95% were pooled and the resulting solution was diluted with two volumes of water. The diluted solution was then loaded onto an HPLC column for salt exchange and further purification with a TFA buffer system (buffers A=0.1% TFA in H$_2$O and B=0.1% TFA in 80% ACN/20% H$_2$O) and a linear gradient of buffer B, 2% B to 75% B over 25 min. Fractions with purity exceeding 97% were pooled, frozen, and dried on a lyophilizer to yield the purified peptide as white amorphous powder (93 mg). HPLC analysis: $t_R$=16.43 min, purity 99.2%, gradient 5% B to 25% B over 20 min; MS (M+H$^+$): expected molecular ion mass 680.4, observed 680.3.

Compound (2) was also prepared using a reaction scheme analogous to that shown in FIG. 2 with the following amino acid derivatives: Fmoc-D-Phe-OH, Fmoc-D-Leu-OH, Fmoc-D-Lys(Boc)-OH, and Boc-4-amino-1-Fmoc-(piperidine)-4-carboxylic acid.

The fully protected resin-bound peptide was synthesized manually starting from 2-Chlorotrityl chloride resin (PS 1% DVB, 500 g, 1 meq/g). The resin was treated with Boc-4-amino-1-Fmoc-4-(piperidine)-4-carboxylic acid (280 g, 600 mmol) in a mixture of DMF, DCM and DMA (260 mL of each) was added. The mixture was stirred for 4 hours and then the resin was capped for 1 h by the addition of MeOH (258 mL) and DMA (258 mL). The resin was isolated and washed with DMF (3×3 L). The resin containing the first amino acid was treated with piperidine in DMF (3×3 L of 35%), washed with DMF (9×3 L) and Fmoc-D-Lys(Boc)-OH (472 g) was coupled using PyBOP (519 g) in the presence of HOBt (153 g) and DMA (516 mL) and in DCM/DMF (500 mL/500 mL) with stirring for 2.25 hours. The dipeptide containing resin was isolated and washed with DMF (3×3.6 L). The Fmoc group was removed by treatment with piperidine in DMF (3×3.6 L of 35%) and the resin was washed with DMF (9×3.6 L) and treated with Fmoc-D-Leu-OH (354 g), DIC (157 mL) and HOBt (154 g) in DCM/DMF (500 mL/500 mL) and stirred for 1 hour. Subsequent washing with DMF (3×4.1 L) followed by cleavage of the Fmoc group with piperidine in DMF (3×4.2 L of 35%) and then washing of the resin with DMF (9×4.2 L) provided the resin bound tripeptide. This material was treated with Fmoc-D-Phe-OH (387 g), DIC (157 mL) and HOBt (153 g) in DCM/DMF (500 mL/500 mL) and stirred overnight. The resin was isolated, washed with DMF (3×4.7 L) and then treated with piperidine in DMF (3×4.7 L of 35%) to cleave the Fmoc group and then washed again with DMF (9×4.7 L). The tetrapeptide loaded resin was treated with Fmoc-D-Phe-OH (389 g), DIC (157 mL) and HOBt (154 g) in DCM/DMF (500 mL/500 mL) and stirred for 2.25 hours. The resin was isolated, washed with DMF (3×5.2 L) and then treated piperidine (3×5.2 L of 35%) in DMF. The resin was isolated, and washed sequentially with DMF (9×5.2 L) then DCM (5×5.2 L). It was dried to provide a 90.4% yield of protected peptide bound to the resin. The peptide was cleaved from the resin using TFA/water (4.5 L, 95/5), which also served to remove the Boc protecting groups. The mixture was filtered, concentrated (1/3) and then precipitated by addition to MTBE (42 L). The solid was collected by filtration and dried under reduced pressure to give crude peptide.

For purification, the crude peptide was dissolved in 0.1% TFA in $H_2O$ and purified by preparative reverse phase HPLC (C18) using 0.1% TFA/water—ACN gradient as the mobile phase. Fractions with purity exceeding 95% were pooled, concentrated and lyophilized to provide pure peptide (>95.5% pure). Ion exchange was conducted using a Dowex ion exchange resin, eluting with water. The aqueous phase was filtered (0.22 μm filter capsule) and freeze-dried to give the acetate salt of the peptide (overall yield, 71.3%, >99% pure).

Example 3

Synthesis of Compound (3)

D-Phe-D-Phe-D-Leu-(ε-Me)D-Lys-[ω(4-aminopiperidine-4-carboxylic acid)]-OH:

The synthesis was started with 0.3 mmol of the peptide resin: Boc-D-Phe-D-Phe-D-Leu-D-Lys-(N-Boc-amino-4-piperidinylcarboxylic acid)-[2-Cl-Trt resin], which was prepared during the synthesis of compound (2) as described below. HPLC and MS analyses were also performed as described in the synthesis of compound (2) above.

For the methylation of the ω-amino function of D-Lys at $Xaa_4$, a three-step procedure as described in the synthesis of compound (1) was followed. See description above. The resin-bound methylated peptide (Boc-D-Phe-D-Phe-D-Leu-(ε-Me)D-Lys-(N-Boc-amino-4-piperidinylcarboxylic acid)-[2-Cl-Trt resin]) was then treated with a mixture of TFA/TIS/$H_2O$ (15 ml, v/v/v=95:2.5:2.5) at room temperature for 90 min. The resin was then filtered and washed with TFA. The filtrate was evaporated in vacuo and the crude peptide (0.3 mmol; D-Phe-D-Phe-D-Leu-(ε-Me)D-Lys-[o(4-amino-piperidine-4-carboxylic acid)]-OH) was precipitated from diethyl ether.

The crude peptide (0.3 mmol) was purified by preparative HPLC according to the protocol described in the synthesis of compound (2). See above. Fractions with purity exceeding 97% were pooled, frozen, and dried on a lyophilizer to yield the purified peptide as white amorphous powder (185 mg). HPLC analysis: $t_R$=16.93 min, purity 99.2%, gradient 5% B to 25% B over 20 min; MS (M+H$^+$): expected molecular ion mass 694.4, observed 694.4.

Example 4

Synthesis of Compound (4)

D-Phe-D-Phe-D-Leu-D-Lys-[N-(4-piperidinyl)-L-proline]-OH:

The amino acid derivatives used were Boc-D-Phe-OH, Fmoc-D-Phe-OH, Fmoc-D-Leu-OH, Fmoc-D-Lys(Dde)-OH, and N-(1-Fmoc-piperidin-4-yl)-L-proline. HPLC and MS analyses were performed as described in the synthesis of compound (1). See detailed description above. The scheme followed was substantially as shown in FIG. 2, except that couplings were mediated by HATU/DIEA rather than DIC.

The fully protected resin-bound peptide was synthesized manually starting from 2-Chlorotrityl chloride resin (3.2 g, 2.4 mmol; NeoMPS). The attachment of the first amino acid to the resin was achieved by treatment with a mixture of N-(1-Fmoc-piperidin-4-yl)-L-proline (2.0 g, 4.8 mmol) and DIEA (3.3 ml, 19.2 mmol) in DCM (40 ml) and DMF (10 ml) at room temperature for 4 hours. The resin was washed with 3×DCM/MeOH/DIEA (v/v/v=17:2:1) and 3×DCM and dried in vacuo. The resulting resin (3.7 g; N-(4-piperidinyl)-L-proline-[2-Cl-Trt resin]) was split into several portions and a portion of 1.9 g (1.2 mmol) was used to continue the peptide synthesis. HATU/DIEA-mediated single couplings were performed with a 3-fold excess of amino acid derivatives. The Fmoc group was removed with 25% piperidine in DMF. Upon completion of peptide chain elongation, the resin was treated with 4% hydrazine in DMF three times for 3 min each to remove Dde. The resin was washed with DMF and DCM and dried in vacuo. The resulting peptide resin (2.1 g; Boc-D-Phe-D-Phe-D-Leu-D-Lys-N-(4-piperidinyl)-L-proline-[2-Cl-Trt resin]) was split again and a portion of 0.7 g (0.4 mmol) was used for subsequent cleavage. The peptide resin was treated with a mixture of TFA/TIS/$H_2O$ (15 ml, v/v/v=95:2.5:2.5) at room temperature for 90 min. The resin was filtered and washed with TFA. The filtrate was evaporated in vacuo and the crude peptide (220 mg, D-Phe-D-Phe-D-Leu-D-Lys-[N-(4-piperidinyl)-L-proline]-OH) was precipitated from diethyl ether.

For purification, the above crude peptide (220 mg) was dissolved in 0.1% TFA in $H_2O$ (50 ml) and the solution was loaded onto an HPLC column and purified using TFA buffer system (buffers A=0.1% TFA in $H_2O$ and B=0.1% TFA in 60% ACN/40% $H_2O$). The compound was eluted with a linear gradient of buffer B, 25% B to 75% B over 25 min, $t_R$=43% B. Fractions with purity exceeding 97% were pooled, frozen, and dried on a lyophilizer to give the purified peptide as white amorphous powder (89 mg). HPLC analysis: $t_R$=18.22 min, purity 99.5%, gradient 5% B to 25% B over 20 min; MS (M+H$^+$): expected molecular ion mass 734.5, observed 734.4.

Example 5

Synthesis of Compound (5)

D-Phe-D-Phe-D-Leu-D-Har-[N-(4-piperidinyl)-L-proline]-OH:

The peptide-resin: Boc-D-Phe-D-Phe-D-Leu-D-Lys-N-(4-piperidinyl)-L-proline-[2-Cl-Trt resin], which was prepared during the synthesis of compound (4) described above, was used as the starting material. HPLC and MS analyses were performed as described in the synthesis of compound (1) above.

For guanylation of the ω-amino function of D-Lys at Xaa₄, the peptide resin (0.7 g, 0.4 mmol) was treated with a mixture of 1H-Pyrazole-1-carboxamidine hydrochloride (0.6 g, 4.0 mmol) and DMA (0.7 ml, 4.0 mmol) in DMF (15 ml) overnight at room temperature. The resin was washed with DMF and DCM and dried in vacuo. The peptide was then cleaved from the resin by treatment with a mixture of TFA/TIS/H$_2$O (15 ml, v/v/v=95:2.5:2.5) at room temperature for 90 min. The resin was then filtered and washed with TFA. The filtrate was evaporated in vacuo and the crude peptide (170 mg; D-Phe-D-Phe-D-Leu-D-Har-[N-(4-piperidinyl)-L-proline]-OH) was precipitated from diethyl ether.

For purification, the above crude peptide (170 mg) was dissolved in 0.1% TFA in H$_2$O (50 ml) and the solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 25% B to 75% B over 25 min, $t_R$=46% B. Fractions with purity exceeding 97% were pooled, frozen, and lyophilized to yield the purified peptide as white amorphous powder (81 mg). HPLC analysis: $t_R$=19.42 min, purity 100%, gradient 5% B to 25% B over 20 min; MS (M+H⁺): expected molecular ion mass 776.5, observed 776.5.

Example 6

Synthesis of Compound (6)

D-Phe-D-Phe-D-Leu-(ε-Me)D-Lys-[N-(4-piperidinyl)-L-proline]-OH:

Synthesis was initiated with 0.7 g (0.4 mmol) of the peptide resin, Boc-D-Phe-D-Phe-D-Leu-D-Lys-N-(4-piperidinyl)-L-proline-[2-Cl-Trt resin], which was prepared during the synthesis of compound (4) as described above. HPLC and MS analyses were performed as described in the synthesis of compound (1) above. In this case, the Xaa$_1$-Xaa$_4$ peptide was pre-synthesized and coupled as opposed to the stepwise assembly of the peptide shown in FIG. 2.

For the methylation of the ω-amino function of D-Lys at Xaa$_4$, a three-step procedure was followed as described in the synthesis of compound (1) above. The resin-bound methylated peptide (Boc-D-Phe-D-Phe-D-Leu-(ε-Me)D-Lys-N-(4-piperidinyl)-L-proline-[2-Cl-Trt resin]) was then treated with a mixture of TFA/TIS/H$_2$O (15 ml, v/v/v=95:2.5:2.5) at room temperature for 90 minutes. The resin was filtered and washed with TFA. The filtrate was evaporated in vacuo and the crude peptide (200 mg; D-Phe-D-Phe-D-Leu-(ε-Me)D-Lys-[N-(4-piperidinyl)-L-proline]-OH) was precipitated from diethyl ether.

For purification, the above crude peptide (200 mg) was dissolved in 0.1% TFA in H$_2$O (50 ml) and the solution loaded onto an HPLC column and purified using a TFA buffer system (buffers A=0.1% TFA in H$_2$O and B=0.1% TFA in 60% ACN/40% H$_2$O). The compound was eluted with a linear gradient of 25% to 75% buffer B, over 30 min, $t_R$=42% B. Fractions with purity exceeding 97% were pooled, frozen, and dried on a lyophilizer to yield the purified peptide as white amorphous powder (41 mg). HPLC analysis: $t_R$=18.66 min, purity 98.1%, gradient 5% B to 25% B over 20 min; MS (M+H⁺): expected molecular ion mass 748.5, observed 748.5.

Example 7

Synthesis of Compound (7)

D-Phe-D-Phe-D-Leu-D-Arg-[homopiperazine amide]:

The amino acid derivatives used were Boc-D-Phe-OH, Fmoc-D-Phe-OH, Fmoc-D-Leu-OH, and Fmoc-D-Arg(Pbf)-OH. HPLC and MS analyses were performed as in the synthesis of compound (1) described above. The fully protected resin bound peptide was synthesized on a SYMPHONY Multiple Synthesizer (Protein Technology Inc.) starting from the homopiperazine carbamate Wang resin (0.35 mmol; homopiperazine-[carbamate Wang resin]) that was prepared during the synthesis of compound (1). HBTU/DIEA mediated single couplings with a 4-fold excess of amino acid derivatives were performed. The Fmoc group was removed with 25% piperidine in DMF. Upon completion of the automated synthesis, the peptide resin (Boc-D-Phe-D-Phe-D-Leu-D-Arg(Pbf)-[homopiperazine amide]) was transferred into a manual peptide synthesis vessel and treated with a mixture of TFA/TIS/H$_2$O (15 ml, v/v/v=95:2.5:2.5) at room temperature for 90 min. The resin was filtered and washed with TFA. The filtrate was evaporated in vacuo and the crude peptide (380 mg; D-Phe-D-Phe-D-Leu-D-Arg-[homopiperazine amide]) was precipitated from diethyl ether.

For purification, the above crude peptide (380 mg) was dissolved in 0.1% TFA in H$_2$O (50 ml) and the solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 25% B to 75% B over 25 min, $t_R$=36% B. Fractions with purity exceeding 97% were pooled, frozen, and lyophilized to give the purified peptide as white amorphous powder (222 mg). HPLC analysis: $t_R$=16.75 min, purity 100%, gradient 2% B to 22% B over 20 min; MS (M+H⁺): expected molecular ion mass 664.4, observed 664.5.

Example 8

Synthesis of Compound (8)

D-Phe-D-Phe-D-Leu-D-Har-[ω(4-aminopiperidine-4-carboxylic acid]-OH:

This compound was prepared essentially according to the procedure described above for the synthesis of compound (5) except that N-Boc-amino-(4-N-Fmoc-piperidinyl) carboxylic acid was substituted for N-(1-Fmoc-piperidin-4-yl)-L-proline in the attachment to 2-Cl-Trt resin. Final purified peptide: amorphous powder, 85 mg in yield in a synthesis scale of 1 mmol. HPLC analysis: $t_R$=17.87 min, purity 100%, gradient 5% B to 25% B over 20 min; MS (M+H⁺): expected molecular ion mass 722.4, observed 722.5.

Example 9

Synthesis of Compound (9)

D-Phe-D-Phe-D-Leu-(ε-iPr)D-Lys-[ω(4-aminopiperidine-4-carboxylic acid)]-OH:

Synthesis was initiated from 0.15 mmol of the peptide resin, Boc-D-Phe-D-Phe-D-Leu-D-Lys-(N-Boc-amino-4-piperidinylcarboxylic acid)-[2-Cl-Trt resin]), which was prepared during the synthesis of compound (2) above. For isopropylation of the ω-amino function of D-Lys at Xaa$_4$, the peptide resin was treated with a mixture of sodium triacetoxyborohydride (3 mmol) and acetone (6 mmol) in TMOF (10 mL) for 4 h at room temperature. Subsequent cleavage and purification steps were carried out according to the procedure described in the synthesis of compound (2). Final purified peptide: amorphous powder, 67 mg in yield. HPLC analysis:

$t_R$=19.29 min, purity 98.4%, gradient 5% B to 25% B over 20 min; MS (M+H$^+$): expected molecular ion mass 722.5, observed 722.5.

Example 10

Synthesis of Compound (10)

D-Phe-D-Phe-D-Leu-(β-amidino)D-Dap-[ω(4-aminopiperidine-4-carboxylic acid)]-OH:

See the scheme of FIG. 3. The amino acid derivatives used were Boc-D-Phe-OH, Boc-D-Phe-OH, Boc-D-Leu-OH, Boc-D-Dap(Fmoc)-OH, and N-Fmoc-amino-(4-N-Boc-piperidinyl) carboxylic acid. HPLC and MS analyses were performed as described in the synthesis of compound (1). The fully protected resin-bound peptide was synthesized manually starting with 4-Fmoc-hydrazinobenzoyl AM NovaGel resin (3 mmol; Novabiochem). The Fmoc protecting group on the starting resin was first removed by 25% piperidine in DMF and the resin was then treated with a mixture of N-Fmoc-amino-(4-N-Boc-piperidinyl) carboxylic acid (7.5 mmol), PyBOP (7.5 mmol), and DIEA (15 mmol) in DMF overnight at room temperature. The Fmoc group on the attached amino acid was replaced by o-NBS in two steps: (i) Fmoc removal by 25% piperidine in DMF. (ii) o-NBS protection according the procedure described in the synthesis of compound (1). The resulting peptide resin, N-o-NBS-amino-(4-N-Boc-piperidinyl) carboxylic acid-[hydrazinobenzoyl AM NovaGel resin], was split into several portions and a portion of 1 mmol was used to continue the peptide synthesis. PyBOP/DIEA mediated single couplings were performed with a 3-fold excess of amino acid derivatives. The Boc group was removed with 30% TFA in DCM. Upon completion of peptide chain elongation, the resin was treated with 2% DBU in DMF for 2×8 min for Fmoc removal, followed by guanylation of the ω-amino function of D-Dap at Xaa$_4$ according to the procedure described in the synthesis of compound (5), above. The final o-NBS deprotection was carried out according to the procedure described in the synthesis of compound (1).

For oxidative cleavage, the dried peptide resin was mixed with a mixture of Cu(OAc)$_2$ (1 mmol), pyridine (4 mmol), and DBU (2 mmol) in 5% H$_2$O in DMF and let air bubble through the resin for 6 h at room temperature. The resin was filtered and washed with DMF and the filtrated was evaporated in vacuo. The residue, Boc-D-Phe-D-Phe-D-Leu-(β-amidino) D-Dap-[ω(4-aminopiperidine-4-carboxylic acid)]-OH, was treated with 95% TFA in H$_2$O for Boc removal. The solution was evaporated in vacuo and the crude peptide (1 mmol; D-Phe-D-Phe-D-Leu-(β-amidino)D-Dap-[w(4-aminopiperidine-4-carboxylic acid)]-OH) was precipitated from diethyl ether.

Purification of the above crude peptide was achieved according to the protocol described in the synthesis of compound (2). The purified peptide was an amorphous powder (16 mg). HPLC analysis: $t_R$=16.97 min, purity 99.9%, gradient 5% B to 25% B over 20 min; MS (M+H$^+$): expected molecular ion mass 680.4, observed 680.4.

Example 11

Synthesis of Compound (11)

D-Phe-D-Phe-D-Leu-D-Nar-[ω(4-aminopiperidine-4-carboxylic acid)]-OH:

This compound was prepared according to the procedure described in the synthesis of compound (10), except that Boc-D-Dbu(Fmoc)-OH was substituted for Boc-D-Dap (Fmoc)-OH in the coupling of the amino acid derivative at Xaa$_4$. Final purified peptide: amorphous powder, 23 mg in yield in a synthesis scale of 1 mmol. HPLC analysis: $t_R$=17.12 min, purity 99.2%, gradient 5% B to 25% B over 20 min; MS (M+H$^+$): expected molecular ion mass 694.4, observed 694.5.

Example 12

Synthesis of Compound (12)

D-Phe-D-Phe-D-Leu-D-Dbu-[N-(4-piperidinyl)-L-proline]-OH:

This compound was prepared according to the procedure described in the synthesis of compound (4), as described above. The variation was the substitution of Fmoc-D-Dbu (ivDde)-OH for Fmoc-D-Lys(Dde)-OH in the coupling of the amino acid derivative at Xaa$_4$. Final purified peptide: amorphous powder, 7 mg in yield in a synthesis scale of 0.4 mmol. HPLC analysis: $t_R$=18.15 min, purity 98.9%, gradient 5% B to 25% B over 20 min; MS (M+H$^+$): expected molecular ion mass 706.4, observed 706.4.

Example 13

Synthesis of Compound (13)

D-Phe-D-Phe-D-Leu-D-Nar-[N-(4-piperidinyl)-L-proline]-OH:

Synthesis was initiated from 0.4 mmol of the peptide resin, Boc-D-Phe-D-Phe-D-Leu-D-Dbu-N-(4-piperidinyl)-L-proline-[2-Cl-Trt resin], which was prepared during the synthesis of compound (12). The guanylation of the ω-amino function of D-Dbu at Xaa$_4$ was achieved according to the procedure described in the synthesis of compound (5), above. Subsequent cleavage and purification steps were carried out according to the procedure described in the synthesis of compound (1). Final purified peptide: amorphous powder, 7 mg in yield. HPLC analysis: $t_R$=18.68 min, purity 97.3%, gradient 5% B to 25% B over 20 min; MS (M+H$^+$): expected molecular ion mass 748.5, observed 748.5.

Example 14

Synthesis of Compound (14) D-Phe-D-Phe-D-Leu-D-Dap(amidino)-[N-(4-piperidinyl)-L-proline]-OH:

The compound was prepared according to the procedure described in the synthesis of compound (13) except that Fmoc-D-Dap(ivDde)-OH was substituted for Fmoc-D-Dbu (ivDde)-OH in the coupling of the amino acid derivative at Xaa$_4$. Final purified peptide: amorphous powder, 12 mg in yield in a synthesis scale of 0.4 mmol. HPLC analysis: $t_R$=18.55 min, purity 98.0%, gradient 5% B to 25% B over 20 min; MS (M+H$^+$): expected molecular ion mass 734.4, observed 734.4.

Example 15

Synthesis of Compound (15)

D-Phe-D-Phe-D-Leu-D-Lys-[4-Amidinohomopiperazine amide]:

The compound was prepared according to the procedure described in the synthesis of compound (1), except that methylation of the ω-amino function of D-Lys at Xaa$_4$ was omitted. Final purified peptide: amorphous powder, 140 mg in yield in a synthesis scale of 0.3 mmol. HPLC analysis: $t_R$=14.02 min, purity 99.3%, gradient 5% B to 25% B over 20 min; MS (M+H$^+$): expected molecular ion mass 678.4, observed 678.5.

Example 16

Synthesis of Compound (16)

D-Phe-D-Phe-D-Leu-D-Har-[4-Amidinohomopiperazine amide]:

The compound was prepared according to the procedure described in the synthesis of compound (1), except that a guanylation step was substituted for the methylation of the ω-amino function of D-Lys at Xaa$_4$. The guanylation was achieved according to the procedure described in the synthesis of compound (5), above. Final purified peptide: amorphous powder, 173 mg in yield in a synthesis scale of 0.3 mmol. HPLC analysis: $t_R$=15.05 min, purity 98.6%, gradient 5% B to 25% B over 20 min; MS (M+H$^+$): expected molecular ion mass 720.5, observed 720.5.

Example 17

Synthesis of Compound (17)

D-Phe-D-Phe-D-Leu-(ε-iPr)D-Lys-[4-Amidino-homopiperazine amide]:

The compound was prepared according to the procedure described in the synthesis of compound (1) except that an isopropylation step was substituted for the methylation of the ω-amino function of D-Lys at Xaa$_4$. The isopropylation was achieved according to the procedure described in the synthesis of compound (9). Final purified peptide: amorphous powder, 233 mg in yield in a synthesis scale of 0.3 mmol. HPLC analysis: $t_R$=16.16 min, purity 94.5%, gradient 5% B to 25% B over 20 min; MS (M+H$^+$): expected molecular ion mass 720.5, observed 720.5.

Example 18

Synthesis of Compound (18)

D-Phe-D-Phe-D-Leu-(β-amidino)D-Dap-[4-Amidinohomopiperazine amide]:

The compound was prepared according to the procedure described in the synthesis of compound (16) except for the substitution of Fmoc-D-Dap(ivDde)-OH for Fmoc-D-Lys(Dde)-OH in the coupling of the amino acid derivative at Xaa$_4$. Final purified peptide: amorphous powder, 155 mg in yield in a synthesis scale of 0.3 mmol. HPLC analysis: $t_R$=14.44 min, purity 99.1%, gradient 5% B to 25% B over 20 min; MS (M+H$^+$): expected molecular ion mass 678.4, observed 678.5.

Example 19

Synthesis of Compound (19)

D-Phe-D-Phe-D-Nle-(β-amidino)D-Dap-[4-Amidinohomopiperazine amide]:

The compound was prepared according to the procedure described in the synthesis of compound (18) above, except for the substitution of Fmoc-D-Nle-OH for Fmoc-D-Leu-OH in the coupling of the amino acid derivative at Xaa$_3$. Final purified peptide: amorphous powder, 190 mg in yield in a synthesis scale of 0.3 mmol. HPLC analysis: $t_R$=14.69 min, purity 98.9%, gradient 5% B to 25% B over 20 min; MS (M+H$^+$): expected molecular ion mass 678.2, observed 678.5.

Example 20

Synthesis of Compound (20)

D-Phe-D-Phe-D-Leu-(β-amidino)D-Dap-[homopiperazine amide]:

The compound was prepared according to the procedure described in the synthesis of compound (18) above, except that the guanylation of the homopiperazine at C-terminus was omitted. Final purified peptide: amorphous powder, 172 mg in yield in a synthesis scale of 0.3 mmol. HPLC analysis: $t_R$=13.84 min, purity 99.1%, gradient 5% B to 25% B over 20 min; MS (M+H$^+$): expected molecular ion mass 636.4, observed 636.5.

Example 21

Synthesis of Compound (21)

D-Phe-D-Phe-D-Nle-(β-amidino)D-Dap-[homopiperazine amide]:

The compound was prepared according to the procedure described in the synthesis of compound (19) except that the guanylation of the homopiperazine at C-terminus was omitted. Final purified peptide: amorphous powder, 149 mg in yield in a synthesis scale of 0.3 mmol. HPLC analysis: $t_R$=14.06 min, purity 98.5%, gradient 5% B to 25% B over 20 min; MS (M+H$^+$): expected molecular ion mass 636.4, observed 636.5.

Example 22

Synthesis of Compound (22)

D-Phe-D-Phe-D-Leu-D-Dbu-[4-Amidinohomopiperazine amide]:

The compound was prepared according to the procedure described in the synthesis of compound (15) except for the substitution of Fmoc-D-Dbu(ivDde)-OH for Fmoc-D-Lys(Dde)-OH in the coupling of the amino acid derivative at Xaa$_4$. Final purified peptide: amorphous powder, 152 mg in yield in a synthesis scale of 0.3 mmol. HPLC analysis: $t_R$=14.03 min, purity 98.1%, gradient 5% B to 25% B over 20 min; MS (M+H$^+$): expected molecular ion mass 650.4, observed 650.5.

Example 23

Synthesis of Compound (23)

D-Phe-D-Phe-D-Leu-D-Nar-[4-Amidinohomopiperazine amide]:

The compound was prepared according to the procedure described in the synthesis of compound (16) except for the substitution of Fmoc-D-Dbu(ivDde)-OH for Fmoc-D-Lys(Dde)-OH in the coupling of the amino acid derivative at Xaa₄. Final purified peptide: amorphous powder, 227 mg in yield in a synthesis scale of 0.3 mmol. HPLC analysis: $t_R$=14.37 min, purity 99.3%, gradient 5% B to 25% B over 20 min; MS (M+H⁺): expected molecular ion mass 664.4, observed 664.5.

Example 24

Synthesis of Compound (24)

D-Phe-D-Phe-D-Leu-D-Arg-[4-Amidinohomopiperazine amide]:

The compound was prepared by guanylation of the homopiperazine at C-terminus of Bcz-D-Phe-D-Phe-D-Leu-D-Arg-[homopiperazine amide], which was synthesized according to the procedure described in the synthesis of compound (7), described above. Subsequent cleavage and purification were carried out according to the procedure described in the synthesis of compound (1), above. Final purified peptide: amorphous powder, 102 mg in yield in a synthesis scale of 0.3 mmol. HPLC analysis: $t_R$=17.34 min, purity 98.4%, gradient 2% B to 22% B over 20 min; MS (M+H⁺): expected molecular ion mass 706.5, observed 706.5.

Example 25

Synthesis of Compound (25)

D-Phe-D-Phe-D-Leu-D-Lys-[2,8-diazaspiro[4,5]decan-1-one amide]:

These syntheses were carried out according to the scheme shown in FIG. 4. The intermediates described below correspond to those shown in FIG. 4. To a suspension of Boc-D-Phe-OH intermediate I-1 (7.96 g, 30.0 mmol), D-Leu-OBn p-TsOH intermediate I-2 (11.80 g, 30.0 mmol), HOBt monohydrate (4.46 g, 33.0 mmol) and DIEA (8.53 g, 66.0 mmol) in anhydrous THF (250 mL) cooled in an ice-water bath was added EDCI (6.33 g, 33.0 mmol) in four portions over 20 minutes with 5 minutes between each addition. The suspension was stirred overnight from a starting temperature of 0° C. to room temperature. After evaporation of THF, the residue was dissolved in ethyl acetate and washed sequentially with 10% citric acid, saturated NaHCO₃ and water. The organic phase was dried over sodium sulfate and evaporated under reduced pressure. The residue was dissolved in DCM, passed through a silica gel plug and eluted with 20% ethyl acetate in hexanes. The eluant was evaporated to give the pure product, Boc-D-Phe-D-Leu-OBn, intermediate I-3 (12.40 g, 88%) as a clear oil. LC-MS: m/z=469 (M+H).

Intermediate I-3 (12.40 g, 26.5 mmol) was dissolved in DCM (50 mL). TFA (25 mL) was added and the solution was stirred at room temperature for 2 hours. After evaporation of DCM and TFA, the residue was azeotroped with toluene twice to give the TFA salt of D-Phe-Leu-OBn, intermediate I-4. This crude dipeptide was suspended in THF, to which Boc-D-Phe-OH (6.36 g, 24 mmol), HOBt monohydrate (4.04 g, 26.4 mmol) and DIEA (8.7 mL, 50.0 mmol) was added at 0° C. EDCI (6.33 g, 6.4 mmol) was added in four portions over 20 minutes with 5 minutes between each addition. The suspension was stirred from 0° C. to room temperature overnight. After evaporation of THF, the residue was dissolved in ethyl acetate and washed sequentially with 10% citric acid, saturated NaHCO₃ and water. The organic phase was dried over sodium sulfate and evaporated under reduced pressure. The residue was recrystallized from 400 mL acetone/hexanes (1:3) to give 9.1 g pure product. The mother liquor was evaporated and again recrystallized from acetone/hexanes (1:3) to give 2.0 g product. The total yield was 11.1 g (68% for two steps). LC-MS: m/z=616 (M+H).

In a flask flushed with nitrogen was added wet palladium on carbon (1.8 g) and a solution of Boc-D-Phe-D-Phe-D-Leu-OBn, intermediate I-5 (11.1 g, 18.05 mmol) in methanol (50 mL). The mixture was stirred under a hydrogen balloon overnight. After filtration through celite, methanol was evaporated under reduced pressure. The residue was dissolved in acetone (20 mL) and slowly added to 500 mL water with 25 mL of 1N HCl under vigorous stirring. Pure product Boc-D-Phe-D-Phe-D-Leu-OH, intermediate I-6 was obtained by filtration 9.4 g (99%). LC-MS: m/z=526 (M+H).

To a solution of intermediate I-6 (2.06 g, 3.90 mmol), D-Lys(Boc)-OAll hydrochloride (1.26 g, 3.90 mmol) and DIEA (1.7 ml, 9.8 mmol) in DMF was added TBTU (1.56 g, 4.88 mmol) in three portions over 15 min at 0° C. After stirring overnight from a starting temperature of 0° C. to room temperature, DMF was evaporated under high vacuum. The crude reaction mixture was precipitate in 400 ml ice water and filtered to collect the precipitate, Boc-D-Phe-D-Phe-D-Leu-D-Lys(Boc)-OAll intermediate I-7 (2.60 g), which was used without further purification for the next step.

To a solution of intermediate I-7 (2.60 g, 3.3 mmol) in MeCN (75 mL) was added pyrrolidine (1.1 ml, 13.3 mmol) and palladium tetrakis(triphenylphosphine) (400 mg, 0.35 mmol) at 0° C. The reaction mixture was stirred at room temperature for 3 hours and evaporated to dryness. The residue was purified by reverse phase column chromatography with 30% MeCN/water to 90% MeCN/water to give the pure acid, intermediate I-8 (2.0 g, 80%) after evaporation of acetonitrile/water. LC-MS: m/z=754 (M+H).

To a solution of the acid, intermediate I-8 (150 mg, 0.20 mmol), the amine $HNR_aR_b$, 2,8-diazaspiro[4,5]decan-1-one (57 mg, 0.30 mmol) and DIEA (175 ul, 1.0 mmol) in DMF (5 mL) was added HBTU (11 3 mg, 3.0 mmol) at 0° C. After stirring overnight from a starting temperature of 0° C. to room temperature, DMF was evaporated under reduced pressure. The residue was stirred with 4N HCl in 1,4-dioxane (2.0 mL) at room temperature for 1 hour. After removal of dioxane, the residue was dissolved in water and purified by reverse phase column chromatography with a gradient of 10% MeCN/water to 60% MeCN/water in 30 minutes to give pure product, compound (25) (108 mg, 78% yield for the two steps) after evaporation of solvent. LC-MS: m/z=690 (M+H).

Example 26

Synthesis of Compound (26)

D-Phe-D-Phe-D-Leu-D-Lys-[2-methyl-2,8-diazaspiro[4,5]decan-1-one amide]:

Compound (26) was prepared essentially as described for compound 25, above except that the amine ($HNR_aR_b$ in the scheme of FIG. 4) in the final amide coupling step was 2-methyl-2,8-diazaspiro[4,5]decan-1-one in place of 2,8-diazaspiro[4,5]decan-1-one. LC-MS: m/z=704 (M+H).

Example 27

Synthesis of Compound (27)

D-Phe-D-Phe-D-Leu-D-Lys-[1,3,8-triazaspiro[4,5]decane-2,4-dione amide]:

Compound (27) was prepared essentially as described for compound 25, above except that the amine 1,3,8-triazaspiro[4,5]decane-2,4-dione was used in the final step. LC-MS: m/z=705 (M+H).

Example 28

Synthesis of Compound (28)

D-Phe-D-Phe-D-Leu-D-Lys-[5-chloro-1-(piperidin-4-yl)-1H-benzo[d]imidazol-2(3)H-one amide]:

Compound (28) was prepared essentially as described above for compound 25, above except that the amine 5-chloro-1-(piperidin-4-yl)-1H-benzo[d]imidazol-2(3)H-one was used. LC-MS: m/z=394.

Example 29

Synthesis of Compound (29)

D-Phe-D-Phe-D-Leu-D-Lys-[morpholino(piperidin-4-yl)methanone amide]:

Compound (29) was prepared essentially as described above for compound 25, above except that the amine morpholino(piperidin-4-yl)methanone was used. LC-MS: m/z=366.

Example 30

Synthesis of Compound (30)

D-Phe-D-Phe-D-Leu-D-Lys-[4-phenyl-1-(piperidin-yl-1H-imidazol-2(3H)-one amide]:

Compound (30) was prepared essentially as described above for compound 25, above except that the amine 4-phenyl-1-(piperidin-yl-1H-imidazol-2(3H)-one was used. LC-MS: m/z=779 (M+H).

Example 31

Synthesis of Compound (31)

D-Phe-D-Phe-D-Leu-D-Lys[4-(3,5-dimethyl-4H-1,2,4-triazol-4-yl)piperidine amide]:

Compound (31) was prepared essentially as described above for compound 25, above except that the amine 4-(3,5-dimethyl-4H-1,2,4-triazol-4-yl)piperidine was used. LC-MS: m/z=716 (M+H).

Example 32

Synthesis of Compound (32)

D-Phe-D-Phe-D-Leu-D-Lys-[1-(piperidin-4-yl)indolin-2-one amide]:

Compound (32) was prepared essentially as described above for compound 25, above except that the amine 1-(piperidin-4-yl)indolin-2-one was used. LC-MS: m/z=752 (M+H).

Example 33

Synthesis of Compound (33)

D-Phe-D-Phe-D-Leu-D-Lys-[1-phenyl-1,3,8-triazaspiro[4.5]decan-4-one amide]:

Compound (33) was prepared essentially as described above for compound 25, above except that the amine 1-phenyl-1,3,8-triazaspiro[4.5]decan-4-one was used. LC-MS: m/z=767 (M+H).

Example 34

Synthesis of Compound (34)

D-Phe-D-Phe-D-Leu-D-Lys-[imidazo[1,2-a]pyridine-2-ylmethanamine amide]:

Compound (34) was prepared essentially as described above for compound 25, above except that the amine imidazo[1,2-a]pyridine-2-ylmethanamine was used. LC-MS: m/z=683 (M+H).

Example 35

Synthesis of Compound (35)

D-Phe-D-Phe-D-Leu-D-Lys-[(5-methylpyrazin-2-yl)methylamine amide]:

Compound (35) was prepared essentially as described above for compound 25, above except that the amine (5-methylpyrazin-2-yl)methanamine was used in the final step. LC-MS: m/z=659 (M+H).

Example 36

Synthesis of Compound (36)

D-Phe-D-Phe-D-Leu-D-Lys-[1-(piperidin-4-yl)-1H-benzo[d]imidazol-2(3H)-one amide]:

Compound (36) was prepared essentially as described above for compound 25, above except that the amine 1-(piperidin-4-yl)-1H-benzo[d]imidazol-2(3H)-one was used. LC-MS: m/z=753 (M+H).

Example 37

Synthesis of Compound (37)

D-Phe-D-Phe-D-Leu-D-Lys-[4,5,6,7-tetrahydro-1H-pyrazolo[4,3-c]pyridine amide]:

Compound (37) was prepared essentially as described above for compound 25, above except that the amine 4,5,6,7-tetrahydro-1H-pyrazolo[4,3-c]pyridine was used. LC-MS: m/z=659 (M+H).

Example 38

Confirmation of Structures of Synthetic Peptide Amides 1-24

Table I shows the calculated molecular weight of the molecular ion, MH$^+$ for each compound and the actual molecular weight observed by mass spectrometry. Also shown is the type of synthetic phase used in the synthesis of each compound: solid phase, or mixed; and the type of resin used in the synthesis, whether a 2-chlorotrityl "2-Cl-Trt" resin, a hydrazinobenzoyl "hydrazine" resin, or a p-nitrophenyl-carbonate (Wang) "carbonate" resin. The number of the figure showing the relevant synthetic scheme for the synthesis of each compound is shown in the last column.

TABLE I

Synthesis and Confirmation of Structures of Compounds (1)-(24)

| COMPOUND | CALC'D MH+ | OBSERVED MH+ | SYNTH PHASE | RESIN | FIG. |
|---|---|---|---|---|---|
| 1 | 692.5 | 692.5 | mixed | Carbonate | 1 |
| 2 | 680.4 | 680.3 | solid | 2-Cl-Trt | 2 |
| 3 | 694.4 | 694.4 | solid | 2-Cl-Trt | 2 |
| 4 | 734.5 | 734.4 | solid | 2-Cl-Trt | 2 |
| 5 | 776.5 | 776.5 | solid | 2-Cl-Trt | 2 |
| 6 | 748.5 | 748.5 | solid | 2-Cl-Trt | 2 |
| 7 | 664.4 | 664.5 | solid | Carbonate | 1 |
| 8 | 722.4 | 722.5 | solid | 2-Cl-Trt | 2 |
| 9 | 722.5 | 722.5 | solid | 2-Cl-Trt | 2 |
| 10 | 680.4 | 680.4 | solid | hydrazine | 3 |
| 11 | 694.4 | 694.5 | solid | hydrazine | 3 |
| 12 | 706.4 | 706.4 | solid | 2-Cl-Trt | 2 |
| 13 | 748.5 | 748.5 | solid | 2-Cl-Trt | 2 |
| 14 | 734.4 | 734.4 | solid | 2-Cl-Trt | 2 |
| 15 | 678.4 | 678.5 | mixed | Carbonate | 1 |
| 16 | 720.5 | 720.5 | mixed | Carbonate | 1 |
| 17 | 720.5 | 720.5 | mixed | Carbonate | 1 |
| 18 | 678.4 | 678.5 | mixed | Carbonate | 1 |
| 19 | 678.4 | 678.5 | mixed | Carbonate | 1 |
| 20 | 636.4 | 636.5 | solid | Carbonate | 1 |
| 21 | 636.4 | 636.5 | solid | Carbonate | 1 |
| 22 | 650.4 | 650.5 | mixed | Carbonate | 1 |
| 23 | 692.4 | 692.5 | mixed | Carbonate | 1 |
| 24 | 706.5 | 706.5 | mixed | Carbonate | 1 |

Example 39

Inhibition of cAMP production by stimulation of endogenous mouse kappa-opioid receptor in R1.G1 cells Potency of the synthetic peptide amides as kappa-opioid receptor agonists was determined by measuring the inhibition of forskolin-stimulated adenylate cyclase activity. R1.G1 cells (a mouse thymoma cell line that expresses only the kappa-opioid receptor and no other opioid receptor subtype) were first exposed to forskolin (to induce cAMP) plus the synthetic peptide amide at the test concentration. After incubation, the cAMP level in the challenged R1.G1 cells was determined using a time resolved fluorescence resonance energy transfer (TR-FRET)-based cAMP immunoassay (LANCE™, Perkin Elmer). The detailed method is described below:

Mouse R1.G1 cells (ATCC, Manassas, Va.) were grown in suspension in high glucose-DMEM (Dulbecco's Modified Eagle's Medium, Cellgro, Herndon, Va.) containing 10% horse serum and 2% glutaMax (Invitrogen, Carlsbad. CA) without added antibiotics. On the day of the experiment, cells were spun at 1,000 rpm for 5 minutes at room temperature and then washed once with HBSS (HEPES Buffered Saline Solution, Invitrogen, Carlsbad, Calif.). Cells were then spun again and resuspended in stimulation buffer (HBSS with 0.05% FAF-BSA (Fatty acid-free bovine serum albumin, Roche Applied Science, Indianapolis, Ind.), 5 mM HEPES) to 2 million cells per ml. Antibody supplied with the LANCE™ cAMP immunoassay kit was then added to the cells according to the manufacturer's instructions, and 12,000 cells per well were then added to the wells containing forskolin to a predetermined fixed final concentration (typically about 2.5 uM) and the previously determined amount of the synthetic peptide amide to be tested. The synthetic peptide amides were tested in a range of concentrations to determine potency. Cells were incubated with the synthetic peptide amide plus forskolin for about 20 minutes at room temperature. After incubation, cells are lysed by adding 12 ul of detection mix as supplied with the LANCE™ kit, followed by incubation for one hour at room temperature. Time resolved fluorescence was read using a 330-380 nm excitation filter, a 665 nm emission filter, dichroic mirror 380, and Z=1 mm. A standard curve for cAMP concentration in this assay permitted determination of the amount of cAMP present in each well. A curve was produced by plotting synthetic peptide amide concentration against cAMP levels in the test cells, and subjected to non-linear regression using a four-parameter curve fitting algorithm to calculate the $EC_{50}$, the concentration of the synthetic peptide amide required to produce 50% of the maximal suppression of cAMP production by the synthetic peptide amide. Table II shows the $EC_{50}$ values obtained in this assay with synthetic peptide amide compounds (1) through (36).

TABLE II

Kappa Opioid Agonist Activity and Efficacy

| | mKOR | | hKOR | |
|---|---|---|---|---|
| Compound No. | $EC_{50}$ (nM) | Efficacy (%) | $EC_{50}$ (nM) | Efficacy (%) |
| (1) | 0.043 | 103 | 0.15 | 97 |
| (2) | 0.048 | 96 | 0.16 | 99 |
| (3) | 0.052 | 96 | 0.16 | 100 |
| (4) | 0.075 | 94 | 0.15 | 92 |
| (5) | 0.034 | 89 | 0.17 | 98 |
| (6) | 0.036 | 89 | 0.13 | 100 |
| (7) | 0.012 | 98 | 0.11 | 100 |
| (8) | 0.043 | 90 | 0.12 | 96 |
| (9) | 0.078 | 96 | 0.17 | 100 |
| (10) | 0.826 | 90 | 0.30 | 86 |
| (11) | 0.052 | 92 | 0.15 | 82 |
| (12) | 0.055 | 89 | 0.17 | 100 |
| (13) | 0.032 | 88 | 0.13 | 90 |
| (14) | 0.349 | 86 | 0.21 | 81 |
| (15) | 0.028 | 92 | 0.11 | 92 |
| (16) | 0.021 | 105 | 0.11 | 96 |
| (17) | 0.039 | 103 | 0.10 | 102 |
| (18) | 1.02 | 103 | 1.15 | 93 |
| (19) | 2.152 | 99 | nd | nd |
| (20) | 0.491 | 102 | 0.39 | 84 |
| (21) | 0.732 | 103 | 1.06 | 99 |
| (22) | 0.095 | 103 | 0.18 | 86 |
| (23) | 0.091 | 104 | 0.17 | 84 |
| (24) | 0.036 | 97 | 0.09 | 93 |
| (25) | 0.0314 | 82 | 0.0027 | 101 |
| (26) | 0.0194 | 86 | 0.0083 | 99 |
| (27) | 0.0056 | 87 | <0.001 | 88 |
| (28) | 0.0582 | 83 | 0.0083 | 100 |
| (29) | 0.0464 | 86 | 0.0145 | 100 |
| (30) | 0.1293 | 88 | 0.0116 | 95 |
| (31) | 0.0216 | 86 | 0.0042 | 95 |
| (32) | 0.0485 | 92 | 0.005 | 102 |
| (33) | 0.0767 | 86 | 0.0165 | 101 |
| (34) | 0.3539 | 90 | 0.0208 | 101 |
| (35) | 0.0359 | 86 | 0.0064 | 99 |
| (36) | 0.0234 | 87 | 0.0052 | 100 | nd - not determined;
mKOR and hKOR - mouse and human kappa opioid receptors

Example 40

Potency of Synthetic Peptide Amides on the Human Kappa Opioid Receptor

Human Embryonic Kidney cells (HEK-293 cells, ATCC, Manassas, Va.) in 100 mm dishes were transfected with transfection reagent, Fugene6 (Roche Molecular Biochemicals) and DNA constructs in a 3.3 to 1 ratio. The DNA constructs used in the transfection were as follows: (i) an expression vector for the human kappa opioid receptor, (ii) an expression vector for a human chimeric G-protein, and (iii) a luciferase reporter construct in which luciferase expression is induced by the calcium sensitive transcription factor NFAT.

The expression vector containing the human kappa opioid receptor was constructed as follows: The human OPRK1 gene was cloned from human dorsal root ganglion total RNA by PCR and the gene inserted into expression vector pcDNA3 (Invitrogen, Carlsbad, Calif.) to construct human OPRK1 mammalian expression vector pcDNA3-hOPRK1.

To construct the human chimeric G-protein expression vector, the chimeric G-protein Gαqi5 was first constructed by replacing the last 5 amino acids of human Gαq with the sequence of the last 5 amino acids of Gαi by PCR. A second mutation was introduced to this human Gαqi5 gene at amino acid position 66 to substitute a glycine (G) with an aspartic acid (D) by site-directed mutagenesis. This gene was then subcloned into a mammalian expression vector pcDNA5/FRT (Invitrogen) to yield the human chimeric G-protein expression vector, pcDNA5/FRT-hGNAq-G66D-i5.

To prepare the luciferase reporter gene construct, synthetic response elements including 3 copies of TRE (12-O-tetradecanoylphorbol-13-acetate-responsive elements) and 3 copies of NFAT (nuclear factor of activated T-cells) were incorporated upstream of a c-fos minimal promoter. This response element and promoter cassette was then inserted into a luciferase reporter gene vector pGL3-basic (Promega) to construct the luciferase reporter gene plasmid construct pGL3b-3TRE-3NFAT-cfos-Luc.

The transfection mixture for each plate of cells included 6 micrograms pcDNA3-hOPRK1, 6 micrograms of pcDNA5/FRT-hGNAq-G66D-15, and 0.6 micrograms of pGL3b-3TRE-3NFAT-cfos-Luc. Cells were incubated for one day at 37° C. in a humidified atmosphere containing 5% $CO_2$ following transfection, and plated in opaque 96-well plates at 45,000 cells per well in 100 microliters of medium. The next day, test and reference compounds were added to the cells in individual wells. A range of concentrations of test compounds was added to one set of wells and a similar range of concentrations of reference compounds was added to a set of control wells. The cells were then incubated for 5 hours at 37° C. At the end of the incubation, cells were lysed by adding 100 microliters of detection mix containing luciferase substrate (AMP (22 ug/ml), ATP (1.1 mg/ml), dithiothreitol (3.85 mg/ml), HEPES (50 mM final concentration), EDTA (0.2 mg/ml), Triton N-101 (4 ul/ml), phenylacetic acid (45 ug/ml), oxalic acid (8.5 ug/ml), luciferin (28 ug/ml), pH 7.8). Plates were sealed and luminescence read within 30 minutes. The concentration of each of the compounds was plotted against luminescence counts per second (cps) and the resulting response curves subjected to non-linear regression using a four-parameter curve-fitting algorithm to calculate the $EC_{50}$ (the concentration of compound required to produce 50% of the maximal increase in luciferase activity) and the efficacy (the percent maximal activation compared to full induction by any of the well-known kappa opioid receptor agonists, such as asimadoline (EMD-61753: See Joshi et al., 2000, *J. Neurosci.* 20(15):5874-9), or U-69593: See Heidbreder et al., 1999, *Brain Res.* 616(1-2):335-8).

Table II shows the $EC_{50}$ values obtained from the cAMP inhibition assay with the exemplified compounds synthesized according to the present invention and tested on mouse kappa opioid receptor (mKOR) with confirmatory replication of results on the human kappa opioid receptor (hKOR) by the above-described methods.

Synthetic peptide amides of the invention were tested in a similar assay for potency on the human mu opioid receptor. Each compound tested had an $EC_{50}$ for the human mu opioid receptor greater than or equal to 1 uM.

Example 41

Membrane Permeability of the Synthetic Peptide Amides

The Caco-2 cell line is a human colon adenocarcinoma cell line that differentiates in culture and is used to model the epithelial lining of the human small intestine. Compounds of the present invention were tested in a membrane permeability assay using the TC7 subclone of Caco-2 in a standard assay (Cerep, Seattle, Wash.). Briefly, the apparent permeability coefficient ($P_{app}$) was determined in the apical-to-basolateral (A-B) direction across cell monolayers cultured on 96-well polycarbonate membrane filters.

Compounds were tested at a concentration of 10 uM at pH 6.5 in 1% DMSO, with the recipient side maintained at pH 7.4. The assay plate was incubated for 60 minutes at 37° C. with gentle shaking. Samples were taken at time zero from the donor side and at the end of the incubation period from both the donor and recipient sides. Samples were analyzed by HPLC-MS/MS. The $P_{app}$- value (expressed as $10^{-6}$ cm/sec) was then calculated based on the appearance rate of compound in the recipient side. The $P_{app}$ was calculated with the equation:

$$P_{app} = \frac{1}{S \cdot C_0}\left(\frac{dQ}{dT}\right)$$

where $P_{app}$ is the apparent permeability; S is the membrane surface area, $C_0$ is the donor concentration at time 0, and dQ/dt is the amount of drug transported per time. Four reference compounds (labetalol, propranolol, ranitidine, and vinblastine) were concurrently tested to ensure the validity of the assay, as well as asimadoline, which is purported to be a peripherally acting kappa opioid. Results are shown in Table III.

TABLE III

| Membrane permeability | |
|---|---|
| Compound | Mean Permeability ($cm^{-6}$/sec) |
| (1) | <0.10 |
| (3) | <0.02 |
| (6) | <0.02 |
| Asimadoline | 37.5 |
| Labetalol | 9.9 |
| Propranolol | 53.8 |
| Ranitidine | 0.5 |
| Vinblastine | <0.2 |

Compounds that exhibit low permeability in this type of assay are believed to have reduced potential for crossing the blood-brain barrier in vivo, since high passive permeability appears to be a key feature of CNS-acting drugs (Mahar Doan et al. Passive permeability and P-glycoprotein-mediated efflux differentiate central nervous system (CNS) and non-CNS marketed drugs. *J Pharmacol Exp Ther.* 2002; 303: 1029-37).

Example 42

Inhibition of cytochrome $P_{450}$ oxidases

Inhibition of cytochrome $P_{450}$ oxidase isozymes CYP1A, CYP2C9, CYP2C19, CYP2D6 and CYP3A4 by synthetic peptide amide compounds of the invention was determined according to the following methods performed by Cerep (Seattle, Wash.):

In the cytochrome $P_{450}$ CYP1A assay, human liver microsomes (0.2 mg/ml protein) were incubated for 15 minutes at 37° C. with 10 uM test compound, 1 uM ethoxyresorufin, 1.3 mM NADP, 3.3 mM glucose-6-phosphate and 0.4 U/ml glucose-6-phosphate dehydrogenase. In the absence of test compound, the ethoxyresorufin added as substrate is oxidized to resorufin, and in the presence of an inhibitor of the CYP isozyme, the amount of resorufin produced is reduced. Furafylline was used as a reference inhibitor.

The cytochrome $P_{450}$ CYP2C9 assay reaction mixture containing human liver microsomes (0.2 mg/ml protein) was incubated for 15 minutes at 37° C. with 10 uM test compound, 10 uM tolbutamide, 1.3 mM NADP, 3.3 mM glucose-6-phosphate and 0.4 U/ml glucose-6-phosphate dehydrogenase. In the absence of test compound, the tolbutamide is oxidized to 4-hydroxytolbutamide, and in the presence of an inhibitor of the CYP isozyme, the amount of 4-hydroxytolbutamide produced is reduced. Sulfaphenazole ($IC_{50}$: 0.35 uM) was the reference inhibitor.

For the cytochrome $P_{450}$ CYP2C19 assay, human liver microsomes (0.2 mg/ml protein) were incubated for 15 minutes at 37° C. with 10 uM test compound, 10 uM omeprazole, 1.3 mM NADP, 3.3 mM glucose-6-phosphate and 0.4 U/ml glucose-6-phosphate dehydrogenase. In the absence of test compound, the omeprazole is oxidized to 5-hydroxy-omeprazole, and in the presence of an inhibitor of the CYP isozyme, the amount of 5-hydroxy-omeprazole produced is reduced. Oxybutinin ($IC_{50}$: 7.1 uM) was the reference inhibitor.

The cytochrome $P_{450}$ CYP2D6 assay reaction containing human liver microsomes (0.2 mg/ml protein) was incubated for 15 minutes at 37° C. with 10 uM test compound, 5 uM dextromethorphan, 1.3 mM NADP, 3.3 mM glucose-6-phosphate and 0.4 U/ml glucose-6-phosphate dehydrogenase. In the absence of test compound, the dextromethorphan is oxidized, and in the presence of an inhibitor of the CYP isozyme, the amount of oxidation product is reduced. Quinidine ($IC_{50}$: 0.093 uM) was the reference inhibitor.

For the cytochrome $P_{450}$ CYP2C19 assay, human liver microsomes (0.2 mg/ml protein) were incubated for 20 minutes at 37° C. with 10 uM test compound, 5 uM midazolam, 1.3 mM NADP, 3.3 mM glucose-6-phosphate and 0.4 U/ml glucose-6-phosphate dehydrogenase. In the absence of test compound, the midazolam is oxidized, and in the presence of an inhibitor of the recombinant isozyme, the amount of oxidation product is reduced. The oxidation product is determined from the area under the curve after HPLC-MS/MS separation. Ketoconazole ($IC_{50}$: 0.55 uM) was the reference inhibitor.

In each assay, the percent inhibition of the cytochrome $P_{450}$ CYP $P_{450}$ isozyme was determined as one hundred times the ratio of (1−the amount of product in the sample in the presence of the test compound) divided by the amount of product in the sample containing untreated isozyme. The results of duplicate assays (expressed as percent remaining CYP activity) are shown in Table IV.

TABLE IV

Percent Activity of Cytochrome $P_{450}$ CYP Isozymes

| $P_{450}$ isozyme | Compound | | |
|---|---|---|---|
| | (1) | (3) | (6) |
| CYP1A | 89.8 | 93.1 | 89.5 |
| CYP2C9 | 93.2 | 97.4 | 92.1 |
| CYP2C19 | 98.5 | 103.2 | 97.2 |
| CYP2D6 | 96.0 | 99.5 | 93.9 |
| CYP3A4 | 92.5 | 94.3 | 93.6 |

Example 43

Stability of Compound (2) to Human Liver Microsomes

Microsomes from human liver (final concentration 0.3 mg/mL protein) in 0.1M phosphate buffer pH7.4 and NADPH regenerating system (1 mM NADP, 5 mM glucose-6-phosphate, and 1 Unit/mL glucose-6-phosphate dehydrogenase) were pre-incubated at 37° C. prior to the addition of substrate, compound (2) to give a final substrate concentration of 1 µM; and a final methanol concentration of 0.6%. Aliquots were removed at 0 and 60 minutes. An equal volume of 50/50 acetonitrile/methanol was added, samples were centrifuged, and the amount of compound remaining in the supernatant was measured via HPLC coupled with tandem mass spectrometry by comparison of peak areas generated from the 0 and 60 minute samples. Duplicate samples showed 96% and 118% of compound (2) remaining after 60 minutes incubation with human liver microsomes.

Example 44

Pharmacokinetics of Compound (2) in Rat

Figure 5:
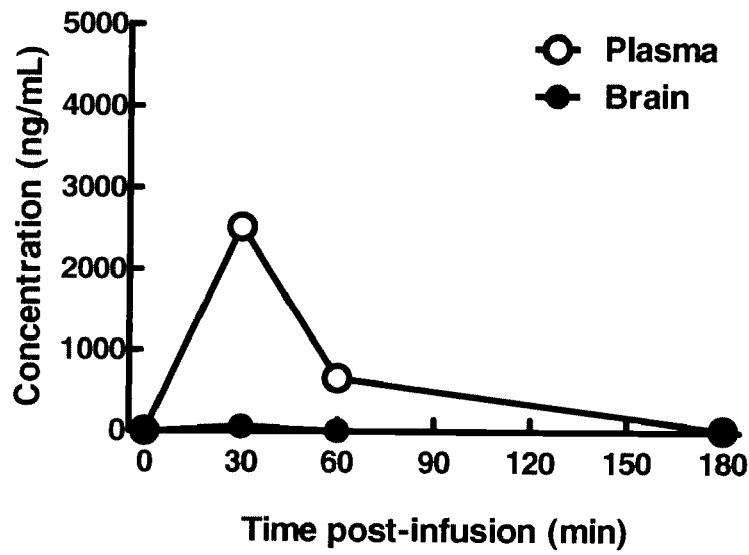
FIG. 5: Concentration detected in plasma and brain of rats after administration of 3 mg/kg compound (2) over a 5 minute infusion period through a jugular vein catheter. Concentration of compound (2) in ng/ml: open circles: plasma, solid circles: brain.

To determine brain to plasma concentration ratios of compound (2), a group of 6 conscious jugular vein catheterized rats were administered 3 mg/kg of peptide over a 5 minute infusion period into the jugular vein catheter. Thirty, 60 and 180 minutes following the start of infusion, blood samples were collected from 2 animals at each time point by terminal cardiac puncture and whole brains were rapidly removed. Plasma was isolated by centrifugation. Tandem liquid chromatography mass spectrometry (LC-MS/MS) was used to quantify the concentration of drug in rat plasma and brain. Results are shown in FIG. 5.

Example 45

Pharmacokinetics of Compound (6) in Mice and Cynomolgus Monkeys

Figure 6:
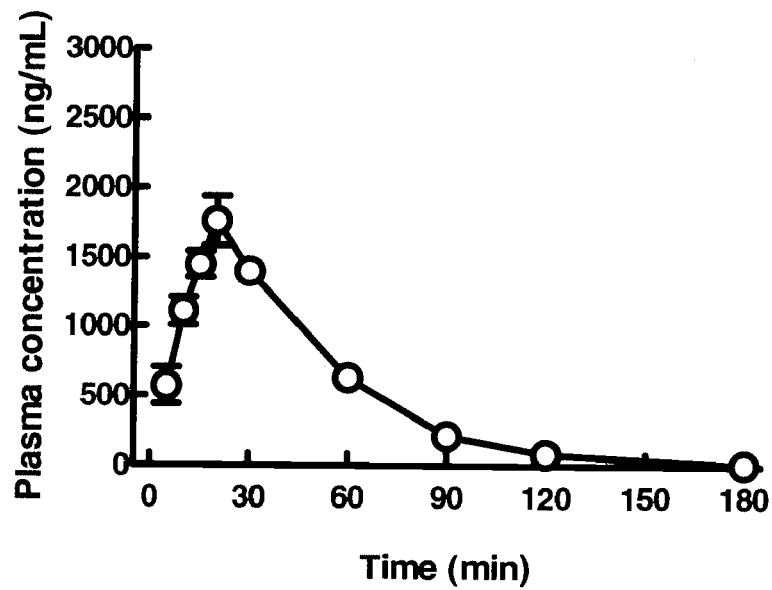
FIG. 6: Plasma concentrations of compound (6) after subcutaneous administration of a single bolus of 1 mg/kg of the compound to ICR mice. Plasma was sampled at 5, 10, 15, 20, 30 60, 90 120, and 180 minutes post-injection.

A single bolus of the synthetic peptide amide compound was administered by subcutaneous injection to ICR mice (n=6, males, body wt 23-37 g, Charles River, Wilmington, Mass.) and plasma samples taken at 5, 10, 15, 20, 30 60, 90, 120, and 180 minutes post-injection. FIG. 6 shows the results obtained after subcutaneous injection of a 1 mg/kg dose of compound (6) in ICR mice. The "half life" for this study was determined as the time required for the plasma concentration to fall by 50% after maximum concentration in the plasma was achieved; the computed elimination half-life, based on the elimination rate constant of the slowest elimination phase, is expected to be longer. See Table V below.

Example 46

Synthetic Peptide Amide Compound Pharmacokinetcs in Monkeys

Samples were administered to male monkeys, *Macaca fascicularis* (SNBL USA, Ltd., Everett, Wash., purpose-bred cynomolgus monkeys, closely related to humans, both phylogenetically and physiologically), aged 3-7 years and weighing 3-5 kilograms. Samples were administered in a superficial vein of the arm or leg (e.g. brachial, or saphenous) in 0.9% saline for injection, USP (Baxter Healthcare, Deerfield, Ill.) as follows: A sample containing 4 mg of compound (6) of the present invention to be tested was prepared in 2 ml 0.9% saline for injection. The 2 ml dose was administered as an intravenous bolus to the test animal, resulting in a dose of approximately 0.4 to 0.65 mg/kg, depending on the body weight of the animal. Blood samples of 0.6 ml were collected by venipuncture from a peripheral vein at 2, 5, 10, 15 and 30 minutes post dose injection, and then at 1, 2 and 4 hours. Each sample was placed in a pre-chilled glass test tube containing lithium heparin and immediately chilled on ice. Plasma was collected after centrifugation at 2,000 g for fifteen minutes at 2-8° C. The plasma layers of each sample were transferred to polypropylene tubes and stored frozen at −60° C. or lower until assayed.

One hundred microliter aliquots of thawed plasma were spiked with 5 microliters of a 400 ng/ml solution of an appropriate internal standard (in this case a known standard synthetic peptide amide compound) in 0.1% TFA, and the proteins were precipitated with 100 microliters of 0.1% TFA in acetonitrile. The samples were centrifuged at 1000×g for 5 minutes and the supernatants analyzed by LC-MS. LC-MS analysis was performed on a Finnigan LCQ Deca mass spectrometer interfaced to a Surveyor HPLC system (Thermo Electron Corporation, Waltham, Mass., USA). HPLC analysis was performed on 2.1×150 mm C18 reversed phase columns with a gradient of 0.01% TFA in acetonitrile in 0.01% TFA in water. Mass detection was performed in the selected reaction monitoring mode (SRM).

Quantitation was performed against a calibration curve of the analyte in blank Cynomolgus monkey plasma using the same internal standard. Data analysis and the extraction of pharmacokinetic parameters were performed with the program PK Solutions 2.0 (Summit Research Services, Ashland, Ohio, USA). Table V, below shows the half life in ICR mice after subcutaneous injection of compound (6) and the half life for this compound after intravenous bolus administration in cynomolgus monkeys.

TABLE V

In vivo half life of synthetic peptide amide compound (6)

| | ICR Mice | Cynomolgus Monkeys |
|---|---|---|
| Administration Route | subcutaneous | intravenous |
| Half Life (min) | 22.0 | 58.6 |

*Compound (6) in D-Phe-D-Phe-D-Leu-(ε-Me)D-Lys-[N-(4-piperidinyl)-L-proline]-OH

Figure 7:
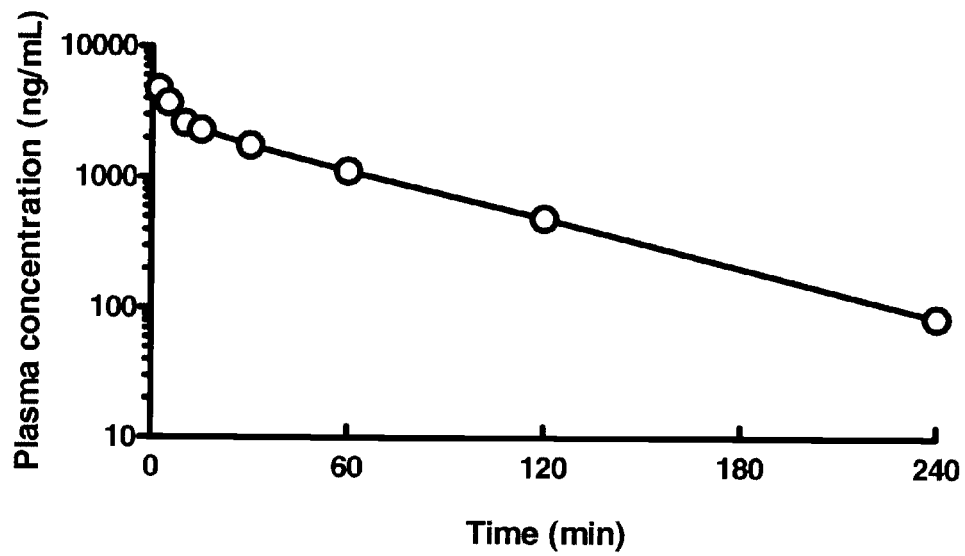
FIG. 7: Plasma concentrations of compound (3) after intravenous administration of a single bolus of 0.56 mg/kg of the compound to cynomolgus monkeys. Plasma was sampled at 2, 5, 10, 15, 30, 60, 120, and 240 minutes post injection.

Persistence of compound (3) in the plasma of cynomolgus monkeys after intravenous administration of a bolus of 0.56 mg/kg is shown in FIG. 7.

Example 47

Acetic Acid-Induced Writhing Assay in Mice

This test identifies compounds which exhibit analgesic activity against visceral pain or pain associated with activation of low pH-sensitive nociceptors [see Barber and Gottschlich (1986) *Med. Res. Rev.* 12: 525-562; Ramabadran and Bansinath (1986) *Pharm. Res.* 3: 263-270]. Intraperitoneal administration of dilute acetic acid solution causes a writhing behavior in mice. A writhe is defined as a contraction of the abdominal muscles accompanied by an extension of the forelimbs and elongation of the body. The number of writhes observed in the presence and absence of test compounds is counted to determine the analgesic activity of the compounds.

Each day a writhing assay was performed, a vehicle control group of mice (n=6-8) that were treated identically to the test group (except that test compound was omitted from the injection dose) was always included and the average total number of writhes in this group used as the absolute reference point defining 0% decrease in pain perception for all other mice receiving a test compound on that day. Specifically, the total number of writhes of each mouse receiving the test compound was converted to % decrease in pain perception according to the following equation:

$$\% \text{ decrease in pain perception} = \frac{(W_v - W_c)}{W_v} \times 100$$

Where $W_v$ is the mean number of writhes in vehicle-treated group and $W_c$ is the number of writhes in compound-treated mouse. The data were analyzed using the 2-parameter Hill's equation (also known as the Emax model), where Emax is assumed to be 100% antinoci-perception (i.e., no writhes over the 15 min post-acetic acid administration).

Male ICR mice, 23-37 grams in weight, were weighed and placed in individual observation chambers (usually a 4000 ml glass beaker) with a fine layer of SANI-CHIPS rodent bedding at the bottom. To determine the activity and potency of test compounds, different doses of the compound solution or vehicle were injected subcutaneously in the back of the neck 15 or 180 minutes prior to administration of acetic acid solution. After administration of the compound or vehicle control, mice were returned to their individual observation chambers awaiting the intraperitoneal administration of acetic acid solution. Fifteen minutes or three hours later, according to the interval time defined in each experiment between compound delivery and acetic acid injection, a dose corresponding to 10 ml/kg of a 0.6% (v/v) acetic acid solution was then injected into the right lower quadrant of the abdomen. Immediately after the injection, the mouse was returned to its observation chamber and the recording of the number of writhes begun immediately. The number of writhes was counted over a 15-min period starting from the time of acetic acid injection, the data being collected over three separate 5 minute time periods (0-5 min, 5-10 min, and 10-15 min).

Figure 8:
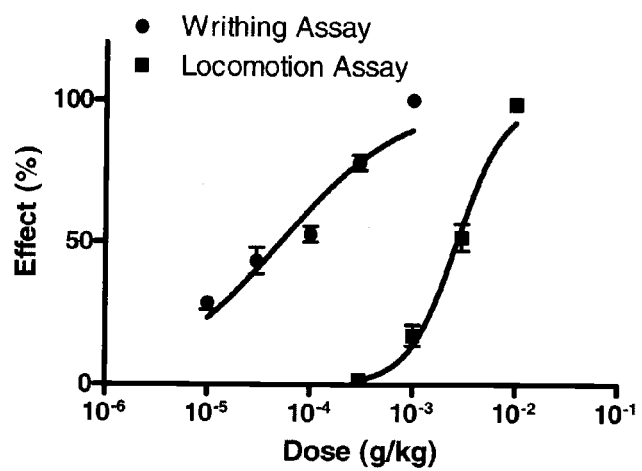
FIG. 8: Dose-response curves for compound (3) in ICR mice in the acetic acid-induced writhing assay (solid circles) and in the locomotion assay (solid squares).

The data were reported as $ED_{50}$, and Hill coefficient. The $ED_{50}$ is expressed either as mean±standard error of the mean (sem) ($ED_{50}$+/−sem) or as geometric mean with 95% confidence intervals (95% CI) using t-scores. The Hill coefficient is expressed as the arithmetic mean±sem calculated from the values obtained from the animals. Results for compound (2) are shown in FIG. 8 (solid circles).

For dose-response analysis, raw data were converted to % maximum possible effect (% MPE) using the formula: % MPE=((test score−vehicle-treated score)/(0−vehicle-treated score))* 100. Raw data were analyzed using a one-way ANOVA followed by Dunnett's post-tests. The dose which elicited 50% attenuation of hypersensitivity ($ED_{50}$) was determined using linear regression analysis. Compounds were administered by the intravenous route. Table VI summarizes the results of these experiments.

TABLE VI

Effects of Compounds (2) and (5) on Acetic Acid-Induced Writhing in Mice.

| Compound | $ED_{50}$ (mg/kg, iv, 15 min post-dose) | % MPE (180 min post-$ED_{90}$) | % MPE (240 min post-$ED_{90}$) | % MPE (300 min post-$ED_{90}$) |
|---|---|---|---|---|
| (2) | 0.07 (0.06-0.1) | 77 ± 5% | 81 ± 4% | 84 ± 4% |
| (5) | 0.01 (0.01-0.02) | 54 ± 10% | NT | NT |

NT = not tested

Figure 9:
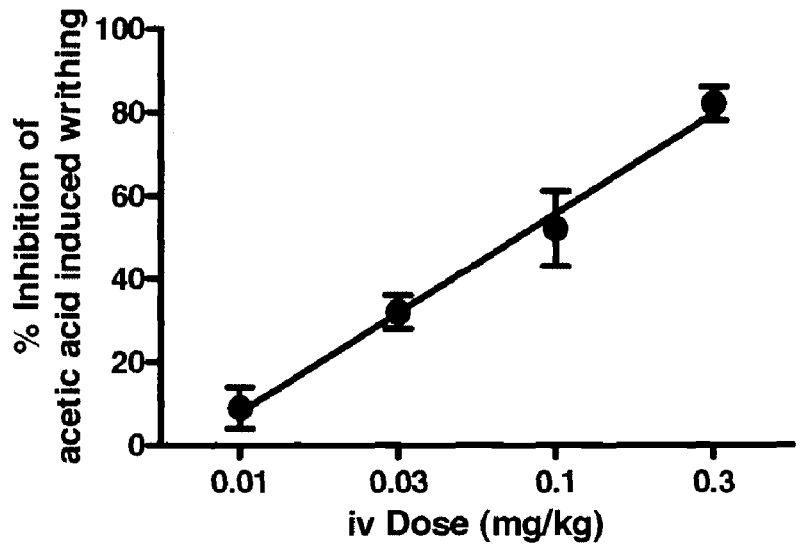
FIG. 9: Dose response of compound (2)-mediated suppression of acetic acid-induced writhing in mice when delivered by the intravenous route.

A dose response for compound (2) in the acetic acid-induced writhing model in mice was generated using 0.01, 0.03, 0.1 and 0.3 mg/kg administered intravenously as described above. Using the above method a linear dose response relationship was determined for compound (2) for doses ranging from 0.01 mg/kg to 0.3 mg/kg, as shown in FIG. 9.

Example 48

Inhibition of Locomotion in Mice to Measure Sedation by Compounds After Subcutaneous Injection (Locomotion Reduction Assay)

Compounds which exhibit sedative activity inhibit the spontaneous locomotion of mice in a test chamber. To determine the potential sedative effect of test compounds, the extent of locomotion reduction after the administration of the test compound or vehicle control can be determined and compared with a specialized apparatus designed for this purpose (Opto-Varimex Activity Meter). At the start of each experiment, each mouse was weighed and examined to determine good health. To determine the activity and potency of compounds, different doses of the compound solution or vehicle were injected subcutaneously 15 or 180 minutes prior to initiation of data collection. The subcutaneous injection was performed in the back of the neck of the mouse, pinched in a "tent" to allow proper access for the syringe needle. After injection, each animal was placed individually in Plexiglas boxes (43 cm×43 cm) inside the Opto-Varimex Activity Meter apparatus. Before the animal was placed in the apparatus, a thin layer of SANI-CHIPS rodent bedding was placed on the bottom of the Plexiglas box to provide a comfortable environment. Each Opto-Varimex Activity Meter apparatus was then turned on and data acquisition begun by the ATM3 Auto-Track System. The data were processed and results expressed in the same way as described for the writhing assay data in Example 47.

Example 49

Analgesic Effect vs. Sedative Effect of Synthetic Peptide Amide (3)

Inhibition of acetic acid-induced writhing by a compound is an indication of an analgesic effect (also called an antinociceptive effect). Similarly, a reduction in locomotion caused by administration of the compound can be used as a measure of its general sedative effect.

The $ED_{50}$ determined in the acetic acid-induced writhing assay in ICR mice was 52 ug/kg when synthetic peptide amide (3) was administered subcutaneously as described in Example 34 and shown in FIG. 8 (solid circles). The $ED_{50}$ value determined in the inhibition of locomotion assay as described in Example 35 was 2685 ug/kg for the same synthetic peptide amide administered subcutaneously. See FIG. 8 (solid squares). The therapeutic ratio of the analgesic effect over the sedative effect is the fold higher $ED_{50}$ required to achieve a sedative effect as compared to the $ED_{50}$ required to achieve an analgesic effect. Thus, compound (3) exhibits a (2685/52) fold ratio, i.e. 51.6 fold. Thus, the therapeutic ratio is approximately 52 fold for compound (3).

Example 50

Spinal Nerve Ligation (SNL) Model

Figure 10:
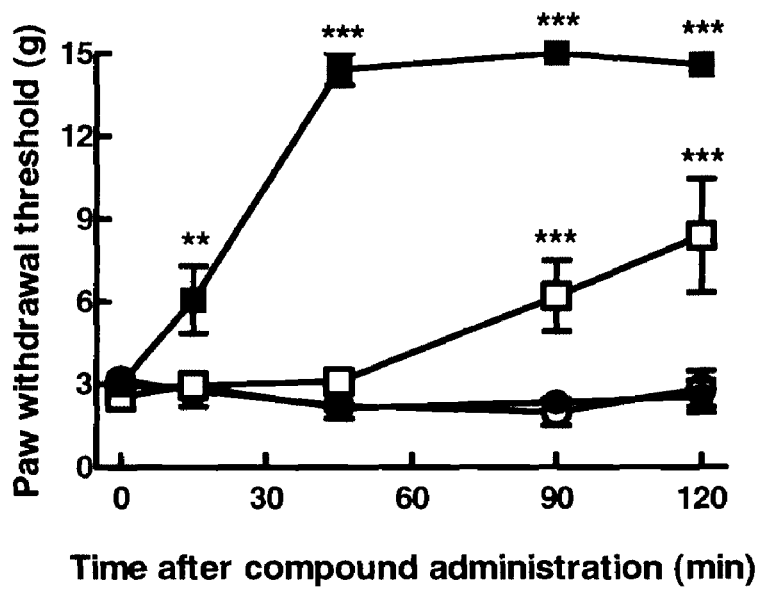
FIG. 10: Effects of compound (2) on mechanical hypersensitivity induced by L5/L6 spinal nerve ligation in rats. Open circles—vehicle alone; Solid circles—compound (2) at 0.1 mg/kg; open squares—compound (2) at 0.3 mg/kg; solid squares—compound (2) at 1.0 mg/kg.  denotes p<0.01; * denotes p<0.001 vs. Vehicle (2 Way ANOVA, Bonferroni).

The SNL model (Kim and Chung 1992) was used to induce chronic neuropathic pain. The rats were anesthetized with isoflurane, the left L5 transverse process was removed, and the L5 and L6 spinal nerves were tightly ligated with 6-0 silk suture. The wound was then closed with internal sutures and external staples. Fourteen days following SNL, baseline, post-injury and post-treatment values for non-noxious mechanical sensitivity were evaluated using 8 Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al. 1994). Animals were placed on a perforated metallic platform and allowed to acclimate to their surroundings for a minimum of 30 minutes before testing. The mean and standard error of the mean (SEM) were determined for each paw in each treatment group. Since this stimulus is normally not considered painful, significant injury-induced increases in responsiveness in this test are interpreted as a measure of mechanical allodynia. The dose which elicited 50% attenuation of mechanical hypersensitivity ($ED_{50}$) was determined using linear regression analysis. Compound (2) was administered by the intravenous route. FIG. 10 summarizes the results of these experiments. The calculated $ED_{50}$ for compound (2) in this model was 0.38 mg/kg (0.31-0.45; 95% confidence interval).

Example 51

Ocular Analgesia Induced by Compounds (2), (3) and (4)

Ocular analgesia was evaluated by instilling five volumes of the test compound, 50 microliters each in physiological saline, at the concentration to be tested into the right eye of naïve albino New Zealand strain rabbits within a period of twenty minutes. Fifteen minutes after the last instillation of the test compound, each animal was administered a single instillation of 30 microliters of 10 mg/ml capsaicin (33 mM) in the treated eye. Capsaicin is known to induce corneal pain. Corneal pain was evaluated by measurement of the palpebral opening measured in millimeters using a transparent ruler over the treated and untreated eyes. In this animal model, the reduction in size of the palpebral opening after instillation of capsaicin is an indication of the degree of ocular pain. Thus, any observed restoration (increase) in size of the palpebral opening after treatment with test compound is taken as a measure of relief from capsaicin-induced ocular pain.

These evaluations were performed before treatment with the test compound (pre-test), immediately prior to the instillation of capsaicin, and then 1, 5, 10, 15, 20, 25, 30, 40, 50 and 60 minutes following the instillation of capsaicin. Table VII shows the mean of palpebral opening measurements (relative to the untreated eye expressed as percent of control) averaged over the period from 10-30 minutes after capsaicin instillation in rabbits pre-instilled with a kappa opioid agonist of the invention and after preinstillation with a standard concentration of diltiazem, a benzothiazepine calcium channel blocker with local anesthetic effects. See Gonzalez et al., (1993) *Invest. Ophthalmol. Vis. Sci.* 34: 3329-3335.

TABLE VII

Effect of compounds (2), (3) and (4) in reducing ocular pain

| Compound | Time (post capsaicin) | Mean (% Control) | SEM (% Control) |
| --- | --- | --- | --- |
| None (Saline) | 10-30 min. | 61.2 | 6.5 |
| Diltiazem at 10 mM | 10-30 min. | 74.6 | 5.5 |
| (2) at 10 mg/ml | 10-30 min. | 82.7 | 5.3 |
| (3) at 10 mg/ml | 10-30 min. | 76.0 | 5.2 |
| (4) at 10 mg/ml | 10-30 min. | 56.7 | 8.4 |

Mean is of five animals; SEM: Standard error of the mean

Example 52

Dose Response of Compound (2) in Capsaicin-Induced Ocular Pain

Ocular analgesia induced by Compound (2) at several concentrations instilled into the right eye of naïve albino New Zealand strain rabbits was evaluated as described above. Results were compared with analgesia induced by 10 mg/ml morphine (a non-selective opioid agonist) as a systemic active control, and with 10 mM diltiazem as a topical active-control in the same experiment and under the same conditions. Table VIII below shows the accumulated results.

TABLE VIII

Dose-Response of Compound (2) in Capsaicin-Induced Ocular Pain

| Compound | Time (post capsaicin) | Mean (% Control) | SEM (% Control) |
| --- | --- | --- | --- |
| Morphine at 10 mg/ml | 10-30 min. | 74.8 | 11.1 |
| Diltiazem at 10 mM | 10-30 min. | 77.6 | 7.4 |
| (2) at 1 mg/ml | 10-30 min. | 60.5 | 9.9 |
| (2) at 10 mg/ml | 10-30 min. | 56.6 | 9.3 |
| (2) at 25 mg/ml | 10-30 min. | 75.5 | 7.1 |
| (2) at 50 mg/ml | 10-30 min. | 87.5 | 4.8 |

Mean is of ten animals; SEM: Standard error about the mean

Example 53

Effect of Compound (2) in a Rat Pancreatitis Model

Chronic pancreatic inflammation was induced in rats by intravenous administration of dibutylin dichloride (DBTC, Aldrich Milwaukee, Wis.) dissolved in 100% ethanol at a dose of 8 mg/kg under isofluorane anesthesia (2-3 liters/min, 4%/vol until anesthetized, then 2.5%/vol throughout the procedure. Control animals received the same volume of vehicle (100% ethanol) alone. Pancreatitis pain was assessed by determination of abdominal sensitivity to probing the abdomen of rats with a calibrated von Frey filament (4 g). Rats were allowed to acclimate in suspended wire-mesh cages for 30 min before testing. A response was indicated by the sharp withdrawal of the abdomen, licking of abdominal area, or whole body withdrawal. A single trial consisted of 10 applications of von Frey filament applied once every 10 s to allow the animal to cease any response and return to a relatively inactive position. The mean occurrence of withdrawal events in each trial is expressed as the number of responses to 10 applications. Rats without inflammation of the pancreas typically display withdrawal frequencies to probing with von Frey filament of 0-1. The animals were allowed to recover for 6 days after DBTC administration prior to any pharmacological manipulations. Animal not demonstrating sufficient abdominal hypersensitivity (i.e., rats with less than 5 positive responses out of a possible 10) were excluded from the study.

Figure 11:
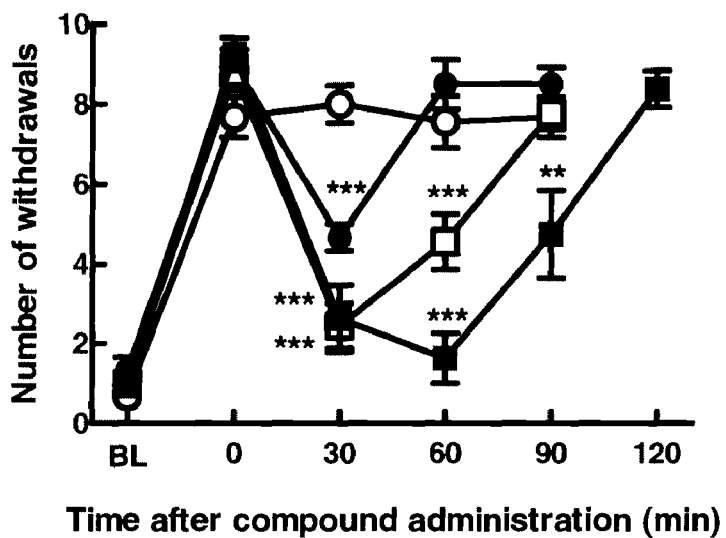
FIG. 11: Effect of Compound (2) at different concentrations on pancreatitis-induced abdominal hypersensitivity in rats. Dibutylin dichloride or vehicle alone was administered intravenously and hypersensitivity assessed by abdominal probing with a von Frey filament at 30 minute intervals. Hypersensitivity is expressed as number of withdrawals from ten probings. Open circles—vehicle alone; solid circles—compound (2) at 0.1 mg/kg; open squares—compound (2) at 0.3 mg/kg; solid squares—compound (2) at 1.0 mg/kg.  denotes p<0.01; * denotes p<0.001 vs. Vehicle (2 Way ANOVA, Bonferroni).

The number of positive responses, following abdominal probing (out of a possible 10), were recorded at each time point. Data are presented as average number of withdrawals (±SEM) for each dosing group at each corresponding time point. For dose-response analysis, raw data were converted to % maximum possible effect (% MPE) using the formula: % MPE=((test score−post DBTC score)/(pre DBTC score−post DBTC score))*100. Raw data were analyzed using a two-way repeated measures ANOVA followed by Bonferroni post-tests. The dose which elicited 50% attenuation of hypersensitivity ($ED_{50}$) was determined using linear regression analysis. Compounds were administered by the intraperitoneal route. FIG. 11 summarizes the results of these experiments. The calculated $ED_{50}$ for compound (2) in this model was 0.03 mg/kg (0.006-0.14; 95% confidence interval).

Figure 12:
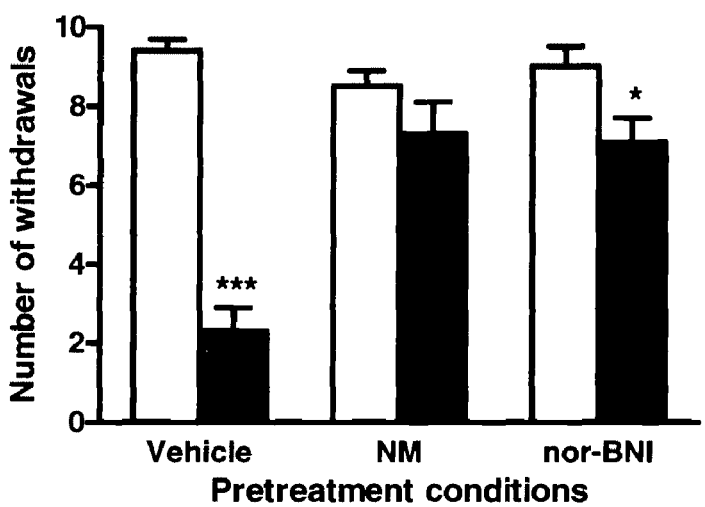
FIG. 12: Blocking of the effect of compound (2) on pancreatitis-induced abdominal hypersensitivity by nor-BNI and naloxone methiodide in rats. Open column—vehicle alone, solid column—compound (2) at 1 mg/kg with naloxone methiodide or norBNI as indicated. *** denotes p<0.001 vs. Vehicle+Vehicle (2 Way ANOVA, Bonferroni).

To determine if the efficacy of Compound (2) (1 mg/kg) is mediated via activation of peripheral kappa opioid receptors, groups of eight rats were pretreated with either the selective kappa opioid receptor antagonist nor-BNI (1 mg/kg), or with a non-selective opioid receptor antagonist, naloxone methiodide (10 mg/kg), which does not cross the blood-brain barrier, prior to treatment with compound (2). FIG. 12 summarizes the results of these studies.

Example 54

Pruritus Model in Mice

Groups of 10 (and in one case, 11) male Swiss Webster mice (25-30 g) were used. Each animal was weighed and allowed to acclimate for at least one hour in individual, rectangular observation boxes. The tails of mice were immersed for 30 seconds in warm water to dilate tail veins and the animals then received an intravenous injection of either vehicle (saline) or compound (2) (0.01, 0.03, 0.10 and 0.30 mg of free base/kg). Fifteen minutes later, each mouse was given either GNTI dihydrochloride (Tocris) (0.30 mg/kg; 0.25 ml/25 g) or compound 48/80 (Sigma) (50 μg in 0.10 ml saline) subcutaneously behind the neck. The animals were then observed in pairs (occasionally in threes) and the number of hind leg scratching movements directed at the neck was counted for 30 minutes. The mean percent inhibition of scratching caused by compound (2) was plotted and the dose associated with 50% inhibition was obtained by linear regression analysis (PharmProTools). Table IX summarizes the results of these experiments.

TABLE IX

Effects of Compound (2) on Pruritus Induced by Either Compound 48/80 or GNTI in Mice.

| Compound # | Compound 48/80 Model $ED_{50}$ (mg/kg, iv, 15 min post-dose) | GNTI Model $ED_{50}$ (mg/kg, iv, 15 min post-dose) |
|---|---|---|
| (2) | 0.08 (0.04-0.2) | 0.05 (0.02-0.1) |

The specifications of each of the U.S. patents and published patent applications, and the texts of the literature references cited in this specification are herein incorporated by reference in their entireties. In the event that any definition or description contained found in one or more of these references is in conflict with the corresponding definition or description herein, then the definition or description disclosed herein is intended.

The examples provided herein are for illustration purposes only and are not intended to limit the scope of the invention, the full breadth of which will be readily recognized by those of skill in the art.

What is claimed is:

1. A method of preventing, inhibiting or treating pain; or of inhibiting or treating pancreatitis or pruritis in a mammal, the method comprising administering to the mammal by injection a composition comprising an effective amount of a synthetic peptide amide having the formula:

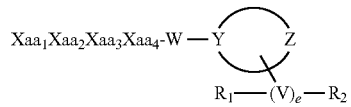

or a stereoisomer, mixture of stereoisomers, pharmaceutically acceptable salt, hydrate, acid salt hydrate, or N-oxide thereof, wherein $Xaa_1$ is selected from the group consisting of (A)(A')D-Phe, (A)(A')($\alpha$-Me)D-Phe, D-Tyr, D-Tic, D-tert-leucine, D-neopentylglycine, D-phenylglycine, D-homophenylalanine, and $\beta$-(E)D-Ala, wherein each (A) and each (A') are phenyl ring substituents independently selected from the group consisting of —H, —F, —Cl, —$NO_2$, —$CH_3$, —$CF_3$, —CN, and —$CONH_2$, and wherein each (E) is independently selected from the group consisting of cyclobutyl, cyclopentyl, cyclohexyl, pyridyl, thienyl and thiazolyl;

$Xaa_2$ is selected from the group consisting of (A)(A')D-Phe, 3,4-dichloro-D-Phe, (A)(A')($\alpha$-Me)D-Phe, D-1Nal, D-2Nal, D-Tyr, (E)D-Ala and D-Trp;

$Xaa_3$ is selected from the group consisting of D-Nle, D-Phe, (E)D-Ala, D-Leu, ($\alpha$-Me)D-Leu, D-Hle, D-Val, and D-Met;

$Xaa_4$ is selected from the group consisting of $(B)_2$D-Arg, $(B)_2$D-Nar, $(B)_2$D-Har, $\zeta$-(B)D-Hlys, D-Dap, $\epsilon$-(B)D-Lys, $\epsilon$-(B)$_2$-D-Lys, D-Amf, amidino-D-Amf, $\gamma$-(B)$_2$D-Dbu, $\delta$-(B)$_2\alpha$-(B')D-Orn, D-2-amino-3(4-piperidyl)propionic acid, D-2-amino-3(2-aminopyrrolidyl) propionic acid, D-$\alpha$-amino-$\beta$-amidinopropionic acid, $\alpha$-amino-4-piperidineacetic acid, cis-$\alpha$,4-diaminocyclohexane acetic acid, trans-$\alpha$,4-diaminocyclohexaneacetic acid, cis-$\alpha$-amino-4-methylaminocyclo-hexane acetic acid, trans-$\alpha$-amino-4-methylaminocyclohexane acetic acid, $\alpha$-amino-1-amidino-4-piperidineacetic acid, cis-$\alpha$-amino-4-guanidinocyclohexane acetic acid, and trans-$\alpha$-amino-4-guanidinocyclohexane acetic acid, wherein each (B) is independently selected from the group consisting of H and $C_1$-$C_4$ alkyl, and (B') is H or ($\alpha$-Me);

W is selected from the group consisting of:
Null, provided that when W is null, Y is N;
—NH—$(CH_2)_b$— with b equal to zero, 1, 2, 3, 4, 5, or 6; and
—NH—$(CH_2)_c$—O— with c equal to 2, or 3, provided that Y is C;

the moiety

is an optionally substituted 4 to 8-membered heterocyclic ring moiety wherein all ring heteroatoms in said ring moiety are N; wherein Y and Z are each independently C or N; provided that when such ring moiety is a six, seven or eight-membered ring, Y and Z are separated by at least two ring atoms; and provided that when such ring moiety has a single ring heteroatom which is N, then such ring moiety is non-aromatic;

V is $C_1$-$C_6$ alkyl, and e is zero or 1, wherein when e is zero, then V is null and $R_1$ and $R_2$ are directly bonded to the same or different ring atoms;

wherein (i) $R_1$ is selected from the group consisting of —H, —OH, halo, —$CF_3$, —$NH_2$, —COOH, $C_1$-$C_6$ alkyl, $C_1$-$C_6$ alkoxy, amidino, $C_1$-$C_6$ alkyl-substituted amidino, aryl, optionally substituted heterocyclyl, Pro-amide, Pro, Gly, Ala, Val, Leu, Ile, Lys, Arg, Orn, Ser, Thr, —CN, —$CONH_2$, —COR', —$SO_2$R', —CONR'R", —NHCOR', OR' and $SO_2NR'R"$; wherein said optionally substituted heterocyclyl is optionally singly or doubly substituted with substituents independently selected from the group consisting of $C_1$-$C_6$ alkyl, $C_1$-$C_6$ alkoxy, oxo, —OH, —Cl, —F, —$NH_2$, —$NO_2$, —CN, —COOH, and amidino; wherein R' and R" are each independently —H, $C_1$-$C_8$ alkyl, aryl, or heterocyclyl or R' and R" are combined to form a 4- to 8-membered ring, which ring is optionally singly or doubly substituted with substituents independently selected from the group consisting of $C_1$-$C_6$ alkyl, —$C_1$-$C_6$ alkoxy, —OH, —Cl, —F, —$NH_2$, —$NO_2$, —CN, —COOH and amidino; and $R_2$ is selected from the group consisting of —H, amidino, singly or doubly $C_1$-$C_6$ alkyl-substituted amidino, —CN, —$CONH_2$, —CONR'R", —NHCOR', —$SO_2NR'R"$ and —COOH; or (ii) $R_1$ and $R_2$ taken together can form an optionally substituted 4- to 9-membered heterocyclic monocyclic or bicyclic ring moiety which is bonded to a single ring atom of the Y and Z-containing ring moiety; or (iii) $R_1$ and $R_2$ taken together with a single ring atom of the Y and Z-containing ring moiety can form an optionally substituted 4- to 8-membered heterocyclic ring moiety to form a spiro structure; or (iv) $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety;

wherein each of said optionally substituted 4-, 5-, 6-, 7-, 8- and 9-membered heterocyclic ring moieties comprising $R_1$ and $R_2$ is optionally singly or doubly substituted with substituents independently selected from the group consisting of $C_1$-$C_6$ alkyl, $C_1$-$C_6$ alkoxy, optionally substituted phenyl, oxo, —OH, —Cl, —F, —NH$_2$, —NO$_2$, —CN, —COOH, and amidino;

provided that when the Y and Z-containing ring moiety is a six or seven membered ring having a single ring heteroatom and e is zero, then $R_1$ is not —OH, and $R_1$ and $R_2$ are not both —H;

provided further that when the Y and Z-containing ring moiety is a six membered ring having two ring heteroatoms, both Y and Z are N and W is null, then —(V)$_e$R$_1$R$_2$ is attached to a ring atom other than Z; and if e is zero, then $R_1$ and $R_2$ are not both —H; and lastly, provided that when $Xaa_3$ is D-Nle, then $Xaa_4$ is not (B)$_2$D-Arg, and when $Xaa_3$ is D-Leu or ($\alpha$Me)D-Leu, then $Xaa_4$ is not $\delta$-(B)$_2$$\alpha$-(B')D-Orn.

2. The method according to claim 1, wherein the mammal is a human.

3. The method according to claim 1, wherein the administration is by subcutaneous injection, intravenous injection, intraperitoneal injection, intra-articular injection, intramuscular injection or intra-ocular injection.

4. The method according to claim 3, wherein the administration is by intravenous injection.

5. The method according to claim 3, wherein the kappa opioid receptor-associated disease or condition is pain.

6. The method according to claim 5, wherein the pain is inflammatory pain, visceral pain, neuropathic pain, post-operative pain or postsurgical procedure pain.

7. The method according to claim 6, wherein the post-operative pain is due to colonoscopy, cystoscopy, hysteroscopy, cervical or endometrial biopsy.

8. The method according to claim 6, wherein the post-operative pain is due to laparoscopic surgery.

9. The method according to claim 6, wherein the surgical procedure is selected from the group consisting of appendectomy, open colorectal surgery, hernia repair, prostatectomy, colonic resection, gastrectomy, splenectomy, colectomy, colostomy, pelvic laparoscopy, tubal ligation, hysterectomy, vasectomy and cholecystectomy.

10. The method according to claim 9, wherein the laparoscopic surgery is laparoscopic-assisted hysterectomy.

11. A method of preventing, inhibiting or treating pain; or of inhibiting or treating pancreatitis or pruritis in a mammal, the method comprising topically administering to the mammal a composition comprising an effective amount of a synthetic peptide amide having the formula:

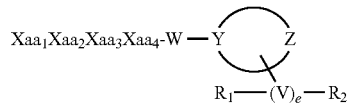

or a stereoisomer, mixture of stereoisomers, pharmaceutically acceptable salt, hydrate, acid salt hydrate, or N-oxide thereof, wherein $Xaa_1$ is selected from the group consisting of (A)(A')D-Phe, (A)(A')($\alpha$-Me)D-Phe, D-Tyr, D-Tic, D-tert-leucine, D-neopentylglycine, D-phenylglycine, D-homophenylalanine, and $\beta$-(E)D-Ala, wherein each (A) and each (A') are phenyl ring substituents independently selected from the group consisting of —H, —F, —Cl, —NO$_2$, —CH$_3$, —CF$_3$, —CN, and —CONH$_2$, and wherein each (E) is independently selected from the group consisting of cyclobutyl, cyclopentyl, cyclohexyl, pyridyl, thienyl and thiazolyl;

$Xaa_2$ is selected from the group consisting of (A)(A')D-Phe, 3,4-dichloro-D-Phe, (A)(A')($\alpha$-Me)D-Phe, D-1Nal, D-2Nal, D-Tyr, (E)D-Ala and D-Trp;

$Xaa_3$ is selected from the group consisting of D-Nle, D-Phe, (E)D-Ala, D-Leu, ($\alpha$-Me)D-Leu, D-Hle, D-Val, and D-Met;

$Xaa_4$ is selected from the group consisting of (B)$_2$D-Arg, (B)$_2$D-Nar, (B)$_2$D-Har, $\zeta$-(B)D-Hlys, D-Dap, $\epsilon$-(B)D-Lys, $\epsilon$-(B)$_2$-D-Lys, D-Amf, amidino-D-Amf, $\gamma$-(B)$_2$D-Dbu, $\delta$-(B)$_2$$\alpha$-(B')D-Orn, D-2-amino-3(4-piperidyl) propionic acid, D-2-amino-3(2-aminopyrrolidyl) propionic acid, D-$\alpha$-amino-$\beta$-amidinopropionic acid, $\alpha$-amino-4-piperidineacetic acid, cis-$\alpha$,4-diaminocyclohexane acetic acid, trans-$\alpha$,4-diaminocyclohexaneacetic acid, cis-$\alpha$-amino-4-methylaminocyclo-hexane acetic acid, trans-$\alpha$-amino-4-methylaminocyclohexane acetic acid, $\alpha$-amino-1-amidino-4-piperidineacetic acid, cis-$\alpha$-amino-4-guanidinocyclohexane acetic acid, and trans-$\alpha$-amino-4-guanidinocyclohexane acetic acid, wherein each (B) is independently selected from the group consisting of H and $C_1$-$C_4$ alkyl, and (B') is H or ($\alpha$-Me);

W is selected from the group consisting of:
Null, provided that when W is null, Y is N;
—NH—(CH$_2$)$_b$— with b equal to zero, 1, 2, 3, 4, 5, or 6; and
—NH—(CH$_2$)$_c$—O— with c equal to 2, or 3, provided that Y is C;

the moiety

is an optionally substituted 4 to 8-membered heterocyclic ring moiety wherein all ring heteroatoms in said ring moiety are N; wherein Y and Z are each independently C or N; provided that when such ring moiety is a six, seven or eight-membered ring, Y and Z are separated by at least two ring atoms; and provided that when such ring moiety has a single ring heteroatom which is N, then such ring moiety is non-aromatic;

V is $C_1$-$C_6$ alkyl, and e is zero or 1, wherein when e is zero, then V is null and $R_1$ and $R_2$ are directly bonded to the same or different ring atoms;

wherein (i) $R_1$ is selected from the group consisting of —H, —OH, halo, —CF$_3$, —NH$_2$, —COOH, $C_1$-$C_6$ alkyl, $C_1$-$C_6$ alkoxy, amidino, $C_1$-$C_6$ alkyl-substituted amidino, aryl, optionally substituted heterocyclyl, Pro-amide, Pro, Gly, Ala, Val, Leu, Ile, Lys, Arg, Orn, Ser, Thr, —CN, —CONH$_2$, —COR', —SO$_2$R', —CONR'R", —NHCOR', OR' and SO₂NR'R"; wherein said optionally substituted heterocyclyl is optionally singly or doubly substituted with substituents independently selected from the group consisting of $C_1$-$C_6$ alkyl, $C_1$-$C_6$ alkoxy, oxo, —OH, —Cl, —F, —NH₂, —NO₂, —CN, —COOH, and amidino; wherein R' and R" are each independently —H, $C_1$-$C_8$ alkyl, aryl, or heterocyclyl or R' and R" are combined to form a 4- to 8-membered ring, which ring is optionally singly or doubly substituted with substituents independently selected from the group consisting of $C_1$-$C_6$ alkyl, —$C_1$-$C_6$ alkoxy, —OH, —Cl, —F, —NH₂, —NO₂, —CN, —COOH and amidino; and R₂ is selected from the group consisting of —H, amidino, singly or doubly $C_1$-$C_6$ alkyl-substituted amidino, —CN, —CONH₂, —CONR'R", —NHCOR', —SO₂NR'R" and —COOH; or (ii) R₁ and R₂ taken together can form an optionally substituted 4- to 9-membered heterocyclic monocyclic or bicyclic ring moiety which is bonded to a single ring atom of the Y and Z-containing ring moiety; or (iii) R₁ and R₂ taken together with a single ring atom of the Y and Z-containing ring moiety can form an optionally substituted 4- to 8-membered heterocyclic ring moiety to form a spiro structure; or (iv) R₁ and R₂ taken together with two or more adjacent ring atoms of the Y and Z-containing ring moiety can form an optionally substituted 4- to 9-membered heterocyclic monocyclic or bicyclic ring moiety fused to the Y and Z-containing ring moiety;

wherein each of said optionally substituted 4-, 5-, 6-, 7-, 8- and 9-membered heterocyclic ring moieties comprising R₁ and R₂ is optionally singly or doubly substituted with substituents independently selected from the group consisting of $C_1$-$C_6$ alkyl, $C_1$-$C_6$ alkoxy, optionally substituted phenyl, oxo, —OH, —Cl, —F, —NH₂, —NO₂, —CN, —COOH, and amidino;

provided that when the Y and Z-containing ring moiety is a six or seven membered ring having a single ring heteroatom and e is zero, then R₁ is not —OH, and R₁ and R₂ are not both —H;

provided further that when the Y and Z-containing ring moiety is a six membered ring having two ring heteroatoms, both Y and Z are N and W is null, then —(V)ₑR₁R₂ is attached to a ring atom other than Z; and if e is zero, then R₁ and R₂ are not both —H; and lastly, provided that when Xaa₃ is D-Nle, then Xaa₄ is not (B)₂D-Arg, and when Xaa₃ is D-Leu or (αMe)D-Leu, then Xaa₄ is not δ-(B)₂α-(B')D-Orn.

12. The method according to claim 11, wherein the mammal is a human.

13. The method according to claim 11, wherein the topical application is to the skin, cornea, oral cavity, vagina or anorectal mucosa.

14. The method according to claim 13, wherein the topical application to the oral cavity is to a lip, tongue, gum, cheek, sublingual surface or to the roof of the mouth.

15. A method of preventing, inhibiting or treating pain; or of inhibiting or treating pancreatitis or pruritis in a mammal, the method comprising orally administering to the mammal a composition comprising an effective amount of a synthetic peptide amide having the formula:

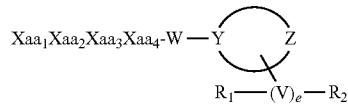

or a stereoisomer, mixture of stereoisomers, pharmaceutically acceptable salt, hydrate, acid salt hydrate, or N-oxide thereof, wherein Xaa₁ is selected from the group consisting of (A)(A')D-Phe, (A)(A')(α-Me)D-Phe, D-Tyr, D-Tic, D-tert-leucine, D-neopentylglycine, D-phenylglycine, D-homophenylalanine, and β-(E)D-Ala, wherein each (A) and each (A') are phenyl ring substituents independently selected from the group consisting of —H, —F, —Cl, —NO₂, —CH₃, —CF₃, —CN, and —CONH₂, and wherein each (E) is independently selected from the group consisting of cyclobutyl, cyclopentyl, cyclohexyl, pyridyl, thienyl and thiazolyl;

Xaa₂ is selected from the group consisting of (A)(A')D-Phe, 3,4-dichloro-D-Phe, (A)(A')(α-Me)D-Phe, D-1Nal, D-2Nal, D-Tyr, (E)D-Ala and D-Trp;

Xaa₃ is selected from the group consisting of D-Nle, D-Phe, (E)D-Ala, D-Leu, (α-Me)D-Leu, D-Hle, D-Val, and D-Met;

Xaa₄ is selected from the group consisting of (B)₂D-Arg, (B)₂D-Nar, (B)₂D-Har, ζ-(B)D-Hlys, D-Dap, ε-(B)D-Lys, ε-(B)₂-D-Lys, D-Amf, amidino-D-Amf, γ-(B)₂D-Dbu, δ-(B)₂α-(B')D-Orn, D-2-amino-3(4-piperidyl) propionic acid, D-2-amino-3(2-aminopyrrolidyl) propionic acid, D-α-amino-β-amidinopropionic acid, α-amino-4-piperidineacetic acid, cis-α,4-diaminocyclohexane acetic acid, trans-α,4-diaminocyclohexaneacetic acid, cis-α-amino-4-methylaminocyclo-hexane acetic acid, trans-α-amino-4-methylaminocyclohexane acetic acid, α-amino-1-amidino-4-piperidineacetic acid, cis-α-amino-4-guanidinocyclohexane acetic acid, and trans-α-amino-4-guanidinocyclohexane acetic acid, wherein each (B) is independently selected from the group consisting of H and $C_1$-$C_4$ alkyl, and (B') is H or (α-Me);

W is selected from the group consisting of:
  Null, provided that when W is null, Y is N;
  —NH—(CH₂)ᵦ— with b equal to zero, 1, 2, 3, 4, 5, or 6; and
  —NH—(CH₂)c—O— with c equal to 2, or 3, provided that Y is C;

the moiety

is an optionally substituted 4 to 8-membered heterocyclic ring moiety wherein all ring heteroatoms in said ring moiety are N; wherein Y and Z are each independently C or N; provided that when such ring moiety is a six, seven or eight-membered ring, Y and Z are separated by at least two ring atoms; and provided that when such ring moiety has a single ring heteroatom which is N, then such ring moiety is non-aromatic;

V is $C_1$-$C_6$ alkyl, and e is zero or 1, wherein when e is zero, then V is null and R₁ and R₂ are directly bonded to the same or different ring atoms;

wherein
(i) $R_1$ is selected from the group consisting of —H, —OH, halo, —CF$_3$, —NH$_2$, —COOH, C$_1$-C$_6$ alkyl, C$_1$-C$_6$ alkoxy, amidino, C$_1$-C$_6$ alkyl-substituted amidino, aryl, optionally substituted heterocyclyl, Pro-amide, Pro, Gly, Ala, Val, Leu, Ile, Lys, Arg, Orn, Ser, Thr, —CN, —CONH$_2$, —COR', —SO$_2$R', —CONR'R", —NHCOR', OR' and SO$_2$NR'R"; wherein said optionally substituted heterocyclyl is optionally singly or doubly substituted with substituents independently selected from the group consisting of C$_1$-C$_6$ alkyl, C$_1$-C$_6$ alkoxy, oxo, —OH, —Cl, —F, —NH$_2$, —NO$_2$, —CN, —COOH, and amidino; wherein R' and R" are each independently —H, C$_1$-C$_8$ alkyl, aryl, or heterocyclyl or R' and R" are combined to form a 4- to 8-membered ring, which ring is optionally singly or doubly substituted with substituents independently selected from the group consisting of C$_1$-C$_6$ alkyl, —C$_1$-C$_6$ alkoxy, —OH, —Cl, —F, —NH$_2$, —NO$_2$, —CN, —COOH and amidino; and $R_2$ is selected from the group consisting of —H, amidino, singly or doubly C$_1$-C$_6$ alkyl-substituted amidino, —CN, —CONH$_2$, —CONR'R", —NHCOR', —SO$_2$NR'R" and —COOH; or (ii) $R_1$ and $R_2$ taken together can form an optionally substituted 4- to 9-membered heterocyclic monocyclic or bicyclic ring moiety which is bonded to a single ring atom of the Y and Z-containing ring moiety; or (iii) $R_1$ and $R_2$ taken together with a single ring atom of the Y and Z-containing ring moiety can form an optionally substituted 4- to 8-membered heterocyclic ring moiety to form a spiro structure; or (iv) $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety;

wherein each of said optionally substituted 4-, 5-, 6-, 7-, 8- and 9-membered heterocyclic ring moieties comprising $R_1$ and $R_2$ is optionally singly or doubly substituted with substituents independently selected from the group consisting of C$_1$-C$_6$ alkyl, C$_1$-C$_6$ alkoxy, optionally substituted phenyl, oxo, —OH, —Cl, —F, —NH$_2$, —NO$_2$, —CN, —COOH, and amidino;

provided that when the Y and Z-containing ring moiety is a six or seven membered ring having a single ring heteroatom and e is zero, then $R_1$ is not —OH, and $R_1$ and $R_2$ are not both —H;

provided further that when the Y and Z-containing ring moiety is a six membered ring having two ring heteroatoms, both Y and Z are N and W is null, then —(V)$_e$R$_1$R$_2$ is attached to a ring atom other than Z; and if e is zero, then $R_1$ and $R_2$ are not both —H; and lastly, provided that when Xaa$_3$ is D-Nle, then Xaa$_4$ is not (B)$_2$D-Arg, and when Xaa$_3$ is D-Leu or (αMe)D-Leu, then Xaa$_4$ is not δ-(B)$_2$α-(B')D-Orn.

16. The method according to claim 15, wherein the mammal is a human.

17. The method according to claim 15, wherein the kappa opioid receptor-associated disease or condition is pain.

18. The method according to claim 17, wherein the pain is inflammatory pain, visceral pain, neuropathic pain, post-operative pain or postsurgical procedure pain.

19. The method according to claim 18, wherein the post-operative pain is due to colonoscopy, cystoscopy, hysteroscopy, cervical or endometrial biopsy.

20. The method according to claim 18, wherein the surgical procedure is selected from the group consisting of appendectomy, open colorectal surgery, hernia repair, prostatectomy, colonic resection, gastrectomy, splenectomy, colectomy, colostomy, pelvic laparoscopy, tubal ligation, hysterectomy, vasectomy and cholecystectomy.

* * * * *